United States Patent [19]

Bach et al.

[11] Patent Number: 5,684,034
[45] Date of Patent: Nov. 4, 1997

[54] 1H-INDOLE-3-ACETAMIDE SPLA₂ INHIBITORS

[75] Inventors: Nicholas J. Bach, Indianapolis; Robert D. Dillard, Zionsville; Susan E. Draheim, Indianapolis; Robert B. Hermann, Indianapolis; Richard W. Schevitz, Indianapolis, all of Ind.

[73] Assignee: Eli Lilly and Company, Indianapolis, Ind.

[21] Appl. No.: 435,256

[22] Filed: May 5, 1995

Related U.S. Application Data

[60] Division of Ser. No. 208,721, Mar. 15, 1994, abandoned, which is a continuation-in-part of Ser. No. 48,629, Apr. 16, 1993, abandoned.

[51] Int. Cl.⁶ .................... A61K 31/40; C07D 209/12
[52] U.S. Cl. ............... 514/419; 514/418; 548/113; 548/496; 548/483; 548/486; 548/493
[58] Field of Search .................. 514/419, 418; 548/113, 496, 483, 486, 493

[56] References Cited

U.S. PATENT DOCUMENTS

| | | | |
|---|---|---|---|
| 2,825,734 | 3/1958 | Speeter | 260/319 |
| 2,890,223 | 6/1959 | Woolley | 260/319 |
| 3,196,162 | 7/1965 | Sarett | 260/319 |
| 3,242,162 | 3/1966 | Sarett | 260/211 |
| 3,242,163 | 3/1966 | Sarett | 260/211 |
| 3,242,193 | 3/1966 | Sarett | 260/319 |
| 3,271,416 | 9/1966 | Shen | 260/326 |
| 4,428,962 | 1/1984 | Bristol et al. | 424/274 |

FOREIGN PATENT DOCUMENTS 0 620 215 A1  10/1994  European Pat. Off. .

OTHER PUBLICATIONS

Seilhamer, Jeffery, et al., "Cloning and Recombinant Expression of Phospholipase A₂ present in Rheumatoid Arthritic Synovial Fluid"; *The Journal of Biolgical Chemistry*, 254:10, Apr. 5, 1989, pp. 5335–5338.

Kramer, Ruth, et al., "Structure and Properties of a Human Non–Pancreatic Phospholipase A₂", *The Journal of Biological Chemistry*, 264.10, Apr. 5, 1989, pp. 5768–5775.

Shaw, Elliott, "The Synthesis of Tryptamines Related to Serotonin", *Journal American Chemical Soc.*, vol. 77, Aug. 20, 1955, pp. 4319–4324.

Julia, Marc, et al., "No. 193—Recherches en serie indolique". Memorie No. V: *Bull. Soc. Chim.*, 1962, 1042.

Walton, Edward, et al., "Some Analogs of 1–p–Chlorobenzyl–5–methylindole–3–acetic Acid", *J. Med. Chem.*, vol. 11, 1968, pp. 1252–1255.

Romeo, E., "2–Aryl–3–Indoleglyoxylamides (FGIN–1): A New Class of Potent and Specific Ligands for the Mitochondrial DBI Receptor (MDR)", *The Journal of Pharmacology and Experimental Therapeutics*, vol. 262, No. 3, pp. 971–978 (1992).

Carlin, Robert B., et al., "Studies on the Fischer Indole Synthesis I", *Journal American Chemical Society*, vol. 70, Oct. 1948, pp. 3421–3424.

Yoshihiko Ito, et al., "The First Total Synthesis of OPC–15161", *J. Org. Chem.*, 1991, 56, pp. 4864–4867.

Clark, Robin D., et al., "Preparation of Indoles and Oxindoles from N–(Tert–Butoxycarbonyl)–2–Alkylanilines", *Synthesis*, Oct. 1991, pp. 871–878.

Wayland, E. Noland, et al., "Nitration of Indoles II, The Mononitration of Methylindoles", *J. Org. Chem.*, vol. 28, Sep. 1963, pp. 2262–2266.

Miyaura, N., et al., "The Palladium–Catalyzed Cross–Coupling Reaction of Phenylboronic Acid with Haloarenes in the Presnce of Bases", *Synthetic Communications*, 11;7, 1981, pp. 513–519.

Reynolds, et al., "Analysis of Human Synovial Fluid Phospholipase A₂ on Short Chain Phosphatidylcholine–Mixed Micelles; Development of a Spectrophotometric Assay Suitable for a Microtiterplate Reader", *Analytical Biochem*, 204, 1992; pp. 190–197.

Rossum, et al., "Cumulative Dose–Response Curves", *Arch. Int. Pharmacodyn*, 143, No. 3–4, 1963, pp. 299–330.

Waud, Douglas R. "Analysis of Dose–Response Relationships", *Advances in General and Cellular Pharmacology*, eds., Narahashi, Branchi, 1:145–178, 1976.

Andreani, A., et al., "Nonsteroidal Antiinflammatory Agents. 2. Synthesis and Biological Activity of 2–Chlorindolecarboxylic Acids"; *Journal of Medicinal Chemistry*, vol. 20, No. 10, 1977, pp. 1344–1346.Julia, Marc, et al., "No. 208—Recherches en serie indolique. XIII. Sur quelques methoxy –5 et. –6 tryptamines", *Bulletin de La Societe Chimique de France*, Paris, France; 1965, pp. 1411–1417.

Chemical Abstracts, vol. 1/2. No. 24, Abstract No. 223181s; "Kinetics of hydrolysis of indomethacin and indomethacin ester predrigs in aqueous solution" Jun. 11, 1990, p. 407.

(List continued on next page.)

*Primary Examiner*—Jacqueline Haley
*Attorney, Agent, or Firm*—Roger S. Benjamin; David E. Boone

[57] ABSTRACT

A class of novel 1-indole-3-acetamides represented by the formula;

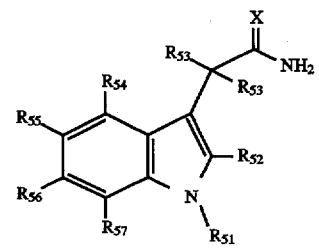

is disclosed together with the use of such indole compounds for inhibiting sPLA₂ mediated release of fatty acids.

18 Claims, No Drawings

OTHER PUBLICATIONS

Chemical Abstracts Service. "Registry Handbook", Number Section, Registry Numbers (see, CAS RN 6264, 33–1) 1965–1971, Publ. American Chemical Society.

Von. K.H. Boltze; O. Brendler, et al., "Chemische Struktur and antiophlogistische Wirkung in der Reihe der substituierten Indol–3–essigsauren", *Arznermittel Forschung Drug Research*, vol. 30 (II), No. 8A, 1980, Aulendorf, DE, pp. 1314–1325.

Julia, Marc., et al., "Recherches en serie indolique. VI. Sur quelques tryptamines substituees", *Bulletin de La Societe Chimique de France*, Paris, France; 1962, pp. 1060–1068.

1H-INDOLE-3-ACETAMIDE SPLA$_2$ INHIBITORS

This application is a division of application Ser. No. 08/208,721 filed Mar. 15, 1994 now abandoned which is a continuation-in-part of Ser. No. 08/048,629 filed Apr. 16, 1993 abandoned.

BACKGROUND OF THE INVENTION

1. Field of the Invention

This invention relates to novel 1H-indole-3-acetamides useful for inhibiting sPLA$_2$ mediated release of fatty acids for conditions such as septic shock.

2. Background Information

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by over-production of sPLA$_2$; such as septic shock, adult respiratory distress syndrome, pancreatitis, trauma, bronchial asthma, allergic rhinitis, rheumatoid arthritis, and etc.

Indolyl-3 substituted compounds having glyoxylamide functionality are described in U.S. Pat. No. 2,825,734. This patent related to a process for converting glyoxyamides to 3-(2-amino-1-hydroxyethyl)indoles.

U.S. Pat. No. 3,271,416 describes indolyl aliphatic acids as sun screening agents and intermediates. These acids may be —NH$_2$ substituted (see, definition of M in claim 1) and require 5- or 6-position substitution with nitrogen or sulfur functional groups.

U.S. Pat. No. 2,890,223 and the article "The Synthesis of Tryptamines Related to Serotonin", by Elliott Shaw, J. Am. Chem. Soc., Vol. 77, 1955, (pp. 4319–4324) describe several amide derivatives of 3-indoleacetic acids. These compounds are used in the preparation of 5-lower alkoxy tryptamines and are stated to have utility for influencing serotonin related functions in the brain. In addition, the article, "Recherches en serie indolique. VI sur tryptamines substituees", by Marc Julia, Jean Igolen and Hanne Igolen, Bull. Soc. Chim. France, 1962, pp. 1060–1068, describes certain indole-3-acetamides and their conversion to tryptamine derivatives.

Selected indoyl amide type compounds have been described in the literature for the treatment of arthritic disorders. Thus, U.S. Pat. Nos. 3,196,162; 3,242,162; 3,242,163; and 3,242,193 (see, Col. 3, lines 55–60, Example 56) describe indolyl aliphatic acids together with their related salts, esters, and amides. These compounds are closely related to compounds like indomethacin, have a substituted benzyl group at the 1 position and likely achieve their beneficial action being cyclooxygenase inhibitors.

The article, "Some Analogs of 1-p-Chlorobenzyl-5-memhylindole-3-acetic Acid", by E. Walton, et al., J. Med. Chem., Vol. 11, 2968, pp. 1252–1255, describes the preparation of isomeric methyl 3-(1-p-chlorobenzyl-5-methoxy-3-methylindole-2)propionate.

The article, "2-Aryl-3-Indoleacetamides (FGIN-1): A New Class of Potent and Specific Ligands for the Mitochondrial DBI Receptor (MDR)" by E. Romeo, et al. The Journal of Pharmacology and Experimental Therapeutics Vol. 262, No. 3, (pp. 971–978) describes certain 2-aryl-3-indolacetamides having research applications in mammalian central nervous systems.

It is desirable to develop new compounds and treatments for sPLA$_2$ induced diseases.

SUMMARY OF THE INVENTION

This invention is a novel use of the class of compounds known as 1H-indole-3-acetamides to inhibit human sPLA$_2$ mediated release of fatty acids.

This invention is also novel classes of 1H-indole-3-acetamides having potent and selective effectiveness as inhibitors of human sPLA$_2$.

This invention is also pharmaceutical compositions containing the 1H-indole-3-acetamides of the invention.

This invention is also a method of preventing and treating septic shock using the 1H-indole-3-acetamides of the invention.

DETAILED DESCRIPTION OF THE INVENTION

Definitions:

The 1H-indole-3-acetamides of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the seated number range of carbon atoms, and typified by groups such as vinyl, propenyl, crotonyl, isopentenyl, and various butenyl isomers.

The term, "halo" means fluoro, chloro, bromo, or iodo.

The term, "heterocyclic radical", refers to radicals derived from monocyciic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pryidinyl, dipyridylyl. phenylpyridinyl, benzylpyridinyl, pyrimidinyl, phenylpyrimidinyl, pyrazinyl, 1,3,5-triazinyl, quinolinyl, phthalazinyl, quinazolinyl, quinoxalinyl.

The term, "carbocyclic radical" refers to radicals derived from a saturated or unsaturated, substituted or unsubstituted 5 to 14 membered organic nucleus whose ring forming atoms are solely carbon atoms Typical carbocyclic radicals are cycloalkyl, cycloalkenyl, phenyl, naphthyl, norbornanyl, bicycloheptadienyl, tolulyl, xylenyl, biphenyl, indenyl, acenaphthylenyl, and anthracenyl.

The term, "non-interfering substituent", refers to radicals suitable for substitution at positions 4, 5, 6, and/or 7 on the indole nucleus (as hereinafter depicted in Formula I) and radical(s) suitable for substitution on the heterocyclic radical and carbocyclic radical as defined above. Illustrative non-interfering radicals are $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, (—CONHSO$_2$R), —CHO, amino, amidino, bromo, carbamyl, carboxyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, trifluoromethyl, and $C_1$–$C_6$ carbonyl; where n is from 1 to 8.

The term, "amine", includes primary, secondary and tertiary amines.

The term, "hydrocarbyl" means an organic group containing only carbon and hydrogen.

The term, "acidic group" means an organic group which when attached to an indole nucleus, through suitable connecting atoms, acts as a proton donor capable of hydrogen bonding. Illustrative of an acidic group are the following:

-5-tetrazolyl,

—SO$_3$H,

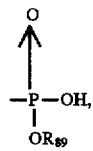

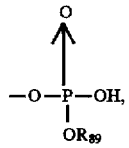

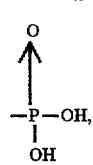

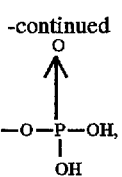

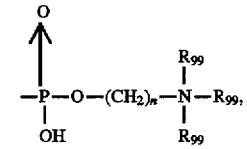

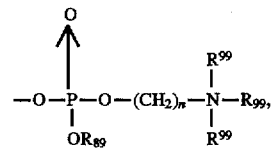

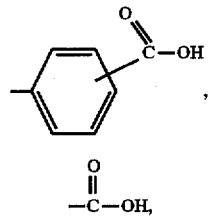

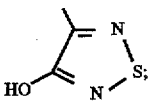

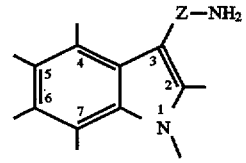

where n is 1 to 8, $R_{89}$ is a metal or $C_1$–$C_{10}$ alkyl, and $R_{99}$ is hydrogen or $C_1$–$C_{10}$ alkyl.

The compounds of the invention having utility for inhibiting human sPLA$_2$ mediated release of fatty acids are selected from "1H-indole-3-acetamides" having the general formula (A);

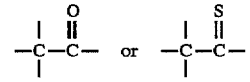

(A)

where Z is a divalent organic radical represented by $$-\underset{|}{C}-\overset{O}{\underset{\|}{C}}-\quad \text{or} \quad -\underset{|}{C}-\overset{S}{\underset{\|}{C}}-$$

and the unsubstituted positions on the indolyl nucleus are independently satisfied by hydrogen or a non-interfering substituent. The indole nitrogen of formula (A) is preferably substituted by a —(CH$_2$)$_{1\text{-}8}$-(carbocyclic radical) or a —(CH$_2$)$_{1\text{-}8}$-(heterocyclic radical).

A preferred class of compounds according this invention are those having aryl, alkyl, haloalkyl, alkenyl, or alkynyl, groups on the indole nitrogen together with a relatively short (up to about 3 carbon atom size or equivalent) group at the 2-position (adjacent the indole nitrogen). Such 1H-indole-3-acetamides are represented by the formula (I), and pharmaceutically acceptable salts thereof;

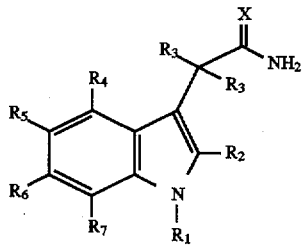
(I)

wherein;

X is oxygen or sulfur;

$R_1$ is selected from groups (i), (ii) and (iii) where;
(i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or
(ii) is selected from the group; phenyl, naphthyl, indenyl, and biphenyl, where the members of the group are unsubstituted or substituted by the substituents halo, —CN, —CHO, —OH, nitro, —SH, $C_1$–$C_{10}$ alkylthio, $C_1$–$C_{10}$ alkoxyl, $C_1$–$C_{10}$ alkyl, carboxyl, amino, or hydroxyamino; or
(iii) is —$(CH_2)_n$—$(R_{80})$, or —(NH)—$(R_{81})$, where n is 1 to 8, and $R_{80}$ is a group recited in (i), and $R_{81}$ is selected from a group recited in (i) or (ii);

$R_2$ is hydrogen, halo, $C_1$–$C_3$ alkyl ethenyl, cyclopropyl, $C_1$–$C_2$ alkylthio, $C_1$–$C_2$ alkoxy, —CHO, or —CN;

each $R_3$ is independently hydrogen, halo, or methyl;

$R_4$, $R_5$, $R_6$, and $R_7$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or any two adjacent hydrocarbyl groups in the set $R_4$, $R_5$, $R_6$, and $R_7$, combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkyl thio, arylthio, thioacetal, —C(O)O($C_1$–$C_{10}$ alkyl), hydrazide, hydrazino, hydrazido, —$NH_2$, —$NO_2$, —$NR_{82}R_{83}$, and —C(O)$NR_{82}R_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

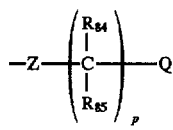

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON($R_{82}R_{83}$), -5-tetrazolyl, —$SO_3H$,

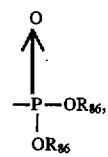

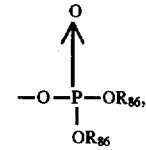

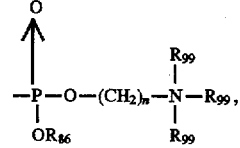

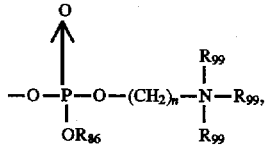

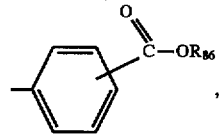

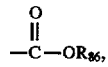

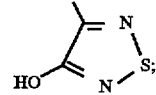

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

Another preferred class of indoles according to this invention are those having alkyl, aryl, or benzyl groups or their derivatives on the indole nitrogen. Such 1H-indole-3-acetamides are represented by the formula (II), and pharmaceutically acceptable salts thereof,

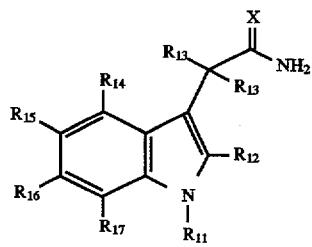
(II)

wherein;

X is oxygen or sulfur;

$R_{11}$ is selected from groups (i), (ii) (iii) and (iv) where;
(i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or
(ii) is aryl or aryl substituted by halo, nitro, —CN, —CHO, —OH, —SH, $C_1$–$C_{10}$ alkyl, $C_1$–$C_{10}$ alkylthio, $C_1$–$C_{10}$ alkoxyl, carboxyl, amino, or hydroxyamino; or (iii) is —(CH$_2$)$_n$—(R$_{80}$), or —(NH)—(R$_{81}$), where n is 1 to 8, and R$_{80}$ is a group recited in (i), and R$_{81}$ is selected from a group recited in (i) or (ii);

(iv) is

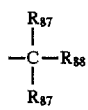

where R$_{87}$ is hydrogen or C$_1$–C$_{10}$ alkyl, and R$_{88}$ is selected from the group; phenyl, naphthyl, indenyl, and biphenyl, unsubstituted or substituted by halo, —CN, —CHO, —OH, —SH, C$_1$–C$_{10}$ alkylthio, C$_1$–C$_{10}$ alkoxyl, phenyl, nitro, C$_1$–C$_{10}$ alkyl, C$_1$–C$_{10}$ haloalkyl, carboxyl, amino, hydroxyamino; or a substituted or unsubstituted 5 to 8 membered heterocyclic ring;

R$_{12}$ is halo, C$_1$–C$_2$ alkylthio, or C$_1$–C$_2$ alkoxy;

each R$_{13}$ is independently hydrogen, halo, or methyl;

R$_{14}$, R$_{15}$, R$_{16}$, and R$_{17}$ are each independently hydrogen, C$_1$–C$_{10}$ alkyl, C$_1$–C$_{10}$ alkenyl, C$_1$–C$_{10}$ alkynyl, C$_3$–C$_8$ cycloalkyl, aryl, aralkyl, or any two adjacent hydrocarbyl groups in the set R$_{14}$, R$_{15}$, R$_{16}$, and R$_{17}$, combine with the ring carbon atoms to which they are attached to form a 2 or 6 membered substituted or unsubstituted carbocyclic ring; or C$_1$–C$_{10}$ haloalkyl, C$_1$–C$_{10}$ alkoxy, C$_1$–C$_{10}$ haloalkoxy, C$_4$–C$_8$ cycloalkoxy, phenoxy, halo, hydroxy, carboxyl, —SH, —CN, C$_1$–C$_{10}$ alkylthio, arylthio, thioacetal, —C(O)O(C$_1$–C$_{10}$ alkyl), hydrazide, hydrazino, hydrazido, —NH$_2$, —NO$_2$, —NR$_{82}$R$_{83}$, and —C(O)NR$_{82}$R$_{83}$, where, R$_{82}$ and R$_{83}$ are independently hydrogen, C$_1$–C$_{10}$ alkyl, C$_1$–C$_{10}$ hydroxyalkyl, or taken together with N, R$_{82}$ and R$_{83}$ form a 5 to 8 membered heterocyclic ring; or a group having the formula;

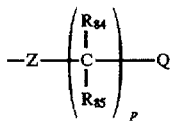

where,

R$_{84}$ and R$_{85}$ are each independently selected from hydrogen, C$_1$–C$_{10}$ alkyl, hydroxy, or R$_{84}$ and R$_{85}$ taken together are =O;

p is 1 to 5,

Z is a bond, —O—, —N(C$_1$–C$_{10}$ alkyl)—, —NH—, or —S—; and

Q is —CON(R$_{82}$R$_{83}$), -5-metrazolyl, —SO$_3$H,

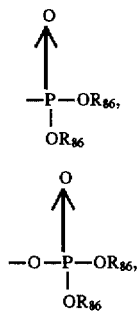

where n is from 1 to 8, R$_{86}$ is independently selected from hydrogen, a metal, or C$_1$–C$_{10}$ alkyl, and R$_{99}$ is selected from hydrogen or C$_1$–C$_{10}$ alkyl.

Another preferred group of indoles according to this invention are those having two key substituents; namely, (1) an acidic group at one or both the 4 or 5 positions (viz., R$_{24}$ and R$_{25}$ as depicted in formula III), and (2) a benzyl or substituted benzyl group on the indole nitrogen. Such 1H-indole-3-acetamides are represented by the formula (III), and pharmaceutically acceptable salts thereof, (III)

wherein;

X is oxygen or sulfur;

R$_{21}$ is —(CH$_2$)$_n$—(R$_{80}$), or —(NH)—(R$_{80}$), where n is 1 to 8, and R$_{80}$ is aryl or aryl substituted by C$_1$–C$_{10}$ alkyl, C$_1$–C$_{10}$ alkenyl, C$_1$–C$_{10}$ alkynyl, C$_1$–C$_{10}$ haloalkyl, C$_4$–C$_{12}$ cycloalkyl, C$_1$–C$_{10}$ hydroxyalkyl, carboxyl, halo, —CN, —CHO, —OH, —SH, C$_1$–C$_{10}$ alkylthio, C$_1$–C$_{10}$ alkoxyl, carboxyl, amino, or hydroxyamino, or a substituted or unsubstituted 5 to 8 membered heterocyclic ring;

R$_{22}$ is hydrogen, halo, C$_1$–C$_3$ alkyl, ethenyl, cyclopropyl, C$_1$–C$_2$ alkylthio, C$_1$–C$_2$ alkoxy, —CHO, —CN;

each R$_{23}$ is independently hydrogen, halo, or methyl;

R$_{24}$ and R$_{25}$ are each independently selected from (a) and (b) where;

(a) is hydrogen, halo, alkyl, or alkoxy, and;

(b) is a group having the formula;

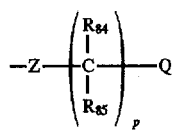

with the proviso that at least one of $R_{24}$ and $R_{25}$ must be selected from (b), and where;

$R_{84}$ and $R_{85}$ are each independently selected from hydrogen, $C_1$-$C_{10}$ alkyl, hydroxy, or $R_{84}$ and $R_{85}$ taken together are =O;

p is 1 to 5,

Z is a bond, —O—, —N($C_1$-$C_{10}$ alkyl)—, —NH—, or —S—; and

Q is —CON($R_{82}R_{83}$), -5-tetrazolyl, —SO$_3$H,

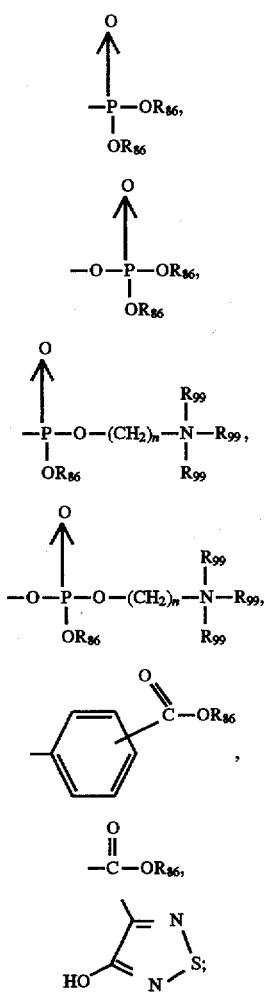

where n is 1 to 8, $R_{86}$ is independently selected from hydrogen, a metal, or $C_1$-$C_{10}$ alkyl, and $R_{99}$ is selected from hydrogen or $C_1$-$C_{10}$ alkyl.

$R_{26}$, and $R_{27}$ are each independently hydrogen, $C_1$-$C_{10}$ alkyl, $C_1$-$C_{10}$ alkenyl, $C_1$-$C_{10}$ alkynyl, $C_3$-$C_8$ cycloalkyl, aryl, aralkyl, or the adjacent hydrocarbyl groups in the groups $R_{26}$ and $R_{27}$ combine with the ring carbon atoms to which they are attached to form a 5 or 6 membered substituted or unsubstituted carbocyclic ring; or $C_1$-$C_{10}$ haloalkyl, $C_1$-$C_{10}$ alkoxy, $C_1$-$C_{10}$ haloalkoxy, $C_4$-$C_8$ cycloalkoxy, phenoxy, halo, hydroxy, carboxyl, —SH, —CN, $C_1$-$C_{10}$ alkylthio, arylthio, thioacetal, —C(O)O($C_1$-$C_{10}$ alkyl), hydrazide, hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$-$C_{10}$ alkyl, $C_1$-$C_{10}$ hydroxyalkyl, or taken together with N, $R_{82}$ and $R_{83}$ form a 5 to 8 membered heterocyclic ring; or a group having the formula;

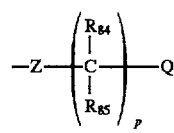

where, $R_{84}$ and $R_{85}$ are each independently selected from hydrogen, $C_1$-$C_{10}$ alkyl, hydroxy, or $R_{84}$ and $R_{85}$ taken together are =O;

p is 1 to 5,

Z is a bond, —O—, —N($C_1$-$C_{10}$ alkyl)—, —NH—, or —S—; and

Q is —CON($R_{82}R_{83}$), -5-tetrazolyl, —SO$_3$H,

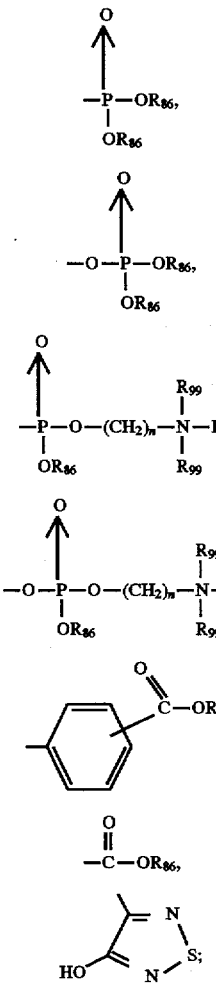

where n is 1 to 8, $R_{86}$ is independently selected from hydrogen, a metal, or $C_1$-$C_{10}$ alkyl, and $R_{99}$ is selected from hydrogen or $C_1$-$C_{10}$ alkyl.

Another preferred class of indoles according to this invention are those having two key substituents; namely, (1) an acidic group at one or both the 4 or 5 positions (viz., $R_{34}$ and $R_{35}$ as depicted in formula IV, and (2) a small substituent containing halogen, sulfur, or oxygen at the 2-position of the indole ring ($R_{32}$ of formula IV). Such 1H-indole-3-acetamides are represented by the formula (IV), and pharmaceutically acceptable salts thereof,

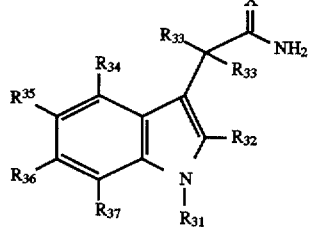

(IV)

wherein;

X is oxygen or sulfur;

$R_{31}$ is selected from groups (i), (ii) and (iii) where;
- (i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or
- (ii) is aryl or aryl substituted by halo, —CN, —CHO, —OH, —SH, $C_1$–$C_{10}$ alkylthio, $C_1$–$C_{10}$ alkoxyl, carboxyl, amino, or hydroxyamino;
- (iii) is

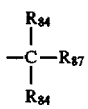

where $R_{84}$ is hydrogen or $C_1$–$C_{10}$ alkyl, and $R_{87}$ is selected from the group; phenyl, naphthyl, indenyl and biphenyl, unsubstituted or substituted by halo, —CN, —CHO, —OH, —SH, $C_1$–$C_{10}$ alkylthio, $C_1$–$C_{10}$ alkoxy, carboxyl, amino, hydroxyamino; or a substituted or unsubstituted 5 to 8 membered heterocyclic ring;

$R_{32}$ is halo, $C_1$–$C_2$ alkylthio, $C_1$–$C_2$ alkoxy;

each $R_{33}$ is independently hydrogen, halo, or methyl;

$R_{34}$ and $R_{35}$ are each independently selected from (a) and (b) where;
- (a) is hydrogen, halo, alkyl, or alkoxy, and
- (b) is a group having the formula;

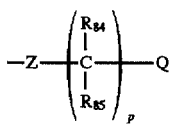

with the proviso that at least one of $R_{34}$ and $R_{35}$ must be selected from (b), and where;

$R_{84}$ and $R_{85}$ are each independently selected from hydrogen, $C_1$–$C_{10}$ alkyl, hydroxy, or $R_{84}$ and $R_{85}$ taken together are =O;

p is 1 to 5;

Z is a bond, —O—, —N($C_1$–$C_{10}$ alkyl)—, —NH—, or —S—; and

Q is —CON($R_{82}R_{83}$), -5-tetrazolyl, —SO$_3$H,

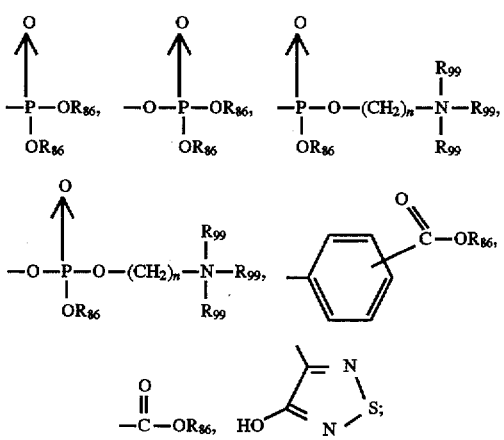

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

$R_{36}$ and $R_{37}$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or the adjacent hydrocarbyl groups in the groups $R_{36}$ and $R_{37}$ combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkylthio, arylthio, thioacetal, —C(O)O($C_1$–$C_{10}$ alkyl), hydrazide, hydrazino, hydrazido, —NH$_2$, —NO$_2$, —NR$_{82}R_{83}$, and —C(O)NR$_{82}R_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

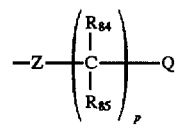

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON($R_{82}R_{83}$), -5-tetrazolyl, —SO$_3$H,

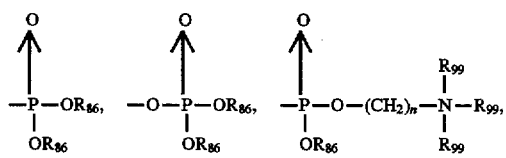

-continued

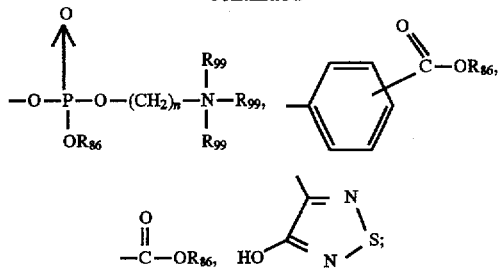

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

A most preferred class of indole compounds according to this invention are those wherein X is oxygen in formula V, the nitrogen of the indole ring is substituted by a benzyl or biphenyl methyl group, and the 2-position on the indole ring (viz., $R_{52}$ in formula V) is substituted with either halo, methylthio, or $C_1$–$C_3$ alkyl. Such 1H-indole-3-acetamides are represented by the formula (V), and pharmaceutically acceptable salts thereof,

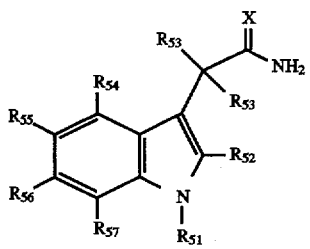 (V)

wherein;

X is oxygen;

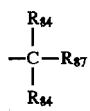

where, $R_{84}$ is hydrogen or $C_1$–$C_{10}$ alkyl, and $R_{87}$ is —(CH$_2$)$_m$-(phenyl) or —(CH$_2$)$_m$-(biphenyl), wherein m is 0 to 2 and the phenyl or biphenyl radicals are unsubstituted or substituted by halo, —CN, —CHO, —OH, nitro, phenyl, —SH, $C_1$–$C_{10}$ alkylthio, $C_1$–$C_{10}$ alkyl, $C_1$–$C_{10}$ alkoxyl, carboxyl, amino, hydroxyamino or a substituted or unsubstituted 5 to 8 membered heterocyclic ring;

$R_{52}$ is halo, methylthio, cyclopropyl, or $C_1$–$C_3$ alkyl;

each $R_{53}$ is hydrogen or halo;

$R_{54}$ and $R_{55}$ are each independently selected from (a) and (b) where;

(a) is hydrogen, and;

(b) is a group having the formula;

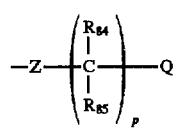

with the proviso that at least one of $R_{54}$ and $R_{55}$ must be selected from (b), and where;

$R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH— or —S—; and

Q is -5-tetrazolyl, —SO$_3$H,

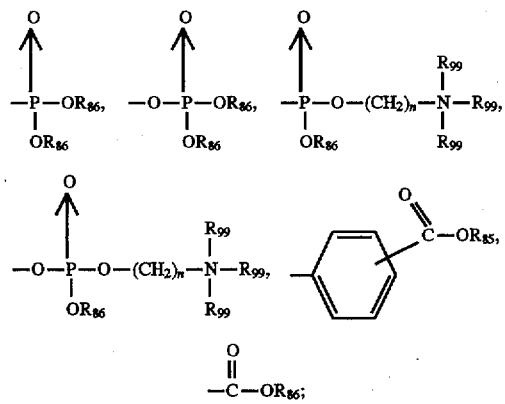

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

$R_{56}$, and $R_{57}$ are each independently hydrogen, $C_1$–$C_{10}$ alkyl, aryl, aralkyl, $C_1$–$C_{10}$ haloalkyl, $C_1$–$C_{10}$ alkoxy, $C_1$–$C_{10}$ haloalkoxy, phenoxy, halo, hydroxy, carboxyl, or a group having the formula;

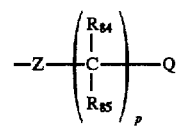

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is -5-tetrazolyl, —SO$_3$H,

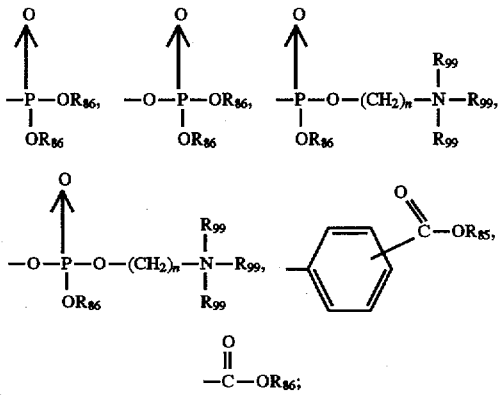

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

Illustrative of the novel compounds having utility in this invention are the following:

4-[[3-(2-Amino-2-oxoethyl)-2-chloro-1-(phenylmethyl)-1H-indole-5-yl]oxy]butanoic acid, a compound represented by the formula

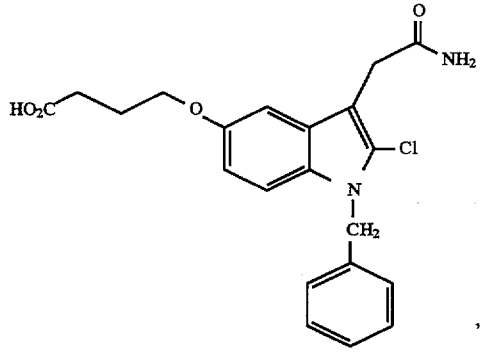

,

2-[[3-(2-Amino-2-oxoethyl)-2-methyl-1-(phenylmethyl)-1H-indol-4-yl]oxy]acetic acid, a compound represented by the formula

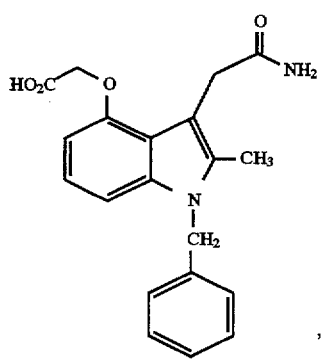

,

[3-[[3-(2-amino-2-oxoethyl)-2-methyl-1-(phenylmethyl)-1H-indol-5-yl]oxy]propyl] phosphonic acid, a compound represented by the formula

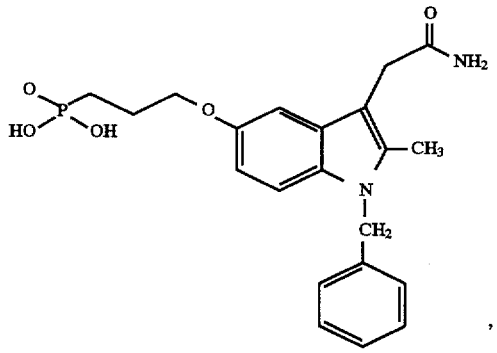

,

4-[[3-(2-Amino-2-oxoethyl)-2-bromo-1-(phenylmethyl)-1H-indol-5-yl]oxy]butanoic acid, a compound represented by the formula

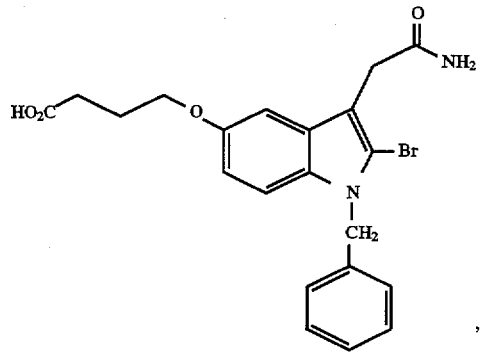

,

4-[[3-(2-Amino-2-oxoethyl)-2-(methylthio)-1-(phenylmethyl)-1H-indol-5-yl]oxy]butanoic acid, a compound represented by the formula

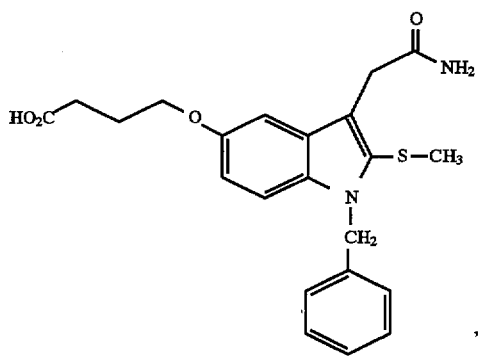

, 5-(4-Amino-4-oxobutoxy)-2-(methylthio)-1-(phenylmethyl)-1H-indole-3-acetamide, a compound represented by the formula

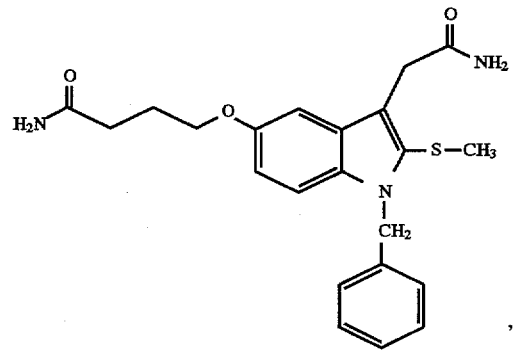

,

17

[4-[[3-(2-amino-2-oxoethyl)-2-ethyl-1-(phenylmethyl)-1-H-indol-5-yl]oxy]butanoic acid, a compound represented by the formula

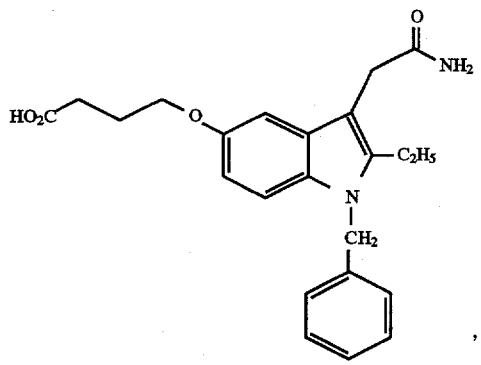

2-Ethyl-5-(4-hydrazino-4-oxobutoxy)-1-(phenylmethyl)-1H-indole-3-acetamide, a compound represented by the formula

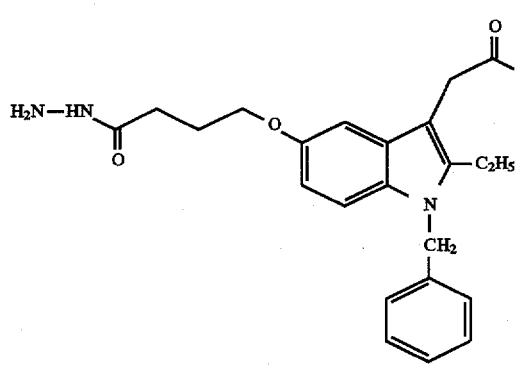

[3-[[3-(2-amino-2-oxoethyl)-2-ethyl-1-(phenylmethyl)-1H-indol-5-yl]oxy]propyl] phosphonic acid, a compound represented by the formula

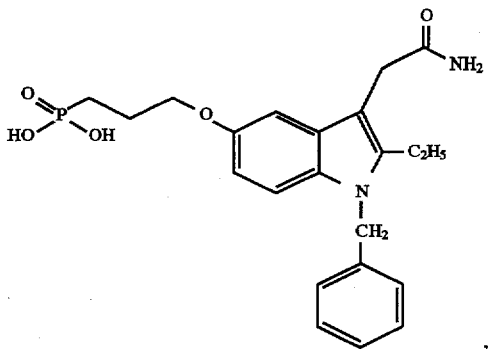

18

[3-[[3-(2-Amino-2-oxoethyl)-2-ethyl-1-(phenylmethyl)-1H-indol-5-yl]oxy]propyl] phosphonic acid monomethyl ester, a compound represented by the formula

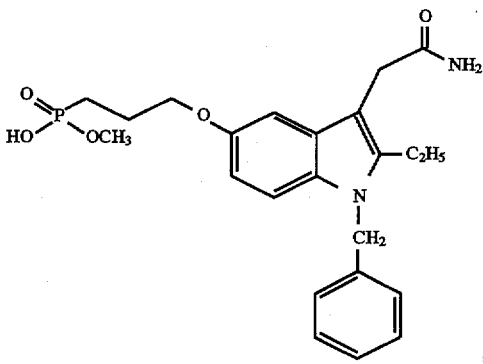

[3-[[3-(2-Amino-2-oxoethyl)-1-[(3-chlorophenyl)methyl]-2-ethyl-1H-indol-5-yl]oxy]propyl] phosphonic acid, a compound represented by the formula

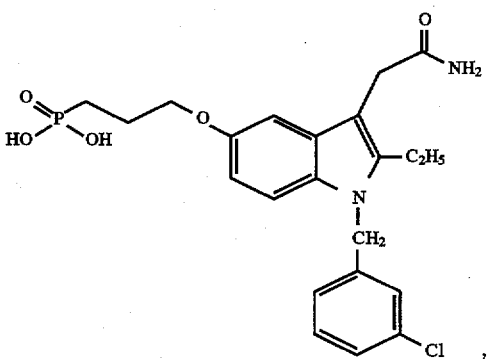

[[3Amino-2-oxoethyl)-1-[(3-chlorophenyl)methyl]-2-methyl-1H-indol-4-yl]oxy]methyl]acetic acid sodium salt, a compound represented by the formula

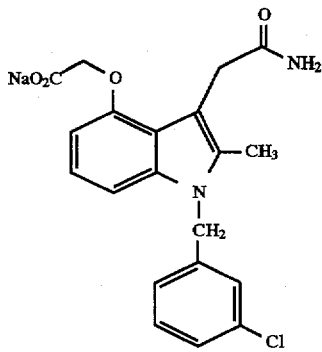

19

[[3-(2-Amino-2-oxoethyl)-1-([1,1'-biphenyl]-2-ylmethyl)-2-methyl-1H-indol-4-yl]oxy]acetic acid sodium salt, a compound represented by the formula

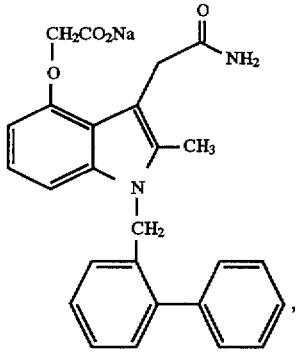

,

[[3-(2-Amino-2-oxoethyl)-2-ethyl-1-(phenylmethyl)-1H-indol-4-yl]oxy]acetic acid, a compound represented by the formula

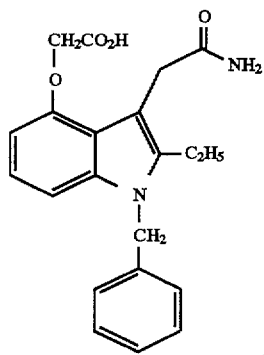

,

2-[[3-(2-Amino-2-oxoethyl)-1-[(3-chlorophenyl)methyl]-2-ethyl-1H-indol-4-yl]oxy]acetic acid, a compound represented by the formula

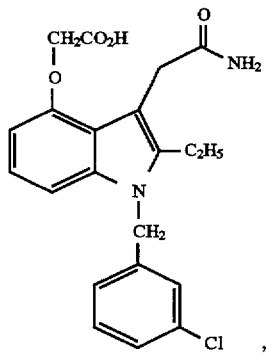

,

20

2-Cyclopropyl-5-hydroxy-1-(phenylmethyl)-1H-indole-3-acetamide, a compound represented by the formula

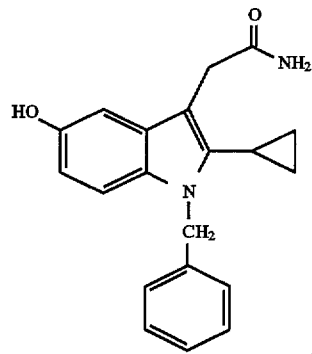

,

[3-[[3-(2-Amino-2-oxoethyl)-2-cyclopropyl-1-(phenylmethyl)-1H-indol-5-yl]oxy]propyl]phosphonic acid, a compound represented by the formula

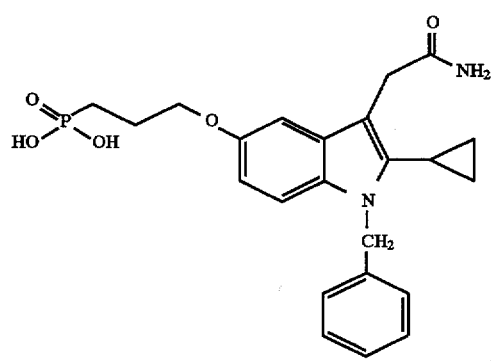

,

[3-[[3-(2-Amino-1-oxoethyl)-1-(phenylmethyl)-1H-indol-5-yl]oxy]propyl]phosphonic acid, a compound represented by the formula

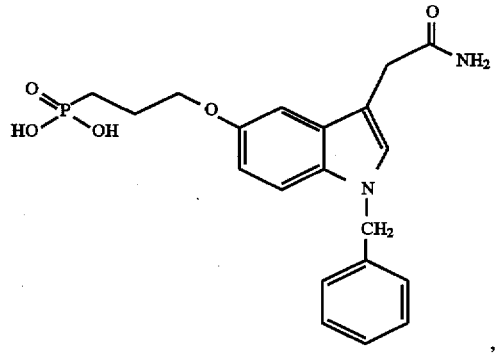

,

21

4-[[3-(2-Amino-2-oxoethyl)-1-(phenylmethyl)-1H-indol-5-yl]oxy]butanoic acid, a compound represented by the formula

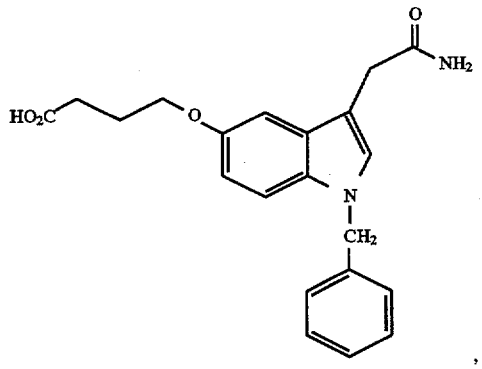

,

3-[4-[[3-(2-Amino-2-oxoethyl)-2-ethyl-1-(phenylmethyl)-1H-indol-5-yl]oxy]propane]sulfonic acid, a compound represented by the formula

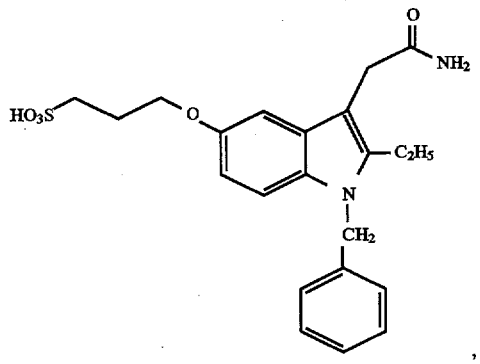

,

3-[[3-(2-Amino-2-oxoethyl)-2-bromo-1-(phenylmethyl)-1H-indol-5-yl]oxy]propyl] phosphonic acid monomethyl ester, a compound represented by the formula

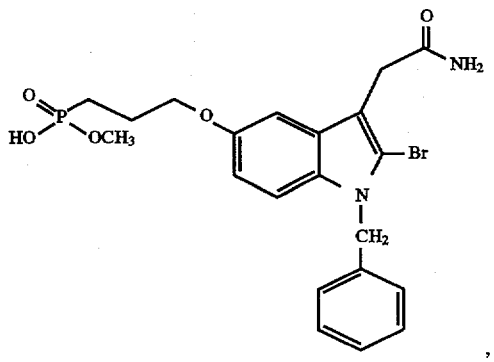

,

22

2-Bromo-6-chloro-5-methoxy-1-(phenylmethyl)-H-indole-3-acetamide, a compound represented by the formula

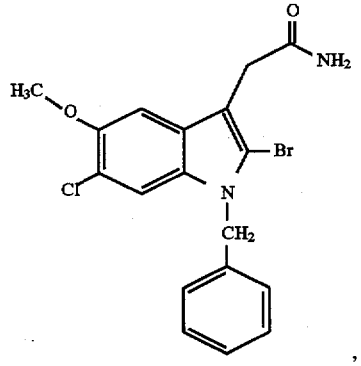

,

2-Bromo-6-chloro-5-hydroxy-1-(phenylmethyl)-H-indole-3-acetamide, a compound represented by the formula

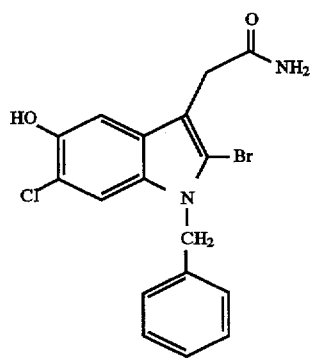

,

4-[[3-(2-Amino-2-oxoethyl)-2-bromo-6-chloro-1-(phenylmethyl)-1H-indol-5-yl]oxy]butanoic acid, a compound represented by the formula

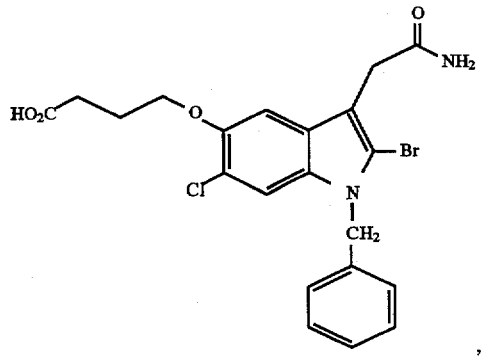

,

3-[4-[[3-(2-Amino-2-oxoethyl)-6-chloro-1-(phenylmethyl)-1H-indol-5-yl]oxy]propyl] phosphonic acid, a compound represented by the formula

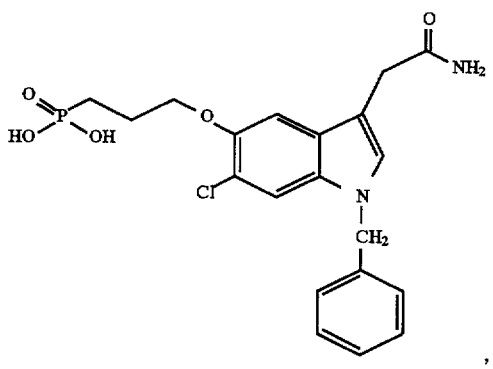

,

4-Allyl-2-ethyl-5-hydroxy-1-(phenylmethyl)-1H-indole-acetamide, a compound represented by the formula

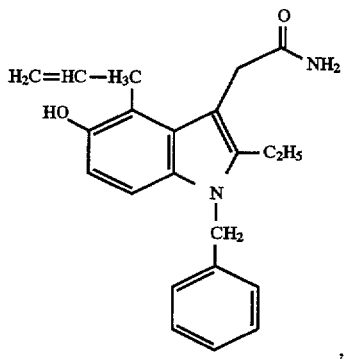

,

2-[[[3-(2-Amino-2-oxoethyl)-2-methyl-1-(phenylmethyl)-1H-indol-5-yl]oxy]methyl]benzoic acid, a compound represented by the formula

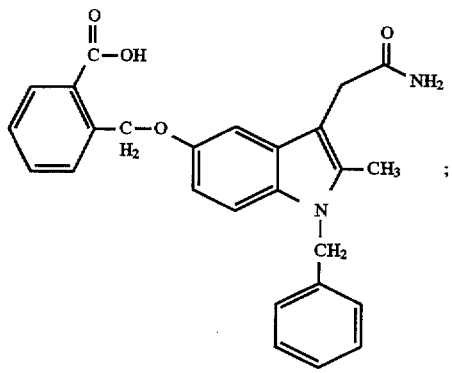

;

and pharmaceutically acceptable salts of each of the above named compounds.

The salts of the above 1H-indole-3-acetamide compounds of formulae A, I, II, III, IV, V, VI and the above named specific compounds are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases (e.g., derived from glucosamine, morpholine, choline, or diethylamine) of sufficient basicity to form salts with the compounds of this invention see, for example, S. M. Berge, et al., "Pharmaceutical Salts," J. Phar. Sci., 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmirate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters.

Synthesis Methods

The synthesis of the 1H-indole-3-acetamides of structure (I) can be accomplished by known methods. Procedures useful for the syntheses of the compounds of this invention are outlined in the following reaction schemes:

In the first scheme, the 1H-indole-3-acetic acid esters, II, can be readily form IV may be carried out at the reflux temperature of the solvent for a period of 1 to 24 hours. The acetic acid hydrazides, IV, are hydrogenated to give the acetamides, I, by heating with Raney nickel in ethanol (method c). The

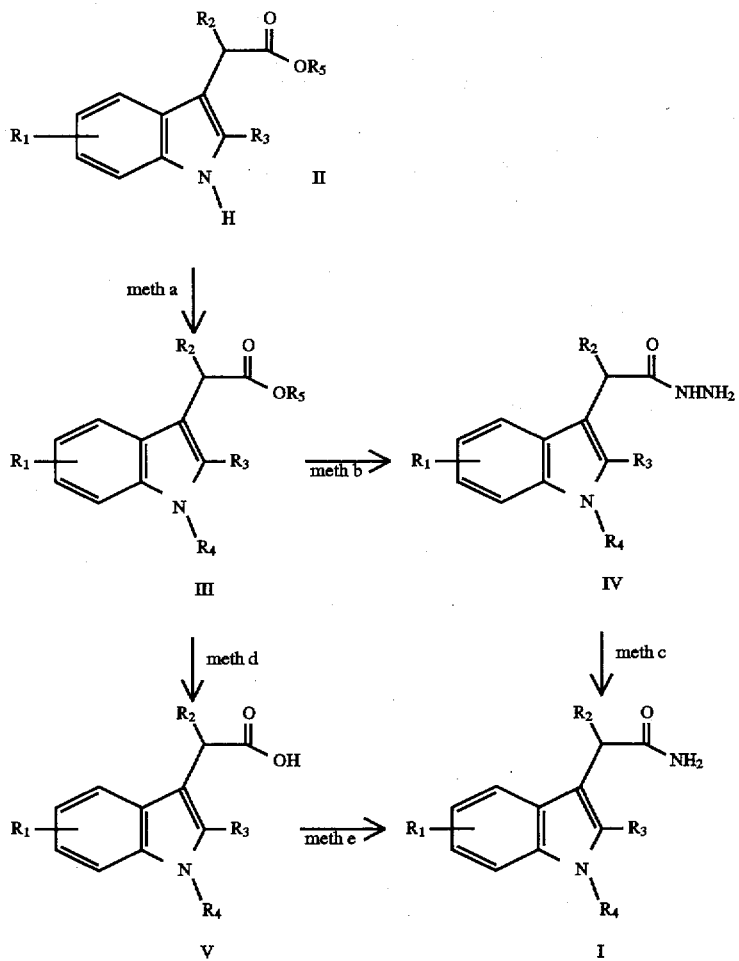

Scheme 1.

alkylated by an alkyl halide or arylalkyl halide in a solvent such as N,N-dimethylformamide (DMF) in the presence of a base (method a) to give intermediate 1-alkyl-1H-indole-3-acetic acid esters, III. Bases such as potassium t-butoxide and sodium hydride are useful. It is advantageous to react the indole, II, with the base to first form the salt of II and then add alkylating agent. Treatment of the 1-alkyl-1H-indole-3-acetic acid esters, III, with hydrazine or hydrazine hydrate in ethanol (method b) gives the desired 1-alkyl-1H-indole-3-acetic acid hydrazides, IV. This condensation to intermediate acetic acid esters, III, can be first hydrolyzed to the acetic acid derivatives, V (method d), which on treatment with an alkyl chloroformate followed by anhydrous ammonia, also give amides, I (method e).

The intermediate 1H-indole-3-acetic acid esters, II, can be obtained from several synthetic routes as illustrated in Scheme 2. The 1H-indole-3-acetic acids, VI, are readily esterified in an alcohol such as methanol in the

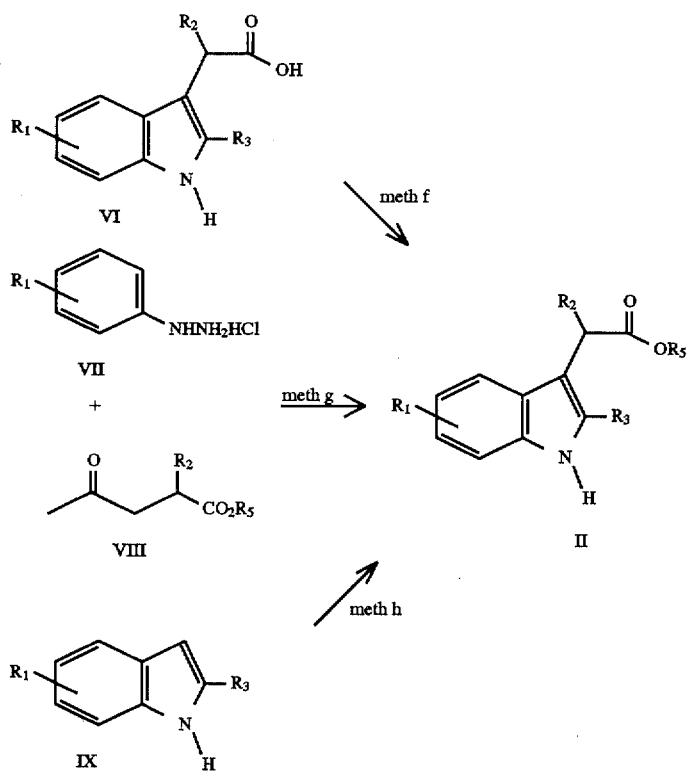

presence of a strong acid, such as sulfuric acid (method f) to give II. Substituted phenylhydrazines, VII, can be reacted with levulinic acid derivatives, VIII, by the well known Fisher-indole synthesis (method g) to give (see, ref. B. Carlin and E. E. Fisher, J. Am. Chem. Soc., 1948, 70, 3421) directly the indole, II. Ethanol as solvent at reflux temperature and hydrogen chloride as the acid catalyst is generally used. Indoles that are unsubstituted at the 3position, IX, can be alkylated by first forming the zinc salts of IX and treating these salts with alkyl 2-bromoalkanoate (see, ref. Yoshihiko Ito, Hideaki Sato, Masahiro Murakami, J. Org. Chem., 1991, 56, 4864–4867) in (method h) to give II. The zinc salts of IX can be prepared by reacting the indoles IX first with n-butyl lithium using tetrahydrofuran as solvent and then with zinc chloride in ether. The solvent for this reaction is usually changed after the zinc salt formation to toluene by removing the ether and THF solvent at reduced pressure and adding toluene.

For additional substituted derivatives of IX, the reactions in Scheme 3 are (see, ref. Robin D. Clark, Joseph M. Muchowski, Lawrence E. Fisher, Lee A. Flippin, David B. Repke, Michel Souchet, Synthesis, 1991, 871–878) employed.

Scheme 3.

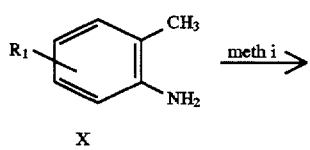

Ortho-methylanilines, X, are treated with di-tert-butyl dicarbonate in THF at reflux temperature (method i) to give the N-tert-butoxycarbonylanilines, XI. The dianion of XI is formed in THF by treatment with two equivalents of sec-butyl lithium and reacts with one equivalent of an N-methoxy-N-methylalkanoic acid amide to give (method j) the aryl ketone, XII. These ketones on treatment with trifluoroacetic acid (method k) are both cyclized and deprotected on the nitrogen to give the indoles, IX. Indoles of type IX that are substituted at the 5-position with nitro, are (see, ref. Wayland E. Noland, Lowell R. Smith, and Donald C. Johnson, J. Org. Chem., 1963, 28, 2262–2266) obtained by adding sodium nitrate to the appropriate indole previously dissolved in sulfuric acid (method l).

Scheme 4.

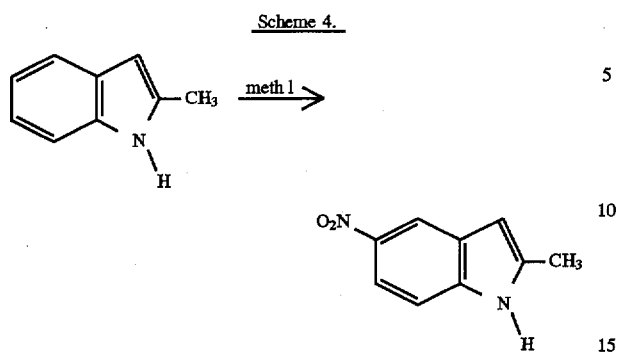

To obtain derivatives of I where the $R_1$ substituent is 5-hydroxy or an alkoxy other than methoxy, the methods described in scheme 5 are used. The 5-methoxy indole-3-acetic acids are readily demethylated (method m) by treatment with $BBr_3$ (see, ref. Tsung-Ying Shen and Charles A. Winter, Adv. Drug Res., 1977, 12, 176) to give the 5-hydroxy indole, V, which is elaborated, by methods previously

Scheme 5.

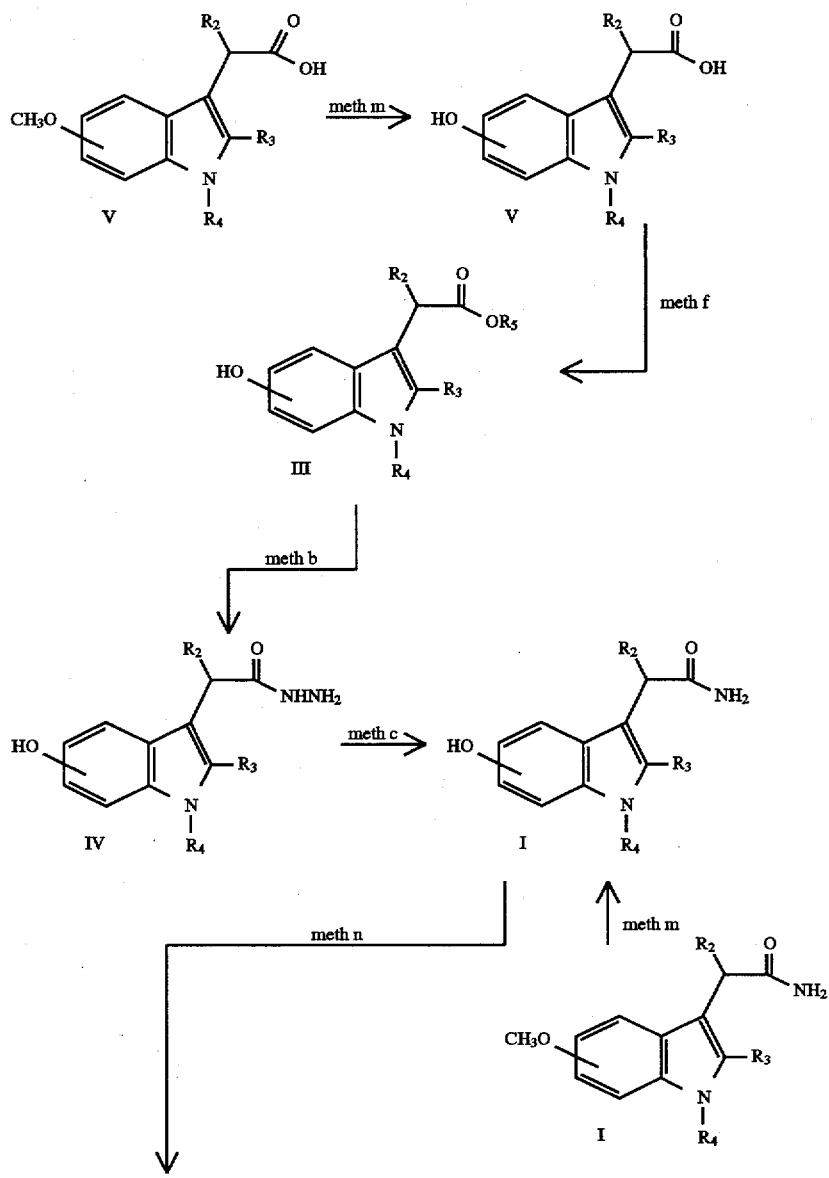

-continued
Scheme 5.

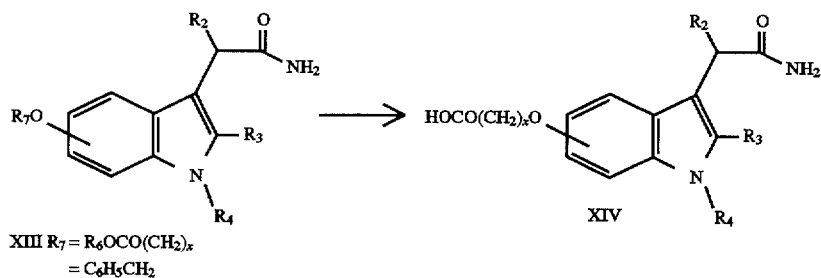

XIII R₇ = R₆OCO(CH₂)ₓ
      = C₆H₅CH₂ described, to I, where $R_1$ is hydroxy. 1H-indole-3-acetamides, where $R_1$ is 4- or 5- or 6-methoxy can be also directly demethylated to I ($R_1$=hydroxy) by method m. These compounds can then be alkylated to give compounds of structure XIII. When alkyl acrylates are used, derivatives of XIII are obtained where x is equal to 2. Bromo acetates and 4-bromo-butyrates give esters of structure XIII where x is 1 and 3, respectively. Use of benzyl halide gives the phenylmethyl derivative. All of the compounds where $R_7$ contains an ester group can be converted to their carboxylic acid equivalents, XIV.

The 2-chloro-1H-indole-3-acetamides are best prepared by the reactions outlined in Scheme 6. The 1-dimethylamino substituent on XV is used to direct the lithiation by sec-butyl lithium to the 2 position. This on treatment with benzenesulfonyl chloride gives XVI, which on treatment with aqueous HCl, loses the dimethylamino group to give 2-chloro-5-methoxy-1H-indole. Reactions of this indole using methods previously described gives the 2-chloro esters, III. This ester may be converted to the 2-chloro amide, I, using the reagent, $(CH_3)_2AlNH_2$ (method q). These may be O-demethylated and the phenolic intermediate realkylated as described in Scheme 5 to give the compounds of structure XIII, where $R_3$ is chloro.

Scheme 6.

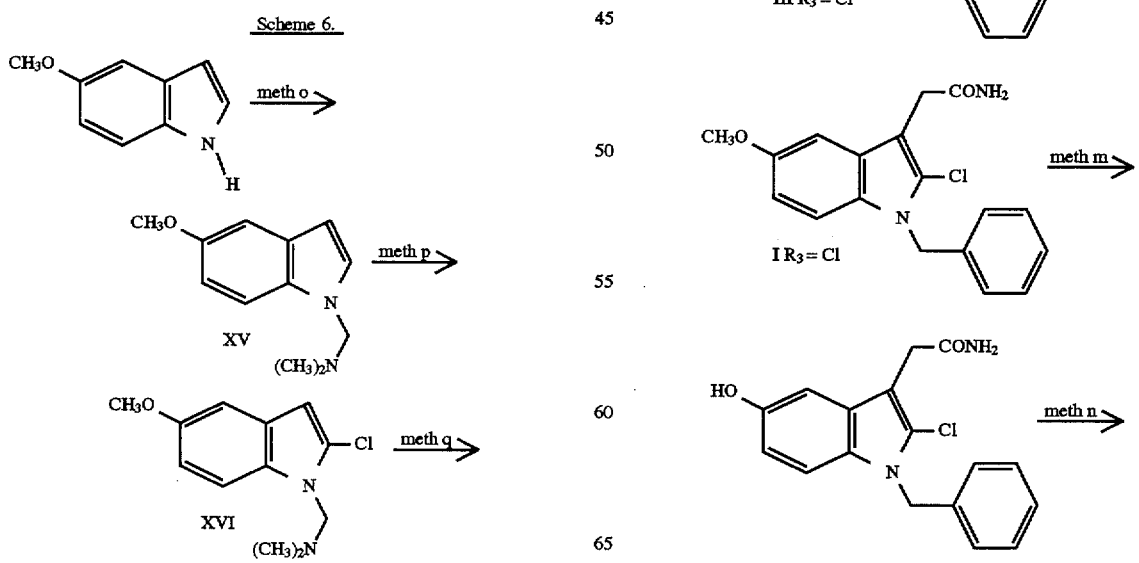

-continued
Scheme 6.

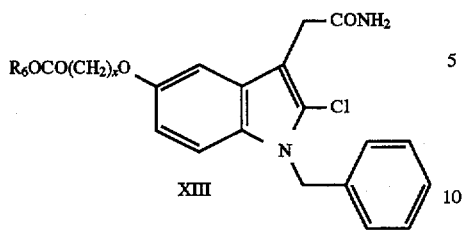

XIII

-continued
Scheme 7.

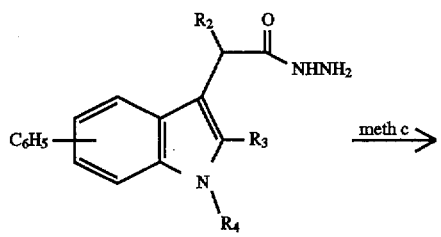

The intermediate 1H-indole-3-acetic acid esters, III, where $R_3$ is bromo are made by reacting the ester, III, where $R_3$ is hydrogen, with N-bromosuccinimide(method s). In a similar fashion, methanesulfenyl chloride gives the 3-methylthio indole, III, $R_3=CH_3S$.

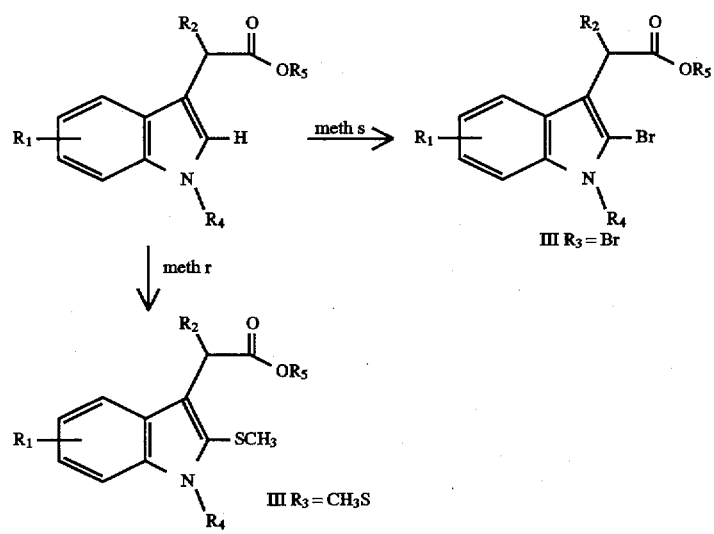

Compounds of structure I where $R_1$ is phenyl, are made by phenylation (see, ref. N. Miyaura, T. Yamag, A. Suzuk: Snyth. Commun. 1981 11, p. 513–519) of the intermediates where $R_1$ is Br (method t). This phenylation can be carried Scheme 7.

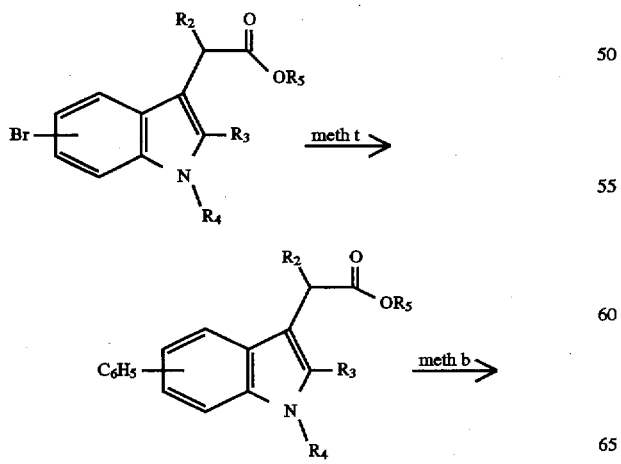

-continued
Scheme 7.

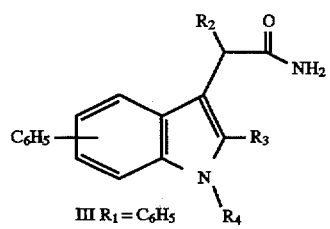

III $R_1 = C_6H_5$ out on any of the appropriate bromo substituted intermediates. The 1H-indole-3-acetamide, I, where $R_1$ is aminocarbonyl can be made through the appropriate diester. XVII, which is converted by previously described methods to the final diamide, I

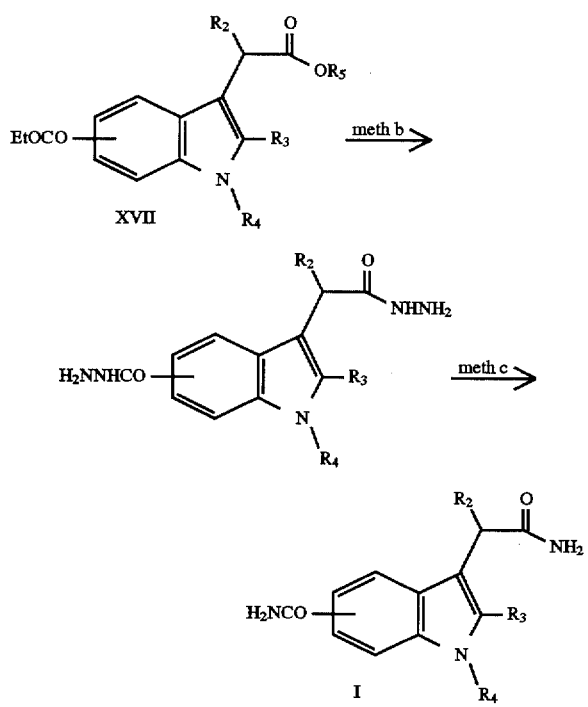

The amides, I, where the $R_1$ substitutents contain nitrogen, as well as the compounds where substitution on the amino group contains esters or carboxylic acids, such as XXI and XXII, may be made by the procedures outlined in Scheme 8. 2-Methyl-5-nitro-1H-indole is first benzylated to give the N-substituted derivative, XVIII. Treatment of this indole with oxalyl chloride (method u) followed by the addition of gaseous ammonia gives the oxalamide, XIX. Stepwise reduction of this compound is carried out. The glycolic acid amide, XX, is obtained by treatment of XVIII with $NaBH_4$ (method v). Reduction of this intermediate with triethylsilane (method w) in trifluoroacetic acid results in the acetamide, I, ($R_1=O_2N$). The nitro function may be reduced catalytically (method x) to give the 5-amino amide (I, $R_1=NH_2$). Treatment of this amino intermediate with methyl acrylate gives the ester amide XXI (some of the N,N-disubstituted derivative is also obtained in this reaction). This ester may be hydrolyzed with sodium hydroxide to give carboxylic acid amide, XXII. The same ester intermediate, XXI, is reacted with hydrazine to give the hydrazinocarbonyl derivative, XXIII.

6-Methoxy-2-methyl-1H-indole is converted to 6-methoxy-2-methyl-1H-indole-3-actamides by the sequence of reactions outlined in the first 4 steps of Scheme 8.

Scheme 8.

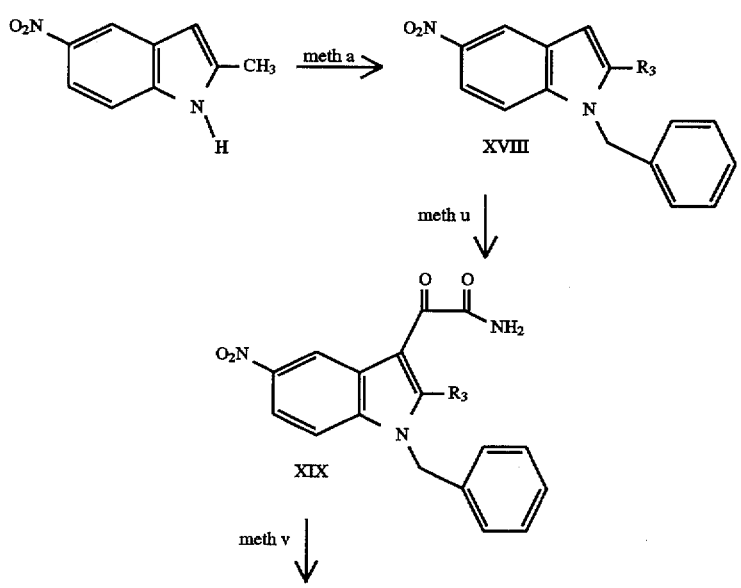

-continued
Scheme 8.

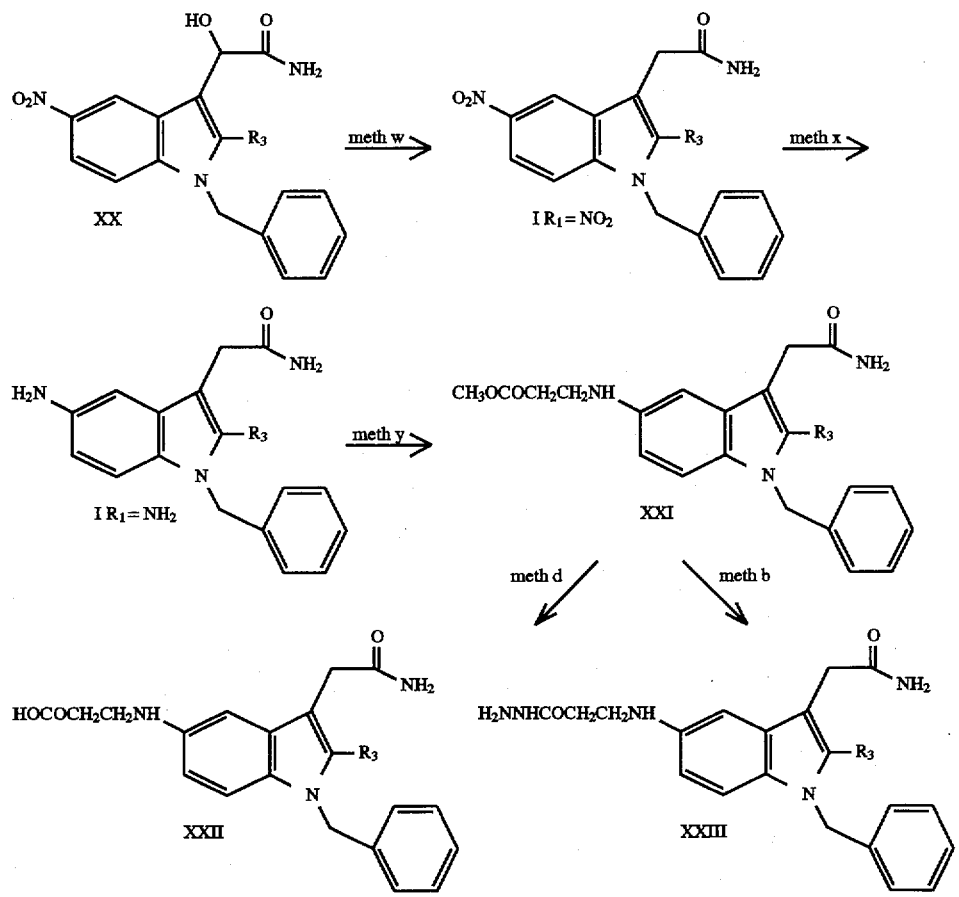

Described below are examples of the present invention which are provided only for illustrative purposes. They are not intended to limit the scope of the present invention in any way as numerous embodiments within the scope of the claims will be apparent to those of ordinary skill in the art.

EXAMPLES

Example 1

Preparation of 2,6-Dimethyl-1-(phenylmethyl)-1H-indole-3-acetamide

A. N-tert-Butoxycarbonyl-2,5-dimethylaniline. A solution of 2,5-dimethylaniline (24.2 g, 0.2 mol) and 50.0 g (0.229 mol) of di-tert-butyl dicarbonate in 200 ml of tetrahydrofuran was heated slowly to reflux and reflux maintained for 2 hours. After cooling, the reaction mixture was concentrated at reduced pressure and the residue dissolved in EtOAc. The EtOAc solution was washed with 1N citric acid solution, dried over $Na_2SO_4$, and concentrated at reduced pressure. Crystallization of the residue from hexane gave 24.0 g (54% yield) of N-tert-butoxycarbonyl-2,5-dimethylaniline melting at 103°–104° C.

Analyses: Calc'd for $C_{13}H_{19}NO_2$: C, 70.56; H, 8.65; N, 6.32. Found: C, 70.28; H, 8.51; N, 6.60.

B. 2,6-Dimethyl-1H-indole. A solution of 1.3M sec-butyl lithium/cyclohexane (81.0 ml, 0.105 mol) was added slowly to 11.05 g (0.05 mol) of N-tert-butoxycarbonyl-4-ethoxy-2-methylaniline in 150 ml of THF while keeping the temperature below −40° C. with a dry ice-ethanol bath. After 0.25 hours, 7.21 g (0.07 mol) of N-methoxy-N-methylacetamide in an equal volume of THF was added dropwise. The reaction mixture was stirred for 1 hour, the cooling bath removed and stirred an additional one hour. It was then poured into a mixture of 500 ml of ether and 500 ml of 1N HCl. The organic layer was separated, washed with water and dried over $Na_2SO_4$. After removing the solvent there remained 12.5 g of crude 1-(2-tert-butoxycarbonylamino-4-methylphenyl)-2-propanone. This material and 15 g of trifluoroacetic acid in 250 ml of $CH_2Cl_2$ was stirred at room temperature for 16 hours. The mixture was washed twice with water, a saturated $Na_2CO_3$ solution and dried over $Na_2SO_4$. After removing the solvent, the produce was chromatographed on silica eluting with toluene to give 3.2 g (44% yield) of 2,6-dimethyl-1H-indole melting at 74°–76° C.

Analyses: Calc'd for $C_{10}H_{11}N$: C, 82.72; H, 7.64; N, 9.65. Found: C, 82.47; H, 7.34; N, 9.92.

C. 2,6-Dimethyl-1H-indole-3-acetic acid methyl ester. To a cooled solution of 2.9 g (0.02 mol) of 2,6-dimethyl-1H-indole in 40 ml of THF was added 12.5 mL (0.02 mol) of a 1.6M solution of n-butyl lithium in hexane keeping the temperature below 10° C. with an ice-ethanol bath. After 0.25 hours, 20.0 ml (0.0277 mol) of 1M solution of $ZnCl_2$ in ether was added. The cooling bath was removed and the mixture stirred for 2 hours, then concentrated at reduced pressure to a wax which was dissolved in 40 ml of toluene. To this solution was added 1.89 ml (0.02 mol) of methyl 2-bromoacetate, the mixture was stirred 24 hours and poured into 100 ml of 1N HCl and 100 ml of EtOAc. The organic layer was washed twice with water, dried ($Na_2SO_4$), and concentrated at reduced pressure. The residue was chromatographed on silica and eluted with 10% EtOAc/toluene to give 3.17 g (73%) of 2,6-dimethyl-1H-indole-3-acetic acid methyl ester as an oil.

Analyses: Calc'd for $C_{13}H_{15}NO_2$: C, 71.87; H, 6.96; N, 6.45. Found: C, 71.61; H, 6.95; N, 6.30.

D. 2,6-Dimethyl-1-(phenylmethyl)-1H-indole-3-acetic acid methyl ester. Potassium t-butoxide (0.975 g, 0.0087 mol) was added to 1.89 g (0.0087 mol) of 2,6-dimethyl-1H-indole-3-acetic acid methyl ester in 25 ml of DMF, the mixture was stirred for 0.25 hours, 1.0 ml of benzyl chloride was added and the mixture stirred for 72 hours. After diluting with water, the mixture was extracted with EtOAc, The EtOAc solution was washed four times with water and dried over $Na_2SO_4$. The solvent was removed at reduced pressure and the residue chromatographed on silica eluting with toluene to give 1.76 g (66% yield) of 2,6-dimethyl-1-(phenylmethyl)-1H-indole-3-acetic acid methyl ester as an oil.

Analyses: Calc'd for $C_{20}H_{21}NO_2$: C, 73.15; H, 6.89; N, 4.56. Found: C, 78.18; H, 7.10; N, 4.53.

E. 2,6-Dimethyl-1-(phenylmethyl)-1H-indole-3-acetic acid. A solution of 1.7 g (0.0055 mol) of 2,6-dimethyl-1-(phenylmethyl)-1H-indole-3-acetic acid methyl ester and 2 ml of 5N NaOH in 50 ml of MeOH was heated to maintain reflux for 3 h, diluted with water and made acidic with 5N HCl solution. The mixture was extracted with EtOAc, the EtOAc solution dried over NaSO4 and concentrated at reduced pressure. The residue was crystallized from toluene to give 0.85 g (58% yield) of 2,6-dimethyl-1-(phenylmethyl)-1H-indole-3-acetic acid, mp, 179°–180° C.

Analyses: Calc'd for $C_{19}H_{19}NO_2$: C, 77.79; H, 6.53; N, 4.77. Found: C, 78.01; H, 6.60; N, 4.80.

F. 2,6-Dimethyl-1-(phenylmethyl)-1H-indole-3-acetamide. A solution of 0.48 g (1.64 mmol) of 2,6-dimethyl-1-(phenylmethyl)-1H-indole-3-acetic acid in 25 ml of tetrahydrofuran(THF) was cooled with an ice-water bath, 0.45 ml of triethylamine was added followed by 0.13 ml (1.7 mmol) of methyl chloroformate. After 0.5 hour, gaseous $NH_3$ was bubbled into the reaction mixture for 0.5 hour, the cooling bath removed and the mixture stirred for 2 hours. It was then poured into water and extracted with EtOAc, the EtOAc solution washed with a $Na_2CO_3$ solution, dried ($Na_2SO_4$), and concentrated at reduced pressure. The residue was crystallized from MeOH/water, to give 0.19 g (39% yield) of 2,6-dimethyl-1-(phenylmethyl)-1H-indole-3-acetamide, mp, 160°–163° C.

Analyses: Calc'd for $C_{19}H_{20}N_2O$: C, 78.05; H, 6.89; N, 9.58. Found: C, 78.31; H, 6.97; N, 9.31.

Example 2

Preparation of 5-Hydroxy-1-methyl-1-(phenylmethyl)-1H-indole-3-acetamide

A. 5-Methoxy-2-methyl-1H-indole-3-acetic acid methyl ester. A solution of 12.2 g (0.0557 mol) of 5-methoxy-2-methyl-1H-indole-3-acetic acid in 150 of MeOH and 1 ml of sulfuric acid was heated to maintain reflux for 15 hours. After cooling, the mixture was diluted with a sodium bicarbonate solution and extracted with EtOAc. The EtOAc solution was washed with a saturated NaCl solution and dried ($Na_2SO_4$). The solvent was removed at reduced pressure to give 13 g of crude 5-methoxy-2-methyl-1H-indole-3-acetic acid methyl ester.

B. 5-Methoxy-2-methyl-1-(phenylmethyl)-1H-indole-3-acetic acid. The crude 5-methoxy-2-methyl-1H-indole-3-acetic acid methyl ester from A (56 mmol) was dissolved in 250 mL of DMF and approximately 10 ml of THF and 2.5 g (62 mmol) of 60% NaH/mineral oil added. After 0.5 hour, 8 mL (67 mmol) of benzyl bromide was added and the mixture stirred for 0.75 hours, diluted with water and extracted with EtOAc. The product was chromatographed on silica (20% ether/hexane→50% ether/hexane) to give 10.1 g of a mixture of 5-methoxy-2-methyl-1-(phenylmethyl)-1H-indole-3-acetic acid methyl and ethyl esters. This mixture was dissolved in 200 mL of EtOH and 20 mL of 5N NaOH and heated to maintain reflux for 20.75 hours. After cooling the mixture was made acidic with 5N HCl and extracted with EtOAc. The EtOAc solution was washed with NaCl, dried ($Na_2SO_4$), and concentrated at reduced pressure to give 7.9 g (46% yield) of crude 5-methoxy-2-methyl-1-(phenylmethyl)-1H-indole-3-acetic acid.

C. 5-Hydroxy-2-methyl-1-(phenylmethyl)-1H-indole-3-acetic acid methyl ester. Three mL (30 mmol) of $BBr_3$ was added to 3.1 g (10 mmol) of 5-methoxy-2-methyl-1-(phenylmethyl)-1H-indole-3-acetic acid in 250 mL of $CH_2Cl_2$ and the mixture stirred for 17 hours. After stirring with 1N HCl, some EtOH was added, the organic layer separated, washed with a saturated NaCl solution, dried and concentrated at reduced pressure to give 2.95 g (100% yield) of crude 5-hydroxy-2-methyl-1-(phenylmethyl)-1H-indole-3-acetic acid. A methanol solution of 1.7 g of the material was treated with sulfuric acid as described in Part A to give after silica gel chromatography (30% ether/hexane→60% ether/hexane) 1.5 g of 5-hydroxy-2-methyl-1-(phenylmethyl)-1H-indole-3-acetic acid methyl ester.

D. 5-Hydroxy-2-methyl-1-(phenylmethyl)-1H-indole-3-acetamide. A solution of 750 mg (2.4 mmol) of 5-hydroxy-2-methyl-1-(phenylmethyl)-1H-indole-3-acetic acid methyl ester and 2 mL of hydrazine in 75 mL of ethanol was heated to maintain reflux for 72 hours. After cooling, 2 g of Raney nickel was added cautiously and the mixture heated at reflux for 4 hours. After cooling, the solvent was decanted off and the solids washed with EtOAc by decanting. The combined solvents where filtered through celite and concentrated at reduced pressure. The residue was crystallized from EtOH to give 570 mg (80% yield) of 5-hydroxy-2-methyl-1-(phenylmethyl)-1H-indole-3-acetamide, mp, 185°–187° C.

Analyses: Calc'd for $C_{18}H_{18}N_2O_2$: C, 73.45; H, 6.16; N, 9.52. Found: C, 73.23; H, 6.32; N, 9.69.

Example 3

Preparation of 5-Methoxy-1-(phenylmethyl)-1H-indole-3-acetamide

A. 5-Methoxy-1H-indole-3-acetic acid ethyl ester. As described in Example 1, Part C, 29.44 g (0.0.2 mol) of 5-methoxy-1H-indole was treated with 125 mL (0.2 mol) of 1.6M n-butyl lithium in hexane, 200 mL (0.2 mol) of 1M $ZnCl_2$ in ether, and 22.2 mL (0.2 mol) of ethyl 2-bromoacetate to give after chromatography on silica (eluted with 5% EtOAc/toluene) 20 g (43% yield) of 5-methoxy-1H-indole-3-acetic acid ethyl ester, as an oil.

Analyses: Calc'd for $C_{13}H_{15}NO_3$: C, 66.94; H, 6.48; N, 6.01. Found: C, 66.72; H, 6.53; N, 5.91.

B. 5-Methoxy-1-(phenylmethyl)-1H-indole-3-acetic acid ethyl ester. Using the procedure described in Example 1 Part D, 3.15 g (0.0135 mol) of 5-methoxy-1H-indole-3-acetic acid ethyl ester was reacted with 1.51 g (0.0135 mol) of potassium t-butoxide and 1.55 mL (0.0135 mol) of benzyl chloride to give after silica chromatography (gradient, toluene→5% EtOAc/toluene) 3.6 g (83%) of 5-methoxy-1-(phenylmethyl)-1H-indole-3-acetic acid ethyl ester as an oil.

Analyses: Calc'd for $C_{20}H_{21}NO_3$: C, 74.28; H, 6.55; N, 4.33. Found: C, 75.53; H, 6.67; N, 4.08.

C. 5-Methoxy-1-(phenylmethyl)-1H-indole-3-acetic acid hydrazide. A solution of 1.4 g (4.33 mmol) of 5-methoxy-1-(phenylmethyl)-1H-indole-3-acetic acid ethyl ester and 10 mL of hydrazine in 75 mL of EtOH was heated to maintain reflux for 16 hours. On cooling of the reaction mixture a precipitate formed that was filtered to give 1.33 g (93% yield) of 5-methoxy-1-(phenylmethyl)-1H-indole-3-acetic acid hydrazide, mp 143°–144° C.

Analyses: Calc'd for $C_{18}H_{19}N_3O_2$: C, 69.88; H, 6.19; N, 13.58. Found: C, 69.91 H, 6.19; N, 13.37.

D. 5-Methoxy-1-(phenylmethyl)-1H-indole-3-acetamide. One gram of Raney nickel was added to 790 mg (2.4 mmol) of 5-methoxy-1-(phenylmethyl)-1H-indole-3-acetic acid hydrazide in 120 mL of EtOH and the mixture heated at reflux for 2 hours. After filtering off the catalyst, the filtrate was concentrated at reduced pressure and the residue triturated with ether to give 675 mg (89% yield) of 5-methoxy-1-(phenylmethyl)-1H-indole-3-acetamide, mp, 156°–158° C.

Analyses: Calc'd for $C_{18}H_{18}N_2O_2$: C, 73.45; H, 6.16; N, 9.52. Found: C, 70.18; H, 5.96; N, 8.93.

Example 4

Preparation of 1-Cyclohexylmethyl-5-methoxy-2-methyl-1H-indole-3-acetamide

A. 5-Methoxy-2-methyl-1H-indole-3-acetic acid ethyl ester. Dry hydrogen chloride was bubbled into a solution of 27.95 g (0.16 mol) of 4-methoxyphenylhydrazine hydrochloride and 19.72 g (0.17 mol) of levulinic acid in 500 mL of ethanol for 0.5 hours while cooling with an ice-water bath. The bath was removed and the reaction was slowly heated to reflux and reflux maintained for 20 hours. After cooling the mixture was poured into water and extracted with EtOAc. The EtOAc solution was washed with a sodium bicarbonate solution and dried over $Na_2SO_4$. After removing the solvent at reduced pressure, the residue was chromatographed over silica eluting with 5% EtOAc/toluene to give 14.2 g (36% yield) of 5-methoxy-2-methyl-1H-indole-3-acetic acid ethyl ester, mp, 38°–40° C.

Analyses: Calc'd for $C_{14}H_{17}NO_3$: C, 67.99; H, 6.93; N, 5.66. Found: C, 68.24 H, 6.88; N, 5.75.

B. 1-Cyclohexylmethyl-5-methoxy-2-methyl-1H-indole-3-acetic acid ethyl ester. Using the procedure described in Example 1 Part D, 4.7 g (0.19 mol) of 5-methoxy-1H-indole-3-acetic acid ethyl ester was reacted with 2.13 g (0.019 mol) of potassium t-butoxide and 2.65 mL (0.019 mol) of cyclohexylmethyl bromide to give after silica chromatography (gradient, toluene→5% EtOAc/toluene) 3.16 g (48%) of 1-cyclohexylmethyl-5-methoxy-2-methyl-1H-indole-3-acetic acid ethyl ester as an oil.

Analyses: Calc'd for $C_{21}H_{29}NO_3$: C, 73.44; H, 8.51; N, 4.08. Found: C, 73.68; H, 8.64; N, 4.14.

C. 1-Cyclohexylmethyl-5-methoxy-2-methyl-1H-indole-3-acetic acid. Using the method described in Example 1, Part E, 3.1 g (9.0 mmol) of 1-cyclohexylmethyl-5-methoxy-2-methyl-1H-indole-3-acetic acid ethyl ester and 5 mL of 5N NaOH were reacted in 50 mL of EtOH to give on workup, 2.1 g (74% yield) of 1-cyclohexylmethyl-5-methoxy-2-methyl-1H-indole-3-acetic acid melting at 173°–175° C. after crystallization from toluene.

Analyses: Calc'd for $C_{19}H_{25}NO_3$: C, 72.35; H, 7.99; N, 4.44. Found: C, 72.64; H, 8.00; N, 4.52.

D. 1-Cyclohexylmethyl-5-methoxy-2-methyl-1H-indole-3-acetamide. A solution of 0.63 g (2.0 mmol) 1-cyclohexylmethyl-5-methoxy-2-methyl-1H-indole-3-acetic acid and 0.56 mL (4 mmol) of triethylamine in 25 mL of tetrahydrofuran (THF) was reacted with 0.162 mL (2.1 mmol) of methyl chloroformate and then treated with gaseous $NH_3$ as described in Example 1, Part F, to give 0.3 g (48% yield) of 1-cyclohexylmethyl-5-methoxy-2-methyl-1H-indole-3-acetamide, mp, 125°–126° C.

Analyses: Calc'd for $C_{19}H_{26}N_2O_2$: C, 72.58; H, 8.33; N, 8.91. Found: C, 72.57; H, 8.35; N, 8.81.

Example 5

Preparation of 5-Methoxy-2-methyl-1-(phenylmethyl)-1H-indole-3-acetamide

A. 5-Methoxy-2-methyl-1-(phenylmethyl)-1H-indole-3-acetic acid ethyl ester. Using the procedure described in Example 1, Part D, 4.07 g (0.0165 mol) of 5-methoxy-2-methyl-1H-indole-3-acetic acid ethyl ester (Example 4, Part A) was reacted with 1.85 g (0.0165 mol) of potassium t-butoxide and 1.96 mL (0.0165 mol) of benzyl chloride to give after silica chromatography (gradient, toluene→10% EtOAc/toluene) 3.78 g (68% yield) of 5-methoxy-2-methyl-1-(phenylmethyl)-1H-indole-3-acetic acid ethyl ester, mp, 63°–64° C.

Analyses: Calc'd for $C_{21}H_{23}NO_3$: C, 74.75; H, 6.87; N, 4.15. Found: C, 74.76; H, 6.89; N, 4.28.

B. 5-Methoxy-2-methyl-1-(phenylmethyl)-1H-indole-3-acetic acid hydrazide. A solution of 1.0 g (2.96 mmol) of 5-methoxy-2-methyl-1-(phenylmethyl)-1H-indole-3-acetic acid ethyl ester and 5 mL of hydrazine in 50 mL of MeOH was reacted as described in Example 3, Part C, to give by trituration with ether 920 mg (96% yield) of 5-methoxy-2-methyl-1-(phenylmethyl)-1H-indole-3-acetic acid hydrazide mp, 161°–162° C.

Analyses: Calc'd for $C_{19}H_{21}N_3O_2$: C, 70.53; H, 6.54; N, 12.99. Found: C, 70.41; H, 6.58; N, 12.93.

C. 5-Methoxy-2-methyl-1-(phenylmethyl)-1H-indole-3-acetamide. Using the method as in Example 3, Part D, 945 mg (2.9 mmol) of 5-methoxy-2-methyl-1-(phenylmethyl)-1H-indole-3-acetic acid hydrazide was reacted in 50 mL of EtOH using 1.5 g of Raney nickel. Workup of this reaction mixture gave a crude product that was filtered through silica using EtOAc and crystallized from $CH_2Cl_2$/MeOH to give 225 mg (25 yield) of 5-methoxy-2-methyl-1-(phenylmethyl)-1H-indole-3-acetamide, mp, 128°–130° C.

Analyses: Calc'd for $C_{19}H_{20}N_2O_2$: C, 74.00; H, 6.54; N, 9.08. Found: C, 74.00; H, 6.51; N, 9.05.

Example 6

Preparation of 1-(2,6-Dichlorophenylmethyl)-5-methoxy-2-methyl-1H-indole-3-acetamide A. 1-(2,6-Dichlorophenylmethyl)-5-methoxy-2-methyl-1H-indole-3-acetic acid ethyl ester. A suspension of 80 mg (2 mmol) of 60% NaH/mineral oil was washed with hexane and placed in 8 mL of DMF. With ice-bath cooling, 494 mg (2 mmol) of 5-methoxy-2-methyl-1H-indole-3-acetic acid ethyl ester was added and stirred 1 hour, then 391 mg (2 mmol) of alpha,2,6-trichlorotoluene was added and stirring maintained for 1.5 hours. The mixture was diluted with water, extracted with EtOAc, the EtOAc solution washed with water/NaCl, and dried (MgSO$_4$). The solution was concentrated at reduced pressure, and the product chromatographed on silica, eluting with 25% EtOAc/hexane to give 556 mg (68% yield) of 1-(2,6-dichlorophenylmethyl)-5-methoxy-2-methyl-1H-indole-3-acetic acid ethyl ester, which solidified on standing, melting point, 131°–133° C.

Analyses: Calc'd for $C_{21}H_{21}Cl_2NO_3$: C, 62.08; H, 5.21; N, 3.45. Found: C, 61.79; H, 5.23; N, 3.51.

B. 1-(2,6-Dichlorophenylmethyl)-5-methoxy-2-methyl-1H-indole-3-acetic acid hydrazide. Hydrazine (1.3 mL) was added to 533 mg (11.3 mmol) of 1-(2,6-dichlorophenylmethyl)-5-methoxy-2-methyl-1H-indole-3-acetic acid ethyl ester in 10 mL of EtOH and the mixture heated to maintain reflux for 6 hours. After cooling the mixture was diluted with water, extracted with EtOAc, the EtOAc solution washed with a sodium chloride solution and dried over MgSO$_4$. The solvent was removed at reduced pressure and the residue crystallized from MeOH to give 250 mg (61% yield) of 1-(2,6-dichlorophenylmethyl)-5-methoxy-2-methyl-1H-indole-3-acetic acid hydrazide, mp 194°–196° C.

Analyses: Calc'd for $C_{19}H_{19}Cl_2N_3O_2$: C, 58.17; H, 4.88; N, 10.71. Found: C, 58.65; H, 4.98; N, 10.68.

C. 1-(2,6-Dichlorophenylmethyl)-5-methoxy-2-methyl-1H-indole-3-acetamide. Raney nickel was added to 168 mg (0.43 mmol) of 1-(2,6-dichlorophenylmethyl)-5-methoxy-2-methyl-1H-indole-3-acetic acid hydrazide in 10 mL of EtOH and the mixture heated at reflux temperature for 3.5 hours. After cooling, the solvent was decanted from the solids, the solids washed several times with EtOAc and the combined solvents concentrated at reduced pressure. The residue was filtered through silica eluting with EtOAc and then crystallized from MeOH to give 24 mg (15% yield) of 1-(2,6-dichlorophenylmethyl)-5-methoxy-2-methyl-1H-indole-3-acetamide, mp, 203°–205° C.

Analyses: Calc'd for $C_{19}H_{18}Cl_2N_2O_2$: C, 60.49; H, 4.81; N, 7.42. Found: C, 60.75; H, 4.89; N, 7.65.

Example 7

Preparation of 1-[(4-Benzyloxyphenyl)methyl]-5-methoxy-2-methyl-1H-indole-3-acetamide A. 1-[(4-Benzyloxyphenyl)methyl]-5-methoxy-2-methyl-1H-indole-3-acetic acid. Using the method described in Example 6, Part A, 2.0 g (8.12 mmol) of 5-methoxy-2-methyl-1H-indole-3-acetic acid ethyl ester, 0.325 g (8.12 mmol) of 60% NaH/mineral oil, and 1.88 g (8.12 mmol) of 4-benzyloxy-1-chloromethylbenzene were reacted to give on workup 800 mg of crude 1-[(4-benzyloxyphenyl)methyl]-5-methoxy-2-methyl-1H-indole-3-acetic acid ethyl ester. The crude ester in 50 mL of MeOH and 15 mL of 1N NaOH was heated at reflux temperature for 3 hours and left standing for 16 hours. After diluting with water, the mixture was made acidic with 1N HCl and extracted with EtOAc. The EtOAc solution was dried (Na$_2$SO$_4$) and concentrated. The residue was crystallized from MeOH to give 280 mg (32% yield) of 1-[(4-benzyloxyphenyl)methyl]-5-methoxy-2-methyl-1H-indole-3-acetic acid, mp, 175°–179° C.

Analyses: Calc'd for $C_{26}H_{25}NO_4$: C, 75.16; H, 6.06 N, 3.37. Found: C, 75.05; H, 6.07; N, 3.47.

B. 1-[(4-Benzyloxyphenyl)methyl]-5-methoxy-2-methyl-1H-indole-3-acetamide. Using the method in Example 1, F, 170 mg (0.41 mmol) of 1-[(4-benzyloxyphenyl)-methyl]-5-methoxy-2-methyl-1H-indole-3-acetic acid, 0.1 mL of ethyl chloroformate, 1 mL of triethylamine and excess NH$_3$ were reacted to give 60 mg (35% yield) of 1-[(4-benzyloxyphenyl)methyl]-5-methoxy-2-methyl-1H-indole-3-acetamide, after crystallizing from MeOH, melting at 155°–157° C.

Analyses: Calc'd for $C_{26}H_{26}N_2O_3$: C, 75.34; H, 6.32; N, 6.76. Found: C, 75.09; H, 6.35; N, 6.64.

Example 8

Preparation of 5-Methoxy-2-methyl-1-[(2-pyridyl)methyl]-1H-indole-3-acetamide

A. 5-Methoxy-2-methyl-1-[(2-pyridyl)methyl]-1H-indole-3-acetic acid ethyl ester. Using the procedure described in Example 6, Part A, 494 mg (2 mmol) of 5-methoxy-2-methyl-1H-indole-3-acetic acid ethyl ester was reacted with 160 mg (4 mmol) of 60% NaH/mineral oil and 328 mg (2 mmol) of 2-picolyl chloride hydrochloride and after chromatography on silica (eluting with 50% EtOAc/hexane) there was obtained 510 mg (75%) of 5-methoxy-2-methyl-1-[(2-pyridyl)methyl]-1H-indole-3-acetic acid ethyl ester as an oil.

Analyses: Calc'd for $C_{20}H_{22}N_2O_3$: C, 70.99; H, 6.55; N, 8.28. Found: C, 71.28; H, 6.84; N, 8.44.

B. 5-Methoxy-2-methyl-1-[(2-pyridyl)methyl]-1H-indole-3-acetic acid hydrazide. Using the method described in Example 6, Part B, 480 mg (1.4 mmol) of 5-methoxy-2-methyl-1-[(2-pyridyl)methyl]-1H-indole-3-acetic acid ethyl ester was reacted with 1.4 mL of hydrazine to give on crystallization from MeOH 304 mg (67% yield) of 5-methoxy-2-methyl-1-[(2-pyridyl)methyl]-1H-indole-3-acetic acid hydrazide, mp, 147°–148° C.

Analyses: Calc'd for $C_{18}H_{20}N_4O_2$: C, 66.65; H, 6.22; N, 17.27. Found: C, 66.40; H, 6.21; N, 17.34.

C. 5-Methoxy-2-methyl-1-[(2-pyridyl)methyl]-1H-indole-3-acetamide.

Using the procedure in Example 6, Part C, 200 mg (0.62 mmol) of 5-methoxy-2-methyl-1-[(2-pyridyl)methyl]-1H-indole-3-acetic acid hydrazide and approximately 1 gram of Raney nickel in 10 mL of EtOH were reacted to give after chromatographing twice on silica eluting with EtOAc followed by 5% MeOH/EtOAc, 54 mg (28% yield) of 5-methoxy-2-methyl-1-[(2-pyridyl)methyl]-1H-indole-3-acetamide, as a semi-solid material.

Analyses: Calc'd for $C_{18}H_{19}N_3O_2$: C, 69.88; H, 6.19; N, 13.58. Found: C, 70.04; H, 6.32; N, 13.85.

Example 9

Preparation of 2-Ethyl-5-methoxy-1-(phenylmethyl)-1H-indole-3-acetamide

A. N-tert-Butoxycarbonyl-4-methoxy-2-methylaniline. By the procedure in Example 1, Part A, 13.7 g (0.1 mole) of 4-methoxy-2-methylaniline was reacted with 25 g (0.1145 mol) of di-tert-butyl dicarbonate to give 17.25 g (73% yield) of N-tert-butoxycarbonyl-4-methoxy-2-methylaniline melting at 80°–82° C., after crystallizing from hexane.

Analyses: Calc'd for $C_{13}H_{19}NO_3$: C, 65.80; H, 8.07; N, 5.90. Found: C, 65.86; H, 8.15; N, 5.61.

B. 1-[2-(tert-Butoxycarbonylamino)-5-methoxyphenyl]-2-butanone. A solution of 1.3M sec-butyl lithium/cyclohexane(81 mL, 0.105 mol) was added slowly to 11.85 g (0.05 mol) of N-tert-butoxycarbonyl-4-methoxy-2-methylaniline in 80 mL of THF while keeping the temperature below −40° C. with a dry ice-ethanol bath. The bath was removed and the temperature allowed to rise to −20° C. and then the bath was replaced. After the temperature had cooled to −60° C., 6.1 g (0.052 mol) of N-methoxy-N-methylpropanamide in an equal volume of THF was added dropwise. The reaction mixture was stirred 1 hour, the cooling bath removed and stirred an additional 1 hour. It was then poured into a mixture of 200 mL of ether and 200 mL of 1N HCl. The organic layer was separated, washed with water, dried over $Na_2SO_4$ and concentrated at reduced pressure to give 10.9 g (74% yield) of 1-(2-(tert-butoxycarbonylamino)-5-methoxyphenyl]-2-butanone, melting at 80°–81° C., after chromatography on silica eluting with 5% EtOAc/toluene.

Analyses: Calc'd for $C_{16}H_{23}NO_4$: C, 65.51; H, 7.90; N, 4.77. Found: C, 65.69; H, 7.89; N, 4.90.

C. 2-Ethyl-5-methoxy-1H-indole. 1-[2-(tert-Butoxycarbonylamino)-5-methoxyphenyl]-2-butanone (7.33 g, 0.025 mol) in 120 mL of $CH_2Cl_2$ and 20 mL of trifluoroacetic acid was stirred for 20 h, washed with water, $NaHCO_3$ solution and the product chromatographed on silica (eluted with 20% EtOAc/hexane) to give 2.54 g (58% yield) of 2-ethyl-5-methoxy-1H-indole as a white solid, mp 49°–50° C.

Analyses: Calc'd for $C_{11}H_{13}NO$: C, 75.40; H, 7.48; N, 7.99. Found: C, 75.64 H, 7.61; N, 8.04.

D. 2-Ethyl-5-methoxy-1H-indole-3-acetic acid methyl ester. As in Example 1, Part C, 3.5 g (0.02 mole) of 5-methoxy-2-ethyl-1H-indole was treated with 12.5 mL (0.02 mol) of a 1.6M solution of n-butyl lithium in hexane, 20 ml (0.02 mol) of a 1M solution of $ZnCl_2$ in ether, and 1.89 mL (0.02 mol) of methyl 2-bromoacetate to give after chromatography on silica (toluene→10% EtOAc/toluene) 3.32 g (59%) of 2-ethyl-5-methoxy-1H-indole-3-acetic acid methyl ester as an oil.

Analyses: Calc'd for $C_{14}H_{17}NO_3$: C, 67.99; H, 6.93; N, 5.66. Found: C, 67.73; H, 6.94; N, 5.39.

E. 2-Ethyl-5-methoxy-1-(phenylmethyl)-1H-indole-3-acetic acid methyl ester. A solution of 2.47 g (0.01 mol) of 2-ethyl-5-methoxy-1H-indole-3-acetic acid methyl ester in 25 mL of DMF was treated with 1.12 g (0.01 mol) of potassium t-butoxide, stirred 0.5 h, and 1.15 mL (0.01 mol) of benzyl chloride added. After 72 hours, the reaction mixture was diluted with water, extracted with EtOAc, the EtOAc solution was washed four times with water and dried over $Na_2SO_4$. After concentrating at reduced pressure, the product was purified by chromatography on silica, eluting with a gradient, toluene→10% EtOAc/toluene, to give 1.5 g (44% yield) of 2-ethyl-5-methoxy-1-(phenylmethyl)-1H-indole-3-acetic acid methyl ester as oil.

Analyses: Calc'd for $C_{21}H_{23}NO_3$: C, 74.75; H, 6.87; N, 4.15. Found: C, 75.00; H, 6.99; N, 4.28.

F. 2-Ethyl-5-methoxy-1-(phenylmethyl)-1H-indole-3-acetic acid hydrazide.

Using the method described in Example 3, Part C, 748 mg (2.2 mmol) of 2-ethyl-5-methoxy-1-(phenylmethyl)-1H-indole-3-acetic acid methyl ester was reacted with 2.2 mL of hydrazine to give 552 mg (74% yield) of 2-ethyl-5-methoxy-1-(phenylmethyl)-1H-indole-3-acetic acid hydrazide, that crystallized out of the reaction mixture on cooling (melting point, 138°–140° C.).

Analyses: Calc'd for $C_{20}H_{23}N_3O_2$: C, 71.19; H, 6.87; N, 12.45. Found: C, 71.13 H, 6.86; N, 12.33.

G. 2-Ethyl-5-methoxy-1-(phenylmethyl)-1H-indole-3-acetamide. An ethanol solution of 225 mg (0.67 mmol) of 2-ethyl-5-methoxy-1-(phenylmethyl)-1H-indole-3-acetic acid hydrazide was reacted with approximately 1.5 g of Raney nickel as described in Example 6, Part C, and the crude product chromatographed on silica eluting with 50% EtOAc/hexane, EtOAc, and then 5% MeOH/EtOAc to give after crystallizing from MeOH, 46 mg (21% yield) of 2-ethyl-5-methoxy-1-(phenylmethyl)-1H-indole-3-acetamide, mp, 161°–166° C.

Analyses: Calc'd for $C_{20}H_{22}N_2O_2$: C, 74.51; H, 6.88; N, 8.69. Found: C, 74.77 H, 6.94; N, 8.81.

Example 10

Preparation of 5-Methoxy-1-(phenylmethyl)-2-propyl-1H-indole-3-acetamide

A. 1-[2-(tert-Butoxycarbonylamino)-5-methoxyphenyl]-2-pentanone. Using the method described in Example 9, Part B, 5.17 g (0.064 mol) of N-tert-butoxycarbonyl-4-methoxy-2-methylaniline (Example 9, Part A) was treated with 1.3M sec-butyl lithium/cyclohexane (100 mL, 0.13 mol) and 8.4 g (0.064 mol) of N-methoxy-N-methylbutanamide to give 14.31 g (73% yield) of 1-(tert-butoxycarbonylamino-5-methoxyphenyl)-2-pentanone, melting at 77°–78° C., after chromatography on silica eluting with 5% EtOAc/toluene.

Analyses: Calc'd for $C_{17}H_{25}NO_4$: C, 66.43; H, 8.20; N, 4.56. Found: C, 66.42; H, 8.09; N, 4.71.

B. 5-methoxy-2-propyl-1H-indole. 1-[2-(tert-Butoxycarbonylamino)-5-methoxyphenyl]-2-pentanone (14.27 g, 0.0465 mol) was treated with 20 mL of trifluoroacetic acid as described in Example 9, Part C and the product crystallized from hexane to give 5.5 g (58% yield) of 5-methoxy-2-propyl-1H-indole as a white solid, mp 49°–50° C.

Analyses: Calc'd for $C_{12}H_{15}NO$: C, 76.16; H, 7.99; N, 7.40. Found: C, 76.36 H, 8.07; N, 7.52.

C. 5-Methoxy-2-propyl-1H-indole-3-acetic acid methyl ester. As in Example 1, Part C, 5.125 g (0.0271 mole) of 5-methoxy-2-propyl-1H-indole was treated with 16.9 mL (0.0271 mol) of a 1.6M solution of n-butyl lithum in hexane, 27.1 mL (0.0271 mol) of a 1M solution of $ZnCl_2$ in ether, and 2.7 mL (0.0271 mol) of methyl 2-bromoacetate to give after chromatography on silica (20% EtOAc/hexane) 4.65 g (66%) of 5-methoxy-2-propyl-1H-indole-3-acetic acid methyl ester as an oil.

Analyses: Calc'd for $C_{15}H_{19}NO_3$: C, 68.94; H, 7.33; N, 5.36. Found: C, 68.69; H, 7.36; N, 5.63.

D. 5-Methoxy-1-(phenylmethyl)-2-propyl-1H-indole-3-acetic acid methyl ester. Using the procedure described in Example 1 Part D, 522 mg (2 mmol) of 5-methoxy-2-propyl-1H-indole-3-acetic acid methyl ester was reacted with 80 mg (2 mmol) of 60% NaH/mineral oil and 0.24 mL (2 mmol) of benzyl bromide to give after silica chromatography (25% EtOAc/hexane) 501 mg (71%) of 5-methoxy-1-(phenylmethyl)-2-propyl-1H-indole-3-acetic acid methyl ester as an oil.

E. 5-Methoxy-1-(phenylmethyl)-2-propyl-1H-indole-3-acetic acid hydrazide. Using the method described in Example 3, Part C, 480 mg (1.37 mmol) of 5-methoxy-1-(phenylmethyl)-2-propy-1H-indole-3-acetic acid methyl ester was reacted with 1.4 mL of hydrazine to give after crystallizing from MeOH 56 mg (74% yield) of 5-methoxy-1-(phenylmethyl)-2-propyl-1H-indole-3-acetic acid hydrazide, mp 140°–141° C.

Analyses: Calc'd for $C_{21}H_{25}N_3O_2$: C, 71.77; H, 7.17; N, 11.96. Found: C, 71.98 H, 7.12; N, 11.98.

F. 5-Methoxy-1-(phenylmethyl)-2-propyl-1H-indole-3-acetamide. An ethanol solution of 160 mg (0.46 mmol) of 5-methoxy-1-(phenylmethyl)-2-propyl-1H-indole-3-acetic acid hydrazide was reacted with approximately 1.0 g of Raney nickel as described in Example 6, Part C, and the crude product chromatographed on silica eluting with EtOAc to give after crystallizing from MeOH, 55 mg (36% yield) of 5-methoxy-1-(phenylmethyl)-2-propyl-1H-indole-3-acetamide, mp, 154°–156° C.

Analyses: Calc'd for $C_{21}H_{24}N_2O_2$: C, 74.97; H, 7.19; N, 8.33. Found: C, 75.05; H, 7.21; N, 8.29.

Example 11

Preparation of 2-Chloro-5-methoxy-1-(phenylmethyl)-1H-indole-3-acetamide

A. 1-Dimethylaminomethyl-5-methoxy-1H-indole. A 37% aqueous solution of formaldehyde (11 g, 0.176 mol) was added dropwise to 10 g (0.068 mol) of 5-methoxy-1H-indole and 17 mL (0.176 mol) of 40% aqueous dimethylamine in 100 mL of tetrahydrofuran and the mixture heated to maintain reflux for 3 hours. After cooling water was added and the mixture extracted with EtOAc. The EtOAc solution was washed twice with water, dried ($Na_2SO_4$), and concentrated at reduced pressure. The residue was chromatographed on silica eluting with a gradient, $CH_2Cl_2 \rightarrow 2\%$ MeOH/$CH_2Cl_2$, to give 6.26 g (45% yield) of 1-dimethylaminomethyl-5-methoxy-1H-indole as an oil.

Analyses: Calc'd for $C_{12}H_{16}N_2O$: C, 70.56; H, 7.89; N, 13.71. Found: C, 70.79; H, 7.92; N, 13.64.

B. 2-Chloro-5-methoxy-1H-indole-3-acetic acid methyl ester. Cooling with a dry ice-ethanol bath, 20 mL (0.026 mol) of 1.3M sec-butyl lithium/cyclohexane was added to 5.1 g (0.025 mol) of 1-dimethylaminomethyl-5-methoxy-1H-indole in 100 mL of THF keeping the temperature below –50° C. The cooling bath was removed and the temperature allowed to reach 0° C. and the bath then replaced. At –60° C., 3.32 mL (0.026 mol) of benzenesulfonyl chloride in 10 mL of THF was added, stirred 0.3 hours, the bath removed, and the temperature allowed to reach 20° C. over 1 hour. To this mixture was added 100 mL of 1N HCl and 50 mL of EtOAc and the mixture stirred for 20 hours. After making basic with 5N NaOH, the EtOAc layer was separated, washed with water, dried ($Na_2SO_4$), and concentrated at reduced pressure. The residue was chromatographed on silica eluting with toluene to give 1.37 g (29% yield) of crude 2-chloro-5-methoxy-1H-indole. To this material (7.55 mmol) in 30 mL of THF was added 4.7 mL (7.55 mmol) of 1.6M n-butyl lithium/hexane keeping the temperature below 10° C. with an ethanol-ice bath. After 0.25 h, 7.55 mL (7.55 mmol) of 1M $ZnCl_2$/ether was added, stirred 2 hours, concentrated at reduced pressure, and 40 mL of toluene added followed by 0.72 mL (7.55 mmol) of methyl 2-bromoacetate. The mixture was stirred for 16 hours, warmed at 76° C. for 4 h, cooled, and 50 mL of 1N HCl and 40 mL of EtOAc added. After 0.5 hour, the organic layer was separated, dried ($Na_2SO_4$), and concentrated at reduced pressure. The residue was chromatographed on silica and eluted with a solvent gradient (toluene→20% EtOAc/toluene) to give 0.79 g (41% yield) of 2-chloro-5-methoxy-1H-indole-3-acetic acid methyl ester, as an oil.

Analyses: Calc'd for $C_{12}H_{12}ClNO_3$: C, 56.82; H, 4.77; N, 5.52. Found: C, 56.47; H, 5.19; N, 4.99.

C. 2-Chloro-5-methoxy-1-(phenylmethyl)-1H-indole-3-acetamide. The method in Example 2, Part B, was used to react 660 mg (2.6 mmol) of 2-chloro-5-methoxy-1H-indole-3-acetic acid methyl ester, 140 mg (3.5 mmol) of 60% NaH/mineral oil and 0.5 mL of benzyl bromide to give a material that was chromatographed on silica (eluted with 5% ether/hexane→15% ether/hexane). This crude intermediate, 2-chloro-5-methoxy-1-(phenylmethyl)-1H-indole-3-acetic acid methyl ester, weighed 710 mg (79% yield). One mmol (344 mg) of this material was dissolved in 20 mL of benzene, 5 mL of 0.67M $(CH_3)_2AlNH_2$/benzene added, and the mixture heated to maintain reflux for 2 hours, an additional 5 mL of aluminum reagent added and heating continued for 1.5 hours. After cooling with an ice-bath, the mixture was decomposed with 1N HCl, extracted with EtOAc, the EtOAc solution was washed with saturated NaCl, dried ($Na_2SO_4$), and concentrated at reduced pressure. Chromatography of the residue on silica (eluted with $CH_2Cl_2 \rightarrow 2\%$ MeOH/$CH_2Cl_2$) gave 50 mg of starting material (ester) and 165 mg (50% yield) of 2-chloro-5-methoxy-1-(phenylmethyl)-1H-indole-3-acetamide, mp. 166°–168° C.

Analyses: Calc'd for $C_{18}H_{17}ClN_2O_2$: C, 66.07; H, 5.38; Cl, 10.76; N, 8.48 Found: C, 65.75; H, 5.21; Cl, 10.78; N, 8.52.

Example 12

Preparation of 5-Methoxy-2-(methylthio)-1-(phenylmethyl)-1H-indole-3-acetamide Sulfuryl chloride (0.8 mL, 10 mmol) was added to an ice-bath cooled solution of 1.0 mL of dimethyldisulfide in 25 mL of methylene chloride, the cooling bath removed, and the mixture allowed to warm to room temperature. Three mL of this solution (containing methanesulfenyl chloride) was added to 320 mg (1.1 mmol) of 5-methoxy-1-(phenylmethyl)-1H-indole-3-acetamide (Example 3) in 100 mL of methylene chloride, stirred 0.33 hours, saturated $NaHCO_3$ solution added, stirred well, and the methylene chloride solution separated, washed with saturated NaCl, dried ($Na_2SO_4$), and concentrated at reduced pressure. The residue chromatographed on silica was eluted with 40% EtOAc/hexane→100% EtOAc to give 115 mg (31% yield) of 5-methoxy-2-(methylthio)-1-(phenylmethyl)-1H-indole-3-acetamide, mp, 195°–197° C.

Analyses: Calc'd for $C_{19}H_{20}N_2O_2S$: C, 67.03; H, 5.92; N, 8.22; S, 9.42. Found: C, 66.57; H, 5.93; N, 7.92; S, 9.88.

Example 13

Preparation of 5-Benzyloxy-2-methyl-1-(phenylmethyl)-1H-indole-3-acetamide

5-Hydroxy-2-methyl-1-(phenylmethyl)-1H-indole-3-acetamide (400 mg, 1.4 mmol) was dissolved in 50 mL of DMSO, 40 mg (1.0 mmol) of 60% NaH/mineral oil added, stirred approximately 0.5 hour, 0.2 mL of benzyl bromide added and stirring maintained 2.5 hours. The mixture was diluted with water, extracted with EtOAc, the EtOAc solution washed with water, saturated NaCl solution, dried ($Na_2SO_4$), and concentrated at reduced pressure. The residue was chromatographed on silica (eluted with a gradient, $CH_2Cl_2 \rightarrow 2\%$ MeOH/$CH_2Cl_2$) and crystallized from $CH_2Cl_2$/MeOH to give 440 mg (82% yield) of 5-benzyloxy-2-methyl-1-(phenylmethyl)-1H-indole-3-acetamide, mp, 118°–120° C.

Analyses: Calc'd for $C_{25}H_{24}N_2O_2$: C, 78.10; H, 6.29; N, 7.29. Found: C, 77.56; H, 6.33; N, 7.16.

Example 14

Preparation of 1-Decyl-5-methoxy-2-methyl-1H-indole-3-acetamide

A. 1-Decyl-5-methoxy-2-methyl-1H-indole-3-acetic acid ethyl ester. Using the method described in Example 1, Part D, 2.47 g (10.0 mmol) of 5-methoxy-2-methyl-1H-indole-3-acetic acid ethyl ester was reacted with 1.12 g (10.0 mmol) of potassium t-butoxide and 2.07 mL (10.0 mmol) of decyl bromide to give after chromatography on silica (eluting with 5% EtOAc/toluene) 2.16 g (56% yield) of 1-decyl-5-methoxy-2-methyl-1H-indole-3-acetic acid ethyl ester.

Analysis: Calc'd for $C_{24}H_{37}NO_3$: C, 74.38; H, 9.62; N, 3.61. Found: C, 74.53; H, 9.38; N, 3.57.

B. 1-Decyl-5-methoxy-2-methyl-1H-indole-3-acetic acid hydrazide. A solution of 2.1 g (5.4 mmol) of 1-decyl-ethoxy-2-methyl-1H-indole-3-acetic acid ethyl ester and 5 mL of hydrazine in 40 mL of EtOH was heated to maintain reflux for 5 hours, let stand 16 hours, the precipitate filtered and crystallized from MeOH to give 0.65 g (32% yield) of 1-decyl-5-methoxy-2-methyl-1H-indole-3-acetic acid hydrazide, mp, 129°–131° C.

Analysis: Calc'd for $C_{22}H_{35}N_3O_2$: C, 70.74; H, 9.44; N, 11.25. Found: C, 70.79; H, 9.60; N, 11.13.

C. 1-Decyl-5-methoxy-2-methyl-1H-indole-3-acetamide. Approximately 1.5 g of Raney Ni was added to 1.5 g (4.0 mmol) of 1-decyl-5-methoxy-2-methyl-1H-indole-3-acetic acid hydrazide in 250 mL of EtOH and the mixture heated at reflux for 3 hours. After cooling the mixture was filtered and the filtrate concentrated at reduced pressure. The residue was crystallized from EtOAc/hexane to give 0.987 g (69% yield) of 1-decyl-5-methoxy-2-methyl-1H-indole-3-acetamide, mp, 110°–111° C.

Analysis: Calc'd for $C_{22}H_{34}N_2O_2$: C, 73.70; H, 9.56; N, 7.81. Found: C 76.80; H, 9.36; N, 7.95.

Example 15

Preparation of 5-Aminocarbonyl-2-methyl-1-(phenylmethyl)-1H-indole-3-acetamide

A. 5-Ethoxycarbonyl-2-methyl-1H-indole-3-acetic acid ethyl ester.

Dry hydrogen chloride was bubbled into a solution of 25 g (0.1643 mol) of 4-hydrazinobenzoic acid and 20.5 mL (0.2 mol) of levulinic acid for 0.5 hours and the reaction mixture heated to maintain reflux for 20 hours. After cooling, the mixture was concentrated at reduced pressure, water added, and the mixture extracted with EtOAc/ether. After drying ($Na_2SO_4$), the solution was concentrated and the residue chromatographed on silica and eluted with a solvent gradient, (toluene→20% EtOAc/toluene) to give in the later fractions 12 g of a mixture of 5-ethoxycarbonyl-2-methyl-1H-indole-3-acetic acid ethyl ester and the intermediate hydrazone. This mixture was treated again with dry HCl in 250 mL of EtOH and heated to maintain reflux for 16 hours. After cooling, the mixture was poured into water and extracted with EtOAc, the EtOAc solution washed with $Na_2CO_3$ solution and dried ($Na_2SO_4$). Silica chromatography (toluene→20% EtOAc/toluene) gave 3.6 g (7.6% yield) of 5-ethoxycarbonyl-2-methyl-1H-indole-3-acetic acid ethyl ester, mp, 74°–76° C.

Analyses: Calc'd for $C_{16}H_{19}NO_4$: C, 66.42; H, 6.62; N, 4.84 Found: C, 66.54; H, 5.00; N, 10.39.

B. 5-Ethoxycarbonyl-2-methyl-1-(phenylmethyl)-1H-indole-3-acetic acid ethyl ester.

Using the procedure described in Example 2, Part B, 2.18 g (7.5 mmol) of 5-ethoxycarbonyl-2-methyl-1H-indole-3-acetic acid ethyl ester was reacted with 320 mg (8 mmol) of 60% NaH/mineral oil and 1.0 mL (8.4 mmol) of benzyl bromide to give after silica chromatography (25% ether/hexane→50% ether/hexane) 1.6 g (56%) of 5-ethoxycarbonyl-2-methyl-1-(phenylmethyl)-1H-indole-3-acetic acid ethyl ester.

C. 5-Carboxy-2-methyl-1-(phenylmethyl)-1H-indole-3-acetic acid ethyl ester.

A solution of 1.6 g (4.2 mmol) of 5-ethoxycarbonyl-2-methyl-1-(phenylmethyl)-1H-indole-3-acetic acid ethyl ester and 4.2 mL of 1N NaOH in 75 mL of EtOH was stirred 2.25 hours, 10 mL of 1N NaOH added, and stirred an additional 18.5 hours. The reaction mixture was acidified with 1N HCl, extracted with EtOAc, the EtOAc solution washed with saturated NaCl solution, dried ($Na_2SO_4$), and concentrated at reduced pressure. The residue was heated in 150 mL of EtOH for 4.5 hours, and left at room temperature for 96 hours. After concentrating at reduced pressure, the residue was chromatographed on silica (25% ether/hexane→50% ether/hexane) to give 110 mg (7.5% yield) of 5-carboxy-2-methyl-1-(phenylmethyl)-1H-indole-3-acetic acid ethyl ester.

D. 5-Hydrazinocarbonyl-2-methyl-1-(phenylmethyl)-1H-indole-3-acetic acid hydrazide.

Using the method described in Example 3, Part C, 110 mg (0.31 mmol) of 5-carboxy-2-methyl-1-(phenylmethyl)-1H-indole-3-acetic acid ethyl ester was reacted with 3 mL of hydrazine (total reflux time, 78 hours) to give on cooling of the reaction mixture 40 mg (38% yield) of 5-hydrazinocarbonyl-2-methyl-1-(phenylmethyl)-1H-indole-3-acetic acid hydrazide, mp, >255° C.

Analyses: Calc'd for $C_{19}H_{21}N_5O_2$: C, 64.94; H, , 5.02; N, 19.93. Found: C, 65.15; H, 6.14; N, 19.82.

E. 5-Aminocarbonyl-2-methyl-1-(phenylmethyl)-1H-indole-3-acetamide.

Using the method described in Example 3, Part D, 40 mg (0.11 mmol) of 5-hydrazinocarbonyl-2-methyl-1-(phenylmethyl)-1H-indole-3-acetic acid hydrazide was hydrogenolized using approximately 1 g of Raney nickel in 50 mL of EtOH to give after chromatography on silica (gradient, $CH_2Cl_2$→8% $MeOH/CH_2Cl_2$) 17 mg (50% yield) of 5-aminocarbonyl-2-methyl-1-(phenylmethyl)-1H-indole-3-acetamide.

Analyses: Calc'd for $C_{19}H_{19}N_3O_2$: C, 71.01; H, 5.96; N, 13.07. Found: C, 67.21; H, 5.76; N, 12.66.

Example 16

Preparation of 2-Methyl-5-nitro-1-(phenylmethyl)-1H-indole-3-acetamide

A. 2-Methyl-5-nitro-1H-indole.

A solution of 17.0 g (0.2 mol) of sodium nitrate in 150 mL of sulfuric acid was added dropwise to 26.9 g (0.205 mol) of 2-methyl-1H-indole in 150 mL of sulfuric acid keeping the temperature at −10° to 0° C. with an ethanol-water bath. After 0.25 hours, the mixture was poured onto ice, extracted with EtOAc, the EtOAc solution washed with water, $Na_2CO_3$ solution and dried ($Na_2SO_4$). After concentrating at reduced pressure, the residue was crystallized from EtOH to give 20.86 g (59% yield) of 2-methyl-5-nitro-1H-indole, mp, 163°–165° C.

Analyses: Calc'd for $C_9H_8N_2O_2$: C, 61.36; H, 4.58; N, 15.90. Found: C, 61.36; H, 4.61; N, 16.17.

B. 2-Methyl-5-nitro-1-(phenylmethyl)-1H-indole.

Hexane was used to wash 80 mg (2.0 mmol) of 60% NaH/mineral oil and 6 mL of DMF was added followed by 352 mg (2.0 mmol) of 2-methyl-5-nitro-1H-indole. After 0.33 hours, 0.24 mL (2.0 mmol) of benzyl bromide was added, stirred 0.5 hours and diluted with water. The mixture was extracted with EtOAc, the EtOAc washed with a saturated NaCl solution, dried MgSO$_4$) and on concentrating at reduced pressure, crystals formed. These were washed with MeOH to give 400 mg (75% yield) of 2-methyl-5-nitro-1-(phenylmethyl)-1H-indole, mp, 150°–152° C.

Analyses: Calc'd for C$_{16}$H$_{14}$N$_2$O$_2$: C, 72.17; H, 5.30; N, 10.52. Found: C, 72.37; H, 5.24; N, 10.53.

C. 2-Methyl-5-nitro-1-(phenylmethyl)-1H-indole-3-glyoxylic acid amide.

To a cooled solution of 380 mg (1.4 mmol) of 2-methyl-5-nitro-1-(phenylmethyl)-1H-indole in 10 mL of methylene chloride was added 0.12 mL of oxalyl chloride, the cooling bath was removed and the reaction mixture stirred for 3.0 hours. After concentrating at reduced pressure to a solid, the material was redissolved in 10 mL of methylene chloride and anhydrous ammonia bubbled in for approximately 5 minutes. After concentrating at reduced pressure, the residue was taken up in EtOAc, washed with water, NaCl solution, dried (MgSO$_4$), and concentrated. The residue was crystallized from MeOH to give 315 mg (67% yield) of 2-methyl-5-nitro-1-(phenylmethyl)-1H-indole-3-glyoxylic acid amide, mp, 204°–206° C.

Analyses: Calc'd for C$_{18}$H$_{15}$N$_3$O$_4$: C, 64.09; H, 4.48; N, 12.46. Found: C, 64.32; H, 4.38; N, 12.44.

D. 2-Methyl-5-nitro-1-(phenylmethyl)-1H-indole-3-glycolic acid amide.

To a mixture of 1.04 g (3.1 mmol) of 2-methyl-5-nitro-1-(phenylmethyl)-1H-indole-3-glyoxylic acid amide in 30 mL of EtOH was added 148 mg (3.9 mmol) of NaBH$_4$, the mixture stirred for 1.0 hour and concentrated at reduced pressure. The residue was stirred with water and EtOAc and the insoluble material filtered to give 1.05 mg (100% yield of 2-methyl-5-nitro-1-(phenylmethyl)-1H-indole-3-glycolic acid amide, mp, 120°–124° C.

Analyses: Calc'd for C$_{18}$H$_{17}$N$_3$O$_4$: C, 63.71; H, 5.05; N, 12.38. Found: C, 64.88; H, 5.38; N, 12.17.

E. 2-Methyl-5-nitro-1-(phenylmethyl)-1H-indole-3-acetamide.

A solution of 0.927 g (2.7 mmol) of 2-methyl-5-nitro-1-(phenylmethyl)-1H-indole-3-glycolic acid amide in 15 mL of trifluoroacetic acid was treated with 1.0 mL (6.0 mmol) of triethylsilane and the mixture stirred for 1.0 hour. After concentrating at reduced pressure, the residue was chromatographed on silca (eluted with EtOAc) and crystallized from MeOH/CH$_2$Cl$_2$ to give 455 mg (52% yield) of 2-methyl-5-nitro-1-(phenylmethyl)-1H-indole-3-acetamide, mp, 189°–192° C.

Analyses: Calc'd for C$_{18}$H$_{17}$N$_3$O$_3$: C, 66.86; H, 5.30; N, 12.99. Found: C, 66.99; H, 5.26; N, 12.95.

Example 17

Preparation of 5-Amino-2-methyl-1-(phenylmethyl)-1H-indole-3-acetamide

A solution of 205 mg (0.634 mmol) of 2-methyl-5-nitro-1-(phenylmethyl)-1H-indole-3-acetamide in 30 mL of 2:1 THF/EtOH was hydrogenated at 60 psi (4218 g/cm$^2$) of hydrogen for 4 hours using 0.1 g of Pd/C as catalyst. The catalyst was filtered and the filtrate concentrated at reduced pressure. The residue was chromatographed on silica eluting with EtOAc and then 5% MeOH/EtOAc to give 52 mg (28% yield) of 5-amino-2-methyl-1-(phenylmethyl)-1H-indole-3-acetamide, mp, 175°–178° C.

Analyses: Calc'd for C$_{18}$H$_{19}$N$_3$O: C, 73.69; H, 6.53; N, 14.32. Found: C, 73.90; H, 6.57; N, 14.25.

Example 18

Preparation of 2-[[3-(2-Amino-2-oxoethyl)-2-methyl-1-(phenylmethyl)-1H-indol-5-yl]oxy]acetic acid ethyl ester A. 5-(Carbethoxymethoxy)-2-methyl-1-(phenylmethyl)-1H-indole-3-acetic acid.

A solution of 590 mg (2.0 mmol) of 5-hydroxy-2-methyl-1-(phenylmethyl)-1H-indole-3-acetic acid (Example 2, Part C) in 30 mL of THF and 10 mL of DMSO was treated with 180 mg (4.5 mmol) of 60% NaH/mineral oil and after 10 minutes, 0.25 mL (2.25 mmol) of ethyl 2-bromoacetate was added. The mixture was stirred for 0.5 hour, acidified with 1N HCl and extracted with EtOAc. The EtOAc solution was washed with water, saturated NaCl solution, dried (Na$_2$SO$_4$) and concentrated at reduced pressure. After chromatography on silica (eluted with a gradient, CH$_2$Cl$_2$→3% MeOH/CH$_2$Cl$_2$) there was obtained 590 mg (77% yield) of 5-(carbethoxymethoxy)-2-methyl-1-(phenylmethyl)-1H-indole-3-acetic acid.

B. 2-[[3-(2-Amino-2-oxoethyl)-2-methyl-1-(phenylmethyl)-1H-indol-5-yl]oxy]acetic acid ethyl ester. While cooling at −5° C. 0.16 mL (2.1 mmol) of methyl chloroformate was added to 630 mg (1.6 mmol) of 5-(carbethoxymethoxy)-2-methyl-1-(phenylmethyl)-1H-indole-3-acetic acid and 0.3 mL (2.2 mmol) of triethylamine in 30 mL of CH$_2$Cl$_2$ and stirred 10 minutes. Anhydrous ammonia was bubbled into the reaction mixture for 0.5 hour, the mixture washed with water, saturated NaCl solution, dried (Na$_2$SO$_4$) and concentrated at reduced pressure. The residue was chromatographed on silica and eluted with a gradient (CH$_2$Cl$_2$→3% MeOH/CH$_2$Cl$_2$) to give after crystallization from ether 270 mg (44% yield) of 2-[[3-(2-amino-2-oxoethyl)-2-methyl-1-(phenylmethyl)-1H-indol-5-yl]oxy] acetic acid ethyl ester, mp, 160°–161° C.

Analyses: Calc'd for C$_{22}$H$_{24}$N$_2$O$_4$: C, 69.46; H, 6.36; N, 7.36. Found: C, 69.69; H, 6.38; N, 7.18.

Example 19

Preparation of 2-[[3-(2-Amino-2-oxoethyl)-2-methyl-1-(phenylmethyl)-1H-indol-5-yl]oxy]acetic acid A solution of 190 mg (0.5 mmol) of 2-[[3-(2-amino-2-oxoethyl)-2-methyl-1-(phenylmethyl)-1H-indol-5-yl]oxy] acetic acid ethyl ester and 2 mL of 5N NaOH in 30 mL of EtOH and 10 mL of THF was stirred for approximately 15 hours, the mixture made acidic with 5N HCl and extracted with EtOAc. The EtOAc solution was washed with saturated NaCl solution, dried (Na$_2$SO$_4$), and concentrated at reduced pressure. The residue was washed with ether to give 155 mg (90% yield) of 2-[[3-(2-amino-2-oxoethyl)-2-methyl-1-(phenylmethyl)-1H-indol-5-yl]oxy]acetic acid, mp, 196°–198° C.

Analyses: Calc'd for C$_{20}$H$_{20}$N$_2$O$_4$: C, 68.17; H, 5.72; N, 7.95. Found: C, 68.35; H, 5.73; N, 7.73.

Example 20

Preparation of 3-[[3-(2-Amino-2-oxoethyl)-2-methyl-1-(phenylmethyl)-1H-indol-5-yl]oxy]-propanic acid methyl ester 5-Hydroxy-2-methyl-1-(phenylmethyl)-1H-indole-3-acetamide (550 mg, 1.8 mmol), 550 mg (4 mmol) of K$_2$CO$_3$ and 0.2 mL of methyl acrylate in 40 mL of acetone was heated to maintain reflux for 100 hours (additional methyl acrylate was added at various times). After cooling, the mixture was diluted with water, extracted with EtOAc, the EtOAc solution washed with saturated NaCl solution and dried ($Na_2SO_4$). After concentrating, the residue was chromatographed on silica (eluted with $CH_2Cl_2 \to 1\%$ MeOH/$CH_2Cl_2$) and crystallized from $CH_2Cl_2$/ether to give 375 mg (55% yield) of 3-[[3-(2-amino-2-oxoethyl)-2-methyl-1-(phenylmethyl)-1H-indol-5-yl]oxy]-propanic acid methyl ester, mp, 113°–115° C.

Analyses: Calc'd for $C_{22}H_{24}N_2O_4$: C, 69.46; H, 6.36; N, 7.36. Found: C, 69.52; H, 6.38; N, 7.33.

Example 21

3-[[3-(2-Amino-2-oxoethyl)-2-methyl-1-(phenylmethyl)-1H-indol-5-yl]oxy]-propanic acid A. 3-[[3-(2-Amino-2-oxoethyl)-2-methyl-1-(phenylmethyl)-1H-indol-5-yl]oxy]-propanic acid benzyl ester. Using the procedure described in Example 21, 270 mg (0.92 mmol) of 5-hydroxy-2-methyl-1-(phenylmethyl)-1H-indole-3-acetamide, 0.5 g of potassium carbonate and 1 mL of benzyl acrylate in 30 mL of MEK were reacted to give 130 mg of 3-[[3-(2-amino-2-oxoethyl)-2-methyl-1-(phenylmethyl)-1H-indol-5-yl]oxy]-propanic acid benzyl ester (chromatographed on silica, eluted with $CH_2Cl_2 \to 7\%$ MeOH/$CH_2Cl_2$).

B. 3-[[3-(2-Amino-2-oxoethyl)-2-methyl-1-(phenylmethyl)-1H-indol-5-yl]oxy]-propanic acid. A mixture of 130 mg (0.29 mmol) of 3-[[3-(2-amino-2-oxoethyl) -2-methyl-1-(phenylmethyl)-1H-indol-5-yl]oxy]-propanic acid benzyl ester and 0.2 g of 10% Pd/C was hydrogenated at 40 psi (2812 g/cm$^2$) of hydrogen for 4.5 hours. The mixture was filtered, and concentrated until the product crystallized. These were washed with ether to give 80 mg (75% yield) of 3-[[3-(2-amino-2-oxoethyl)-2-methyl-1-(phenylmethyl)-1H-indol-5-yl]oxy]-propanic acid, mp, 201°–203° C.

Analyses: Calc'd for $C_{21}H_{22}N_2O_4$: C, 68.84; H, 6.05; N, 7.65. Found: C, 65.88; H, 6.32; N, 6.68.

Example 22

4-[[3-(2-Amino-2-oxoethyl)-2-methyl-1-(phenylmethyl)-1H-indol-5-yl]oxy]butanoic acid A solution of 430 mg (1.5 mmol) of 5-hydroxy-2-methyl-1-(phenylmethyl)-1H-indole-3-acetamide (Example 2, Part D) in 50 mL of DMSO was treated with 60 mg (1.5 mmol) of 60% NaH/mineral oil, and then with 0.26 mL (1.8 mmol) of benzyl bromide. The mixture was stirred 1.5 hours at room temperature, 85° C. for 1.5 hours, and room temperature for 16 hours. It was diluted with water, extracted with EtOAc, the EtOAc solution washed with water, saturated NaCl solution, dried ($Na_2SO_4$), and concentrated at reduced pressure. The residue was chromatographed on silica ($CH_2Cl_2 \to 3\%$ MeOH/$CH_2Cl_2$) to give 315 mg (51% yield) of 4-[[3-(2-amino-2-oxoethyl)-2-methyl-1-(phenylmethyl)-1H-indol-5-yl]oxy]butanoic acid ethyl ester. This material was stirred with 1 mL of 5N NaOH in 15 mL of EtOH for 20 hours. The mixture was acidified with 5N HCl, extracted with EtOAc, the EtOAc solution washed with saturated NaCl solution and dried ($Na_2SO_4$). On concentrating the EtOAc solution, a precipitate formed and was collected to give 245 mg (38% yield) of 4-[[3-(2-amino-2-oxoethyl)-2-methyl-1-(phenylmethyl)-1H-indol-5-yl]oxy]butanoic acid, mp, 218°–221° C.

Analyses: Calc'd for $C_{22}H_{24}N_2O_4$: C, 69.46; H, 6.36 N, 7.36. Found: C, 68.35; H, 6.36; N, 7.00.

Example 23

Preparation of 5-[[3-(2-Amino-2-oxoethyl)-2-methyl-1-(phenylmethyl)-1H-indol-5-yl]oxy] pentanoic acid As described in Example 23, 125 mg (0.43 mmol) off 5-hydroxy-2-methyl-1-(phenylmethyl)-1H-indole-3-acetamide (Example 2), 30 mg of 60% NaH/mineral oil and 0.1 mL of 5-bromopentanoic acid methyl ester in 15 mL of DMSO were reacted to give 80 mg of 5-[[3-(2-amino-2-oxoethyl)-2-methyl-1-(phenylmethyl)-1H-indol-5-yl]oxy] pentanoic acid methyl ester, after chromatography on silica (eluted with $CH_2Cl_2 \to 2\%$ MeOH/$CH_2Cl_2$). This material in 5 mL of THF and 15 mL of EtOH was treated with 2 mL of 2N NaOH and the mixture stirred for 18 hours. After acidifying with 5N HCl, the mixture was extracted with EtOAc, the EtOAc solution washed with saturated NaCl solution, dried ($Na_2SO_4$), and concentrated at reduced pressure. The residue was dissolved in MeOH/$CH_2Cl_2$, concentrated and diluted with ether to give 80 mg (100% yield) of 5-[[3-(2-amino-2-oxoethyl)-2-methyl-1-(phenylmethyl)-1H-indol-5-yl]oxy]pentanoic acid, mp, 168°–169° C.

Analyses: Calc'd for $C_{23}H_{26}N_2O_4$: C, 70.03; H, 6.64; N, 7.10. Found: C, 43.53; H, 4.20; N, 4.31.

Example 24

4-[[3-(2-Amino-2-oxoethyl)-2-chloro-1-(phenylmethyl)-1H-indole-5-yl]oxy]butanoic acid A solution of 140 mg (0.43 mmol) of 2-chloro-5-methoxy-1-(phenylmethyl)-1H-indole-3-acetamide (Example 11) in 20 mL of methylene chloride was treated with 2 mL of 1M $BBr_3$/$CH_2Cl_2$, stirred for 1.5 hours, stirred with aqueous HCl, the $CH_2Cl_2$ solvent separated, and washed with water, saturated NaCl solution and dried ($Na_2SO_4$). On concentrating at reduced pressure, there was obtained 140 mg of crude 2-chloro-5-hydroxy-1-(phenylmethyl)-1H-indole-3-acetamide. This material was dissolved in 15 mL of DMSO, 20 mg of 60% NaH/mineral oil added, and after 5 minutes, 0.1 mL of ethyl 4-bromobutyrate was added. The reaction mixture was heated by oil bath at 70° C. for 70 minutes. After cooling, the mixture was diluted with water, extracted with EtOAc, the EtOAc solution washed with water, saturated NaCl solution and dried ($Na_2SO_4$). After concentrating, a residue was obtained that was chromatographed on silca (eluted with $CH_2Cl_2 \to 3\%$ MeOH/$CH_2Cl_2$) to give 105 mg of 4-[[3-(2-amino-2-oxoethyl)-2-chloro-1-(phenylmethyl)-1H-indole-5-yl]oxy]butanoic acid ethyl ester. This ester (105 mg) was dissolved in 15 mL of EtOH, 1 mL of 5N NaOH added, and the solution stirred for 18 hours. The mixture was made acidic with 5N HCl, and extracted with EtOAc. The EtOAc solution was washed with saturated NaCl solution, dried ($Na_2SO_4$) and concentrated at reduced pressure. The residue was dissolved in MeOH/$CH_2Cl_2$, the solution concentrated, to give 75 mg (80% yield) of 4-[[3-(2-amino-2-oxoethyl)-2-chloro-1-(phenylmethyl)-1H-indol-5-yl]oxy]butanoic acid, mp, 198°–200° C.

Analyses: Calc'd for $C_{21}H_{21}ClN_2O_4$: C, 62.92; H, 5.28; N, 6.99. Found: C, 58.94; H, 4.97; N, 6.41.

Example 25

Preparation of 3-[[3-(2-Amino-2-oxoethyl)-2-methyl-1-(phenylmethyl)-1H-indol-5-yl]amino] propanoic acid methyl ester A solution of 147 mg (0.5 mmol) of 5-amino-2-methyl-1-(phenylmethyl)-1H-indole-3-acetamide (Example 18) and 2 mL of methyl acrylate in 5 mL of MeOH was stirred for 65 hours, then concentrated at reduced pressure. The residue was chromatographed on silica and eluted with a gradient (EtOAc→5% MeOH/EtOAC) to give a major product and a minor product in the later fractions. The major product was 105 mg (55% yield) of 3-[[3-(2-amino-2-oxoethyl)-2-methyl-1-(phenylmethyl)-1H-indol-5-yl]amino]propanoic acid methyl ester.

Analyses: Calc'd for $C_{22}H_{25}N_3O_3$: C, 69.64; H, 6.64 N, 11.07. Found: C, 69.87; H, 6.39; N, 11.10.

Example 26

Preparation of 3,3'-[[3-(2-Amino-2-oxoethyl)-2-methyl-1-(phenylmethyl)-1H-indol-5-yl]imino]bis [propanoic acid]dimethyl ester From the chromatography of the reaction products obtained in Example 25, the later fractions contained the minor product, 3,3'-[[3-(2-amino-2-oxoethyl)-2-methyl-1-(phenylmethyl)-1H-indol-5-yl]imino]bis[propanoic acid] dimethyl ester, which, after drying, weighed 52 mg.

Example 27

Preparation of 3-[[3-(2-Amino-2-oxoethyl)-2-methyl-1-(phenylmethyl)-1H-indol-5-yl]amino] propanoic acid One mL of 1N NaOH was added to a solution of 110 mg (0.3 mmol) of 3-[[3-(2-amino-2-oxoethyl)-2-methyl-1-(phenylmethyl)-1H-indol-5-yl]amino]propanoic acid methyl ester (Example 26) in 5 mL of MeOH, stirred 1.0 hour, then 1 mL of 1N NaOH was added and the mixture stirred 0.5 hour. Water was added, then 2 mL of 1N HCl, and the mixture extracted with EtOAc. This was dried (MgSO$_4$) and concentrated at reduced pressure to give 21 mg (20% yield) of 3-[[3-(2-amino-2-oxoethyl)-2-methyl-1-(phenylmethyl)-1H-indol-5-yl]amino]propanoic acid.

Example 28

Preparation of 3-[[3-(2-Amino-2-oxoethyl)-2-methyl-1-(phenylmethyl)-1H-indol-5-yl]amino] propanoic acid hydrazide Hydrazine was added to 151 mg (0.4 mmol) of 3-[[3-(2-amino-2-oxoethyl)-2-methyl-1-(phenylmethyl)-1H-indol-5-yl]amino]propanoic acid methyl ester in 5 mL of MeOH and the mixture heated at reflux for 1.0 hour and stirred at room temperature for 16 hours. After diluting with water, the mixture was extracted with EtOAc, the EtOAc solution washed with saturated NaCl solution, dried (MgSO$_4$) and concentrated at reduced pressure.

Example 29

Preparation of 6-Methoxy-2-methyl-1-(phenylmethyl)-1H-indole-3-acetamide

A. 1-[2-(tert-Butoxycarbonylamino)-4-methoxyphenyl]-2-propanone. 12 g (87 mmol) of 5-methoxy-2-methylaniline was treated by the method in Example 1, Part A, with 19 g (87 mmol)of di-tert-butyl dicarbonate to give on concentrating a reaction mixture containing 16.4 g (80% yield) of N-tert-butoxycarbonyl-5-methoxy-2-methylaniline. This material (69 mmol) was reacted with 106 mL of 1.3M sec-butyl lithium in cyclohexane and then 7.1 g (69 mmol) of N-methoxy-N-methylacetamide (as described in Example 9, Part B) to give after chromatography on silica, eluting with 33% EtOAc/hexane, 13.8 g (72% yield) of 1-[2-(tert-butoxycarbonylamino-4-methoxyphenyl]-2-propanone.

Analysis: Calc d for $C_{15}H_{21}N_2O_4$: C, 64.50; H, 7.58; N, 5.01. Found: C, 63.80; H, 7.32; N, 5.48.

B. 6-Methoxy-2-methyl-1-(phenylmethyl)-1H-indole-3-glyoxylic acid amide. Using the method in Example 9, Part C, 13.7 g 49 mmol) of 1-[2-(tert-butoxycarbonylamino)-4-methoxyphenyl]-2-propanone was reacted with 20 mL of trifluoroacetic and the product chromatographed on silica eluting with 20% EtOAc/hexane. There was obtained 4.8 g (61% yield) of crude 6-methoxy-2-methyl-1H-indole. By the method in Example 6, Part A, this maternal (30 mmol) was treated with 1.2 g (30 mmol) of 60% NaH/mineral oil and 3.6 mL of benzyl bromide in DHF to give after chromatography on silica (eluting with 25% EtOAc/hexane) 4.77 g (63% yield) of 6-methoxy-2-methyl-1-(phenylmethyl)-1H-indole. By the method in Example 16, Part C, 1.97 g (8 mmol) of 6-methoxy-2-methyl-1-(phenylmethyl)-1H-indole was reacted with 0.73 mL (8.4 mmol) of oxalyl chloride and then ammonia to give 0.875 g (24% yield) of 6-methoxy-2-methyl-1-(phenylmethyl)-1H-indole-3-glyoxylic acid amide from EtOAc, mp, 230°–234° C.

Analysis: Calc'd for $C_{19}H_{18}N_2O_3$: C, 70.79; H, 5.63; N, 8.69. Found: C, 70.11; H, 5.71; N, 8.70.

C. 6-Methoxy-2-methyl-1-(phenylmethyl)-1H-indole-3-glycolic acid amide. Using EtOH as a solvent, 4.15 g (12.9 mmol) of 6-methoxy-2-methyl-1-(phenylmethyl)-1H-indole-3-glyoxylic acid amide (Example 16) was reacted with 0.605 g (16 mmol) of NaBH$_4$ by the method used in Example 17, Part A, and the crude product was washed with EtOAc and water to give 2.6134 g (63%) of 6-methoxy-2-methyl-1-(phenylmethyl)-1H-indole-3-glycolic acid amide, mp, 196°–198° C.

Analysis: Calc'd for $C_{19}H_{20}N_2O_2$: C, 70.35; H, 6.22; N, 8.64. Found: C, 70.49; H, 6.23; N, 8.85.

D. 6-Methoxy-2-methyl-1-(phenylmethyl)-1H-indole-3-acetamide. Using the method in Example 17, Part B, 720 mg (2.2 mmol) of 6-methoxy-2-methyl-1-(phenylmethyl)-1H-indole-3-glycolic acid amide, 0.4 mL (2.5 mmol) of triethylsilane, and 10 mL of trifluoroacetic acid were reacted and the product chromatographed on silica (eluting with 33% EtOAc/hexane) and crystallized from methylene chloride/MeOH to give 164 mg (24% yield) of 6-methoxy-2-methyl-1-(phenylmethyl)-1H-indole-3-acetamide, mp, 136°–139° C.

Analysis: Calc'd for $C_{19}H_{20}N_2O_3$: C, 74.00; H, 6.54; N, 9.08. Found: C, 73.72; H, 6.57; N, 9.00.

Example 30

Preparation of 6-Hydroxy-2-methyl-1-(phenylmethyl)-1H-indole-3-acetamide

To a solution of 1.53 g (5 mmol) of 6-methoxy-2-methyl-1-(phenylmethyl)-1H-indole-3-acetamide was added 20 mL (20 mmol) of 1M BBr$_3$ in methylene chloride and the mixture stirred for 3 hours. Water was added and the mixture extracted with EtOAc. The EtOAc solution was washed with a NaCl solution, dried (MgSO$_4$), and concentrated at reduced pressure. The residue was chromatographed on silica and the product eluted with 5% MeOH/methylene chloride to give 658 mg (45% yield) of 6-hydroxy-2-methyl-1-(phenylmethyl)-1H-indole-3-acetamide, mp, 174°–179° C.

Analysis: Calc'd for $C_{18}H_{18}N_2O_2$: C, 73.45; H, 6.16; N, 9.52. Found: C, 72.43; H, 6.08; N, 9.92.

Example 31

Preparation of 4-[[3-(2-Amino-2-oxoethyl)-2-methyl-1-(phenylmethyl)-1H-indol-6-yl]oxy]butanoic acid ethyl ester A solution of 294 mg (1 mmol) of 6-hydroxy-2-methyl-1-(phenylmethyl)-1H-indole-3-acetamide was treated with 40 mg (1 mmol) of 60% NaH/mineral oil and after 1 hours, 0.15 mL (1 mmol) of ethyl 4-bromobutyrate was added. The mixture was stirred for 2 hours, diluted with water and extracted with EtOAc. The EtOAc solution was washed with NaCl solution, dried (MgSO$_4$), and concentrated at reduced pressure. The residue was chromatographed on silica eluting with EtOAc to give (after crystallizing from CH$_2$Cl$_2$/MeOH/hexane, 228 mg (76% yield) of 4-[[3-(2-amino-2-oxoethyl)-2-methyl-1-(phenylmethyl)-1H-indol-6-yl]oxy]butanoic acid ethyl ester, mp, 126°–133° C.

Analysis: Calc'd for C$_{24}$H$_{28}$N$_2$O$_4$: C, 70.57; H, 6.91; N, 6.86. Found: C, .70.47; H, 6.97; N, 6.80.

Example 32

Preparation of 4-[[3-(2-Amino-2-oxoethyl)-2-methyl-1-(phenylmethyl)-1H-indol-6-yl]oxy]butanoic acid A solution of 100 mg (0.245 mmol) of 4-[[3-(2-amino-2-oxoethyl)-2-methyl-1-(phenylmethyl)-1H-indol-6-yl]oxy]butanoic acid ethyl ester and 2 mL of 1N NaOH in 5 mL of EtOH was stirred for 1.5 hours, diluted with water and extracted with EtOAc. The aqueous layer was made acidic to pH 6 with 1N HCl and extracted with EtOAc, the EtOAc dried (MgSO$_4$), and concentrated at reduced pressure. The residue was crystallized from MeOH/CH$_2$Cl$_2$ to give 44 mg (47% yield) of 4-[[3-(2-amino-2-oxoethyl)-2-methyl-1-(phenylmethyl)-1H-indol-6-yl]oxy]butanoic acid, mp, 180°–184° C.

Analysis: Calc'd for C$_{22}$H$_{24}$N$_2$O$_4$: C, 69.46; H, 6.36; N, 7.36. Found: C, 69.68; H, 6.38; N, 6.37.

Example 33

Preparation of 5-[[3-(2-Amino-2-oxoethyl)-2-methyl-1-(phenylmethyl)-1H-indol-6-yl]oxy]pentanoic acid ethyl ester Using the procedure in Example 33, 147 mg (0.5 mmol) of 6-hydroxy-2-methyl-1-(phenylmethyl)-1H-indole-3-acetamide was reacted with 20 mg (0.5 mmol) of 60% NaH/mineral oil and 0.08 mL (0.05 mmol) of ethyl 5-bromovalerate. After chromatography on silica (eluting first with 50% EtOAc/hexane, then EtOAc) and crystallization from MeOH/CH$_2$Cl$_2$ there was obtained 150 mg (71% yield) of 5-[[3-(2-amino-2-oxoethyl)-2-methyl-1-(phenylmethyl)-1H-indol-6-yl]oxy]pentanoic acid ethyl ester, mp, 123°–135° C.

Analysis: Calc'd for C$_{25}$H$_{30}$N$_2$O$_4$: C, 71.07; H, 7.16; N, 6.63. Found: C, 71.20; H, 7.15; N, 6.73.

Example 34

Preparation of 5-[[3-(2-Amino-2-oxoethyl)-2-methyl-1-(phenylmethyl)-1H-indol-6-yl]oxy]pentanoic acid As in Example 34, 100 mg (0.24 mmol) of 5-[[3-(2-amino-2-oxoethyl)-2-methyl-1-(phenylmethyl)-1N-indol-6-yl]oxy]pentanoic acid ethyl ester was hydrolyzed with 2 mL of 1N NaOH to give after crystallization from MeOH/CH$_2$Cl$_2$ 53 mg (56% yield) of 5-[[3-(2-amino-2-oxoethyl)-2-methyl-1-(phenylmethyl)-1H-indol-6-yl]oxy]pentanoic acid, mp, 103°–107° C.

Analysis: Calc'd for C$_{23}$H$_{26}$N$_2$O$_4$: C, 70.03; H, 6.64; N, 7.10. Found: C, 69.78; H, 6.81; N, 7.34.

Example 35

Preparation of 4-Methoxy-2-methyl-1-(phenylmethyl)-1H-indole-3-acetamide

A. N-tert-butoxycarbonyl-3-methoxy-2-methylaniline. By the method in Example 1, Part A, 25.8 g (188 mmol) of 3-methoxy-2-methylaniline was treated with 41 g (188 mmol) of di-tert-butyl dicarbonate to give by chromatography on silica (eluted with 25% EtOAc/hexane) 16.4 g (80% yield) of N-tert-butoxycarbonyl-3-methoxy-2-methylaniline.

Analysis: Calc'd for C$_{13}$H$_{19}$NO$_3$: C, 65.80; H, 8.07; N, 5.90. Found: C, 64.31; H, 7.76; N, 6.58.

B. 4-Methoxy-2-methyl-1H-indole. N-tert-Butoxycarbonyl-3-methoxy-2-methylaniline (43 g, 0.18 mol) was reacted with 280 mL (0.36 mol) of 1.3M sec-butyl lithium in cyclohexane and then 18.5 g (0.18 mol) of N-methoxy-N-methylacetamide as described in Example 9, Part B to give 39.5 g of a mixture of 1-[2-(tert-butoxycarbonylamino)-6-methoxyphenyl]-2-propanone and starting anilide. This mixture was dissolved in 100 mL of methylene chloride and 40 mL of trifluoroacetic acid and stirred for a total of 26 hours. The mixture was washed with water, dried (MgSO$_4$) and concentrated at reduced pressure. The residue was chromatographed on silica eluting with 20% EtOAc/hexane to give on crystallization from CH$_2$Cl$_2$/hexane 13.9 g of 4-methoxy-2-methyl-1H-indole, mp, 80°–86° C.

Analysis: Calc'd for C$_{10}$H$_{11}$NO: C, 74.51; H, 6.88; N, 8.69. Found: C, 74.41; H, 7.08; N, 8.47.

C. 4-Methoxy-2-methyl-1H-indole-3-acetic acid ethyl ester. Using the procedure in Example 1, Part C, 13.9 g (186 mmol) of 4-methoxy-2-methyl-1H-indole, 54 mL (86 mmol) of 1.6M n-butyl lithium/hexane, and 86 mL (86 mmol) of 1M ZnCl$_2$/ether were reacted to give after silica chromatography (eluted with 20% EtOAc/hexane) 11.2 g (53% yield) of 4-methoxy-2-methyl-1H-indole-3-acetic acid ethyl ester, mp, 117°–121° C.

Analysis: Calc'd for C$_{14}$H$_{17}$NO$_3$: C, 68.00; H, 6.93; N, 5.66. Found: C, 68.29; H, 6.98; N, 5.73.

D. 4-Methoxy-2-methyl-1-(phenylmethyl)-1H-indole-3-acetic acid ethyl ester. Using the method in Example 16, Part B, 7.4 g (30 mmol) of 4-methoxy-2-methyl-1H-indole-3-acetic acid ethyl ester, 1.2 g (30 mmol) of 60% NaH/mineral oil and 3.6 mL (30 mmol) of benzyl bromide were reacted to give after chromatography on silica and crystallization from MeOH/hexane, 6.16 g (61% yield) of 4-methoxy-2-methyl-1-(phenylmethyl)-1H-indole-3-acetic acid ethyl ester, mp, 75°–80° C.

Analysis: Calc'd for C$_{21}$H$_{23}$NO$_3$: C, 74.75; H, 6.87; N, 4.15. Found: C, 74.93; H, 6.66; N, 4.02.

E. 4-Methoxy-2-methyl-1-(phenylmethyl)-1H-indole-3-acetic acid hydrazide. A solution of 2.8 g (8.3 mmol) of 4-methoxy-2-methyl-1-(phenylmethyl)-1H-indole-3-acetic acid ethyl ester and 10 mL of hydrazine in 40 mL of EtOH was heated to maintain reflux for 16 hours, diluted with water and extracted with EtOAc. The EtOAc solution was washed with NaCl solution, dried (MgSO$_4$), and concentrated at reduced pressure. The residue was crystallized from MeOH to give 2.0 g (75% yield) of 4-methoxy-2-methyl-1-(phenylmethyl)-1H-indole-3-acetic acid hydrazide, mp, 145°–147° C.

Analysis: Calc'd for $C_{19}H_{21}N_3O_2$: C, 70.56; H, 6.55; N, 12.99. Found: C, 70.82; H, 6.67; N, 13.16.

F. 4-Methoxy-2-methyl-1-(phenylmethyl)-1H-indole-3-acetamide. A mixture of 2.0 g (6.2 mmol) of 4-methoxy-2-methyl-1-(phenylmethyl)-1H-indole-3-acetic acid hydrazide and approximately 1 g of Raney Ni were heated at reflux temperature for 1 hour, cooled, methylene chloride added and filtered. The filtrate was concentrated at reduced pressure and the residue chromatographed on silica eluting with 5% MeOH/EtOAc to give 1.5 g (79% yield) of 4-methoxy-2-methyl-1-(phenylmethyl)-1H-indole-3-acetamide, mp, 145°–146° C.

Analysis: Calc'd for $C_{19}H_{20}N_2O_2$: C, 74.08; H, 6.54; N, 9.08. Found: C, 75.09; H, 6.48; N, 9.20.

Example 36

Preparation of 4-Hydroxy-2-methyl-1-(phenylmethyl)-1H-indole-3-acetamide

A solution of 1.45 g (4.7 mmol) of 4-methoxy-2-methyl-1-(phenylmethyl)-1H-indole-3-acetamide and 14.1 mL (14.1 mmol) of 1M BBr$_3$ in methylene chloride was reacted as described in Example 2, Part C to give after chromatography on silica (eluted with EtOAc/hexane, then EtOAc) 908 mg (66% yield) of 4-hydroxy-2-methyl-1-(phenylmethyl)-1H-indole-3-acetamide, mp, 200°–208° C.

Analysis: Calc'd for $C_{18}H_{18}N_2O_2$: C, 73.45; H, 6.16; N, 9.52. Found: C, 73.70; H, 6.420; N, 9.52.

Example 37

Preparation of 4-[[3-(2-Amino-2-oxoethyl)-2-methyl-1-(phenylmethyl)-1H-indol-4-yl]oxy] butanoic acid ethyl ester A solution of 294 mg (1 mmol) of 4-hydroxy-2-methyl-1-(phenylmethyl)-1H-indole-3-acetamide was treated with 40 mg mmol) of 60% NaH/mineral oil and after 1 hour, 0.15 mL (1 mmol) of ethyl 4-bromobutyrate was added. The mixture was stirred for 2 hours, diluted with water and extracted with EtOAc. The EtOAc solution was washed with NaCl solution, dried (MgSO$_4$), and concentrated at reduced pressure. The residue was crystallized from MeOH/hexane to give a total of 235 mg (58% yield) of 4-[[3-(2-amino-2-oxoethyl)-2-methyl-1-(phenylmethyl)-1H-indol-4-yl]oxy] butanoic acid ethyl ester, mp, 115°–116° C.

Analysis: Calc'd for $C_{24}H_{28}N_2O_4$: C, 70.57; H, 6.91; N, 6.86. Found: C, 70.68; H, 6.97; N, 7.02.

Example 38

Preparation of 4-[[3-(2-Amino-2-oxoethyl)-2-methyl-1-(phenylmethyl)-1H-indol-4-yl]oxy] butanoic acid A solution of 100 mg (0.245 mmol) of 4-[[3-(2-amino-2-oxoethyl)-2-methyl-1-(phenylmethyl)-1H-indol-4-yl]oxy] butanoic acid ethyl ester and 2 mL of 1N NaOH in 5 mL of EtOH was stirred for 3.0 hours, diluted with water and extracted with EtOAc. The aqueous layer was made acidic to pH 6 with 1N HCl and extracted with EtOAc, the EtOAc dried (MgSO$_4$), and on concentrating at reduced pressure a precipitate formed that was separated and washed with MeOH to give 40 mg (42% yield) of 4-[[3-(2-amino-2-oxoethyl)-2-methyl-1-(phenylmethyl)-1H-indol-4-yl]oxy] butanoic acid, mp, 192°–193° C.

Analysis: Calc'd for $C_{22}H_{24}N_2O_4$: C, 69.46; H, 6.36; N, 7.36. Found: C, 68.17; H, 6.05; N, 6.99.

Example 39

Preparation of 2-[[3-(2-Amino-2-oxoethyl)-2-methyl-1-(phenylmethyl)-1H-indol-4-yl]oxy]acetic acid methyl ester Using the procedure in Example 37 294 mg (1 mmol) of 4-hydroxy-2-methyl-1-(phenylmethyl)-1H-indole-3-acetamide was treated with 40 mg (1 mmol) of 60% NaH/ mineral oil and 0.10 mL (1 mmol) of methyl 2-bromoacetate to give, after silica chromatography (eluted with 50% EtOAc/hexane, then EtOAc, followed by 2% MeOH/ EtOAc), 278 mg (76% yield) of 2-[[3-(2-amino-2-oxoethyl)-2-methyl-1-(phenylmethyl)-1H-indol-4-yl]oxy]acetic acid methyl ester, mp, 206°–208° C.

Analysis: Calc'd for $C_{24}H_{22}N_2O_4$: C, 68.84; H, 6.05; N, 6.65. Found: C, 769.06; H, 5.87; N, 7.40.

Example 40

Preparation of 2-[[3-(2-Amino-2-oxoethyl)-2-methyl-1-(phenylmethyl)-1H-indol-4-yl]oxy]acetic acid A solution of 100 mg (0.245 mmol) of 2-[[3-(2-amino-2-oxoethyl)-2-methyl-1-(phenylmethyl)-1H-indol-4-yl]oxy] acetic acid methyl ester and 2 mL of 1N NaOH in 5 mL of EtOH was stirred for 2.0 hours, diluted with water and extracted with EtOAc. The aqueous layer was made acidic to pH 6 with 1N HCl and extracted with EtOAc, the EtOAc dried (MgSO$_4$), and concentrated at reduced pressure. The residue was crystallized from MeOH to give 54 mg (57% yield) of 2-[[3-(2-amino-2-oxoethyl)-2-methyl-1-(phenylmethyl)-1H-indol-4-yl]oxy]acetic acid, mp, 225°–227° C.

Analysis: Calc'd for $C_{20}H_{20}N_2O_4$: C, 68.17; H, 5.72; N, 7.95. Found: C, 68.35; H, 5.79; N, 7.94.

Example 41

Preparation of [3-[[3-(2-amino-2-oxoethyl)-2-methyl-1-(phenylmethyl)-1H-indol-5-yl]oxy]propyl] phosphonic acid A. [3-[[3-(2-Amino-2-oxoethyl)-2-methyl-1-(phenylmethyl)-1H-indol-5-yl]oxy]propyl]phosphonic acid dimethyl ester. Using the procedure described in Example 39, 147 mg (0.5 mmol) of 5-hydroxy-2-methyl-1-(phenylmethyl)-1H-indole-3-acetamide was reacted with 20 mg (0.5 mmol) of 60% NaH/mineral oil and then 80 mg (0.0 mmol) of 3-bromopropylphosphonic acid dimethyl ester. The final product was crystallized from MeOH/hexane to give 126 mg (57% yield) of [3-[[3-(2-amino-2-oxoethyl)-2-methyl-1-(phenylmethyl)-1H-indol-5-yl]oxy]propyl] phosphonic acid dimethyl ester, mp, 136°–138° C.

Analysis: Calc'd for $C_{23}H_{29}N_2O_5P$: C, 62.15; H, 6.58; N, 6.30. Found: C, 61.09; H, 6.71; N, 5.94.

B. [3-[[3-(2-Amino-2-oxoethyl)-2-methyl-1-(phenylmethyl)-1H-indol-5-yl]oxy]propyl]phosphonic acid. A solution of 100 mg (0.23 mmol) of [3-[[3-(2-amino-2-oxoethyl)-2-methyl-1-(phenylmethyl)-1H-indol-5-yl]oxy] propyl]phosphonic acid dimethyl ester and 0.24 mL (1.8 mmol) of bromotrimethylsilane in 2 mL of methylene chloride was stirred for 18 hours. The reaction mixture was concentrated at reduced pressure, 5 mL of MeOH added, stirred 0.5 hour, and concentrated. The residue was crystallized from EtOAc/MeCN/HOAc/H$_2$O to give 40 mg (42% yield) of [3-[[3-(2-amino-2-oxoethyl)-2-methyl-1-(phenylmethyl)-1H-indol-5-yl]oxy]propyl]phosphonic acid, mp, 201°–203° C.

Analysis: Calc'd for $C_{21}H_{25}N_2O_5P$: C, 60.57; H, 6.05; N, 6.73. Found: C, 60.53; H, 6.08; N, 6.74.

Example 42

Preparation of 2-Bromo-5-methoxy-1-(phenylmethyl)-1H-indole-3-acetamide

A. 2-Bromo-5-methoxy-1-(phenylmethyl)-1H-indole-3-acetic acid benzyl ester. N-Bromosuccinimide (450 mg, 2.5 mmol) was added to 910 mg (5 mmol) of 5-methoxy-1-(phenylmethyl)-1H-indole-3-acetic acid benzyl ester in 75 mL of carbon tetrachloride and the mixture stirred for 0 5 hour. After washing with Na$_2$S$_2$O$_3$ solution, water and saturated NaCl solution and drying (Na$_2$SO$_4$), the CCl$_4$ was removed at reduced pressure. The residue was chromatographed on silica (eluted with methylene chloride) and crystallized from ether/hexane to give 765 mg (67% yield) of 2-bromo-5-methoxy-1-(phenylmethyl)-1H-indole-3-acetic acid benzyl ester, mp, 89°–90° C.

Analysis: Calc'd for $C_{25}H_{22}BrNO_3$: C, 64.66; H, 4.78; N, 3.02. Found: C, 64.43; H, 4.75; N, 2.96.

B. 2-Bromo-5-methoxy-1-(phenylmethyl)-1H-indole-3-acetamide. A solution of 120 mg (0.26 mmol) of 2-bromo-5-methoxy-1-(phenylmethyl)-1H-indole-3-acetic acid benzyl ester and 2 mL of 0.67M (CH$_3$)$_2$AlNH$_2$/benzene in 20 mL of benzene was heated for 23.5 hours while adding additional aluminum reagent periodically. The mixture was poured onto ice, decomposed with 1N HCl, and extracted with EtOAc. The extract was washed with saturated NaCl solution, dried (Na$_2$SO$_3$) and concentrated at reduced pressure. The residue was chromatographed on silica eluting with a gradient, CH$_2$Cl$_2$→2% MeOH/CH$_2$Cl$_2$, to give 100 mg (100% yield) of 2-bromo-5-methoxy-1-(phenylmethyl)-1H-indole-3-acetamide mp, 172°–174° C.

Analysis: Calc'd for $C_{18}H_{17}BrN_2O_2$: C, 57.92; H, 4.59; N, 7.50; Br, 21.41. Found: C, 57.71; H, 4.56; N, 7.42; Br, 21.67.

Example 43

Preparation of 4-[[3-(2-Amino-2-oxoethyl)-2-bromo-1-(phenylmethyl)-1H-indol-5-yl]oxy] butanoic acid A solution of 600 mg (1.6 mmol) of 2-bromo-5-methoxy-1-(phenylmethyl)-1H-indole-3-acetamide (lot was contaminated with 2,4-dibromo-5-methoxy-1-(phenylmethyl)-1H-indole-3-acetamide) and 10 mL of 1M BBr$_3$/CH$_2$Cl$_2$ in 100 mL of CH$_2$Cl$_2$ was stirred for 2.5 hours, 100 mL of 1N HCl added, stirred well, and the CH$_2$Cl$_2$ layer separated. After washing and drying (Na$_2$SO$_4$), the solvent was removed at reduced pressure. The residue was chromatographed on silica and eluted with a gradient (1% MeOH/CH$_2$Cl$_2$→4% MeOH/CH$_2$Cl$_2$) to give in the early fractions 2,4-dibromo-5-hydroxy-1-(phenylmethyl)-1H-indole-3-acetamide (115 mg) and in the later fractions 2-bromo-5-hydroxy-1-(phenylmethyl)-1H-indole-3-acetamide (115 mg). The material from the later fractions (100 mg, 0.28 mmol) was dissolved in 20 mL of DMSO, 20 mg of 60% NaH/mineral was added, and after 10 minutes, 0.1 mL of ethyl 4-bromobutyrate was added. After heating for 1.25 hours at 85° C., the mixture was diluted with water, extracted with EtOAc, and the EtOAc solution washed with water, saturated NaCl solution, dried (Na$_2$SO$_4$), and concentrated at reduced pressure. The residue was chromatographed on silica (eluted with 1% MeOH/CH$_2$Cl$_2$→3% MeOH/CH$_2$Cl$_2$) to give 80 mg of 4-[[3-(2-amino-2-oxoethyl)-2-bromo-1-(phenylmethyl)-1H-indol-5-yl]oxy]butanoic acid ethyl ester as an oil. This material was dissolved in 20 mL of EtOH, 1 mL of 2N NaOH added, and the mixture stirred for 19 hours. After acidifying with 1N HCl, the mixture was extracted with EtOAc, the EtOAc solution washed with saturated NaCl solution, dried (Na$_2$SO$_4$), and concentrated at reduced pressure. The residue was crystallized from EtOH/ether to give 80 mg of 4-[[3-(2-amino-2-oxoethyl)-2-bromo-1-(phenylmethyl)-1H-indol-5-yl]oxy]-butanoic acid.

Analysis: Calc'd for $C_{21}H_{21}BrN_2O_4$: C, 56.64; H, 4.75; N, 6.29. Found: C, 42.71; H, 3.76; N, 4.50.

Example 44

Preparation of 5-Hydroxy-2-(methylthio)-1-(phenylmethyl)-1H-indole-3-acetamide

A solution of 600 mg (1.6 mmol) of 5-methoxy-2-(methylthio)-1-(phenylmethyl)-1H-indole-3-acetamide (Example 12) was reacted with 10 mL of 1M BBr$_3$/CH$_2$Cl$_2$ as described in Example 2, Part C, to give as crude product 440 mg (64% yield) of 5-hydroxy-2-(methylthio)-1-(phenylmethyl)-1H-indole-3-acetamide.

Analysis: Calc'd for $C_{18}H_{18}N_2O_2S$: C, 66.23; H, 5.56; N, 8.58; S, 9.82. Found: C, 66.45; H, 5.55; N, 8.29; S, 9.72.

Example 45

Preparation of 4-[[3-(2-Amino-2-oxoethyl)-2-(methylthio)-1-(phenylmethyl)-1H-indol-5-yl]oxy] butanoic acid ethyl ester A solution of 465 mg (1.4 mmol) of 5-hydroxy-2-(methylthio)-1-(phenylmethyl)-1H-indole-3-acetamide (Example 46), 60 mg (1.5 mmol) of 60% NaH/mineral oil and 0.25 mL (1.7 mmol) of ethyl 4-bromoburyrate was reacted as in Example 45. After washing the crude product with EtOH/ether, there was obtained 510 mg (83% yield) of 4-[[3-(2-amino-2-oxoethyl)-2-(methylthio)-1-(phenylmethyl)-1H-indol-5-yl]oxy]butanoic acid ethyl ester, mp, 109°–111° C.

Analysis: Calc'd for $C_{24}H_{28}N_2O_4S$: C, 65.43; H, 6.41; N, 0.36; S, 7.28. Found: C, 65.24; H, 6.44; N, 6.12; S, 7.30.

Example 46

Preparation of 4-[[3-(2-Amino-2-oxoethyl)-2-(methylthio)-1-(phenylmethyl)-1H-indol-5-yl]oxy] butanoic acid As described in Example 45, 245 mg (0.56 mmol) of 4-[[3-(2-amino-2-oxoethyl)-2-(methylthio)-1-(phenylmethyl)-1H-indol-5-yl]oxy]butanoic acid ethyl ester (Example 47) was hydrolyzed with 1 mL of 5N NaOH in 5 mL of THF and 15 mL of EtOH. The crude product was washed with EtOH/ether to give 195 mg (85% yield of 4-[[3-(2-amino-2-oxoethyl)-2-(methylthio)-1-(phenylmethyl)-1H-indol-5-yl]oxy]butanoic acid, mp, 187°–188° C.

Analysis: Calc'd for $C_{22}H_{24}N_2O_4S$: C, 64.05; H, 5.86; N, 6.79; S, 7.77. Found: C, 63.81; H, 5.89; N, 6.80; S, 7.66.

Example 47

Preparation of 5-(4-Amino-4-oxobutoxy)-2-(methylthio)-1-(phenylmethyl)-1H-indole-3-acetamide Ten mL of 0.6M $(CH_3)_2AlNH_2$/benzene was added to 200 mg (0.45 mmol) of 4-[[3-(2-amino-2-oxoethyl)-2-methylthio-1-(phenylmethyl)-1H-indol-5-yl]oxy]butanoic acid ethyl ester (Example 46) in 25 mL of benzene and the mixture heated at 50° C. for 1.75 hours. After cooling the mixture was decomposed with ice and 1N HCl added. The mixture was extracted with EtOAc, the EtOAc solution washed with saturated NaCl solution, dried ($Na_2SO_4$), and concentrated at reduced pressure. The residue was crystallized from EtOH/$CH_2Cl_2$ to give 155 mg (84% yield) of 5-(4-amino-4-oxobutoxyl-2-(methylthio)-1-(phenylmethyl)-1H-indole-3-acetamide, mp, 185° C.

Analysis: Calc'd for $C_{22}H_{25}N_3O_3S$: C, 64.21; H, 6.12; N, 10.21; S, 7.79. Found: C, 64.42; H, 6.54; N, 8.97; S, 7.11.

Example 48

Preparation of 5-Methoxy-2-methyl-1-tetradecyl-1H-indole-3-acetamide

A. 5-Methoxy-2-methyl-1-tetradecyl-1H-indole-3-acetic acid ethyl ester. Using the method described in Example 6, Part A, 2.0 g (8.12 mmol) of 5-methoxy-2-methyl-1H-indole-3-acetic acid ethyl ester was reacted with 0.325 g of 60% NaH/mineral oil and 1.84 g (8.1 mmol) of tetradecyl bromide to give after chromatography on silica (eluting with 15% EtOAc/hexane) 1.66 g (46% yield) of 5-methoxy-2-methyl-1-tetradecyl-1H-indole-3-acetic acid ethyl ester.

Analysis: Calc'd for $C_{28}H_{45}NO_3$: C, 75.80; H, 10.22; N, 3.16. Found: C, 75.93; H, 10.32; N, 3.28.

B. 5-Methoxy-2-methyl-1-tetradecyl-1H-indole-3-acetic acid. A solution of 1.60 g (3.6 mmol) of 5-methoxy-2-methyl-1-tetradecyl-1H-indole-3-acetic acid ethyl ester and 10 mL of 1N NaOH in 25 mL of MeOH was stirred 16 hours, made acidic with 1N HCl, and the precipitate filtered to give 1.36 g (90% yield) of 5-methoxy-2-methyl-1-tetradecyl-1H-indole-3-acetic acid, mp, 105°–107° C.

Analysis: Calc'd for $C_{26}H_{41}NO_3$: C, 75.40; H, 9.94; N, 3.37. Found: C, 76.96; H, 10.37; N, 3.57.

C. 5-Methoxy-2-methyl-1-tetradecyl-1H-indole-3-acetamide. Oxalyl chloride (1 mL) was added to 1.36 g (3.2 mmol) of 5-methoxy-2-methyl-1-tetradecyl-1H-indole-3-acetic acid in 50 mL of methylene chloride and 1 drop of DMF and after stirring for 1 hour, the reaction mixture was concentrated at reduced pressure. The residue was dissolved in 50 mL of THF and anhydrous ammonia bubbled in for 0.5 hour. After diluting with EtOAc, the mixture was washed with water, dried ($Na_2SO_4$), and concentrated. The residue was chromatographed on silica and eluted with 2% MeOH/methylene chloride to give 0.42 g (32% yield) of 5-methoxy-2-methyl-1-tetradecyl-1H-indole-3-acetamide, mp, 117°–118° C.

Analysis: Calc'd for $C_{26}H_{42}N_2O_3$: C, 75.32; H, 10.21; N, 6.76. Found: C, 74.41; H, 9.67; N, 7.67.

Example 49

Preparation of 4-[[2-Amino-2-oxoethyl)-2-methyl-1-tetradecyl-1H-indol-5-yl]oxy]butanoic acid A. 5-Hydroxy-2-methyl-1-tetradecyl-1H-indole-3-acetamide. A solution of 300 mg (0.75 mmol) of 5-methoxy-2-methyl-1-tetradecyl-1H-indole-3-acetamide (Example 14, Part C) in 30 mL of methylene chloride was treated with 2 mL of 1N $BBr_3$/$CH_2Cl_2$ and the mixture stirred for 3 hours. The mixture was poured into water and 100 mL of EtOAc and the organic layer separated, washed with $Na_2CO_3$ solution, dried ($Na_2SO_4$) and concentrated at reduced pressure to give approximately 300 mg of crude 5-hydroxy-2-methyl-1-tetradecyl-1H-indole-3-acetamide.

Analysis: Calc'd for $C_{25}H_{40}N_2O_2$: C, 74.96; H, 10.06; N, 6.99. Found: C, 74.51; H, 9.55; N, 8.31.

B. 4-[[2-Amino-2-oxoethyl)-2-methyl-1-tetradecyl-1H-indol-5-yl]oxy]butanoic acid ethyl ester. 5-Hydroxy-2-methyl-1-tetradecyl-1H-indole-3-acetamide. (300 mg, 0.75 mmol) was dissolved in 10 mL of DMF, 40 mg (1.0 mmol) of 60% NaH/mineral oil added, and the mixture stirred for 0.5 hour. Thereafter, 0.143 mL (1.0 mmol) of ethyl 4-bromobutyrate was added, the mixture stirred for 20 hours., diluted with water and extracted with EtOAc. The EtOAc solution was washed 4 times with water, dried ($Na_2SO_4$), and concentrated at reduced pressure. The residue was crystallized from EtOH/water to give 0.12 mg (31% yield) of 4-[[2-amino-2-oxoethyl)-2-methyl-1-tetradecyl-1H-indol-5-yl]oxy]-butanoic acid ethyl ester, mp, 77°–78° C.

Analysis: Calc'd for $C_{31}H_{50}N_2O_4$: C, 72.34; H, 9.79; N, 5.44. Found: C, 72.13; H, 9.63; N, 5.17.

C. 4-[[2-Amino-2-oxoethyl)-2-methyl-1-tetradecyl-1H-indol-5-yl]oxy]butanoic acid. A solution of 120 mg (0.233 mmol) of 4-[[2-amino-2-oxoethyl)-2-methyl-1-tetradecyl-1H-indol-5-yl]oxy]butanoic acid ethyl ester and 1 mL of 5N NaOH in 20 mL of MeOH was heated to maintain reflux for 1 hour, cooled and poured into 100 mL of water and made acidic with 5N HCl. The mixture was extracted with EtOAc, the EtOAc solution dried ($Na_2SO_4$), and concentrated at reduced pressure. The residue was crystallized from MeOH to give 50 mg (44% yield) of 4-[[2-amino-2-oxoethyl)-2-methyl-1-tetradecyl-1H-indol-5-yl]oxy]butanoic acid, mp, 159°–161° C.

Analysis: Calc'd for $C_{29}H_{46}N_2O_4$: C, 71.57; H, 9.53; N, 5.76. Found: C, 71.44; H, 9.39; N, 5.70.

Example 50

Preparation of [4-[[3-(2-Amino-2-oxoethyl)-1-hexyl-2-methyl-1-H-indol-5-yl]oxy]butanoic acid A. 1-Hexyl-5-methoxy-2-methyl-1H-indole-3-acetic acid ethyl ester. 5-Methoxy-2-methyl-1H-indole-3-acetic acid ethyl ester was dissolved in 25 mL of DMF and 0.3 g (7.5 mmol) of 60% NaH/mineral oil was added. After 0.25 hours, 1.1 mL (7.5 mmol) of hexyl iodide was added and the mixture stirred for 16 hours. The mixture was diluted with water, extracted with ethyl acetate and the ethyl acetate solution washed with water. After drying ($Na_2SO_4$), the solution was concentrated at reduced pressure and the residue chromatographed on silica gel (eluted with 5% EtOAc/toluene) to give 1.01 g (61% yield) of 1-hexyl-5-methoxy-2-methyl-1H-indole-3-acetic acid ethyl ester.

Analysis for $C_{20}H_{29}NO_3$: Calculated C, 74.75; H, 5.96; N, 4.36. Found C, 70.31; H, 8.68; N, 3.93.

B. 1-Hexyl-5-methoxy-2-methyl-1H-indole-3-acetamide. A 2M solution of Al(CH3)3/toluene (15 mL, 0.03 mol) was added to 1.61 g (0.03 mol) of ammonium chloride while slowly keeping the temperature at 5°–7° C. with an ice-water bath. The bath was removed, the mixture stirred for 0.5 hour and 1.01 g (3.05 mmol) of 1-hexyl-5-methoxy-2-methyl-1H-indole-3-acetic acid ethyl ester was added. After stirring for 16 hours, 10 mL of water was added cautiously and the mixture added to 1N HCl and a large volume of ethyl acetate. The organic layer was separated, washed with water, sodium bicarbonate solution and dried ($Na_2SO_4$). After removing the solvent at reduced pressure the residue was crystallized from MeOH/water to give 0.37 g (40% yield) of 1-hexyl-5-methoxy-2-methyl-1H-indole-3-acetamide, mp, 120°–121° C.

Analysis for $C_{18}H_{26}N_2O_2$: Calculated C, 71.49; H, 8.67; N, 9.26. Found C, 71.64; H, 8.54; N, 9.21.

C. 1-Hexyl-5-hydroxy-2-methyl-1H-indole-3-acetamide. A mixture of 1 mL of 1M $BBr_3$/methylene chloride and 0.24 g (0.79 mmol) of 1-hexyl-5-methoxy-2-methyl-1H-indole-3-acetamide in 20 mL of methylene chloride as stirred for 16 hours, diluted with ethyl acetate and washed twice with water. The solution was dried ($Na_2SO_4$) and the solvent removed at reduced pressure to give 0.23 g of crude 1-hexyl-5-hydroxy-2-methyl-1H-indole-3-acetamide.

D. [4-[[3-(2-Amino-2-oxoethyl)-1-hexyl-2-methyl-1-H-indol-5-yl]oxy]butanoic acid ethyl ester. 1-Hexyl-5-hydroxy-2-methyl-1H-indole-3-acetamide (230 mg, 0.8 mmol) was dissolved in 10 mL of DMF and 26 mg (0.8 mmol) of 60% NaH/mineral oil added. The mixture was stirred for 1 hour, 0.115 mL (0.8 mmol) of ethyl 4-bromobutyrate added and stirring continued for 96 hours. The mixture was diluted with water, extracted with ethyl acetate, the ethyl acetate washed with water and dried ($Na_2SO_4$). The solution was concentrated at reduced pressure and the residue chromatographed on silica gel (eluted with 3% MeOH/methylene chloride) to give 170 mg (53% yield of [4-[[3-(2-amino-2-oxoethyl)-1-hexyl-2-methyl-1-H-indol-5-yl]oxy]butanoic acid ethyl ester, mp, 69°–71° C.

Analysis for $C_{23}H_{34}N_2O_4$: Calculated C, 68.63; H, 8.51; N, 6.96. Found C, 68.90; H, 8.59; N, 6.80.

E. [4-[[3-(2-Amino-2-oxoethyl)-1-hexyl-2-methyl-1-H-indol-5-yl]oxy]butanoic acid. A mixture of 170 mg (0.42 mmol) of [4-[[3-(2-amino-2-oxoethyl)-1-hexyl-2-methyl-1-H-indol-5-yl]oxy]butanoic acid ethyl ester and 1 mL of 5N NaOH in 20 mL of MeOH was heated to maintain reflux for 2.5 hours, cooled, poured into water and made strongly acidic with 5N HCl. The mixture was extracted with ethyl acetate, dried ($Na_2SO_4$), concentrated at reduced pressure and the residue crystallized from MeOH. There was obtained 37 mg (24% yield) of [4-[[3-(2-amino-2-oxoethyl)-1-hexyl-2-methyl-1-H-indol-5-yl]oxy]butanoic acid. mp, 169°–170° C.

Analysis for $C_{21}H_{30}N_2O_4$: Calculated C, 67.35; H, 8.07; N, 7.48. Found C, 67.59; H, 8.06 N, 7.42.

Example 51

5-Methoxy-2-methyl-1-octyl-1H-indole-3-acetamide

A. 5-Methoxy-2-methyl-1-octyl-1H-indole-3-acetic acid ethyl ester. Using the procedure described in Example 50, Part A, 2.47 g (0.01 mol) of 5-methoxy-2-methyl-1H-indole-3-acetic acid ethyl ester was reacted with 0.48 g (0.012 mol) of 60% NaH/mineral oil and then 2.17 mL (0.012 mol) of iodooctane. The product was chromatographed on silica gel and eluted with 5% EtOAc/toluene to give 1.85 g (51% yield) of 5-methoxy-2-methyl-1-octyl-1H-indole-3-acetic acid ethyl ester as an oil.

Analysis for $C_{22}H_{33}NO_3$: Calculated C, 73.50; H, 9.25; N, 3.90. Found C, 73.47; H, 9.33; N, 3.83.

B. 5-Methoxy-2-methyl-1-octyl-1H-indole-3-acetic acid hydrazide. A mixture of 1.8 g (5 mmol) of 5-methoxy-2-methyl-1-octyl-1H-indole-3-acetic acid ethyl and 3 mL of hydrazine in 125 mL of ethanol was heated to maintain reflux for 16 hours. The mixture was poured into water, extracted with ethyl acetate, washed with water and dried ($Na_2SO_4$). After removing the solvent at reduced pressure the residue was crystallized from EtOH/water to give 1.29 g (75% yield) of 5-methoxy-2-methyl-1-octyl-1H-indole-3-acetic acid hydrazide, mp, 135°–136° C.

Analysis for $C_{20}H_{31}N_3O_2$: Calculated C, 69.53; H, 9.04; N, 12.16. Found C, 69.69; H, 9.07; N, 11.89.

C. 5-Methoxy-2-methyl-1-octyl-1H-indole-3-acetamide. A mixture of 1.27 g (3.68 mmol) of 5-methoxy-2-methyl-1-octyl-1H-indole-3-acetic acid hydrazide and 1 g of Raney Ni in 60 mL of ethanol was heated to maintain reflux for 3 hours, cooled, the solvent poured off the settled catalyst, treated with filter aid and filtered. The filtrate was concentrated to give 1.03 g (85% yield) of 5-methoxy-2-methyl-1-octyl-1H-indole-3-acetamide, mp, 96°–98° C.

Analysis for $C_{20}H_{30}N_2O_2$: Calculated C, 72.69; H, 9.15; N, 8.48. Found C, 72.48; H, 9.26; N, 8.33.

Example 52

Preparation of [4-[[3-(2-Amino-2-oxoethyl)-2-methyl-1-octyl-H-indol-5-yl]oxy]butanoic acid A. 5-Hydroxy-2-methyl-1-octyl-1H-indole-3-acetamide. A solution of 1.03 g (3.1 mmol) of 5-methoxy-2-methyl-1-octyl-1H-indole-3-acetamide and 5 mL of 1M $BBr_3$/methylene chloride in 50 mL of methylene chloride was stirred for 24 hours, poured into water and 150 mL of ethyl acetate added. The organic layer was separated, washed with $NaHCO_3$ solution, dried ($Na_2SO_4$) and concentrated at reduced pressure. The residue was chromatographed on silica gel by eluting with 5% MeOH/methylene chloride to give 316 mg (32% yield) of 5-hydroxy-2-methyl-1-octyl-1H-indole-3-acetamide.

B. [4-[[3-(2-Amino-2-oxoethyl)-2-methyl-octyl-1-H-indol-5-yl]oxy]butanoic acid ethyl ester. 5-Hydroxy-2-methyl-1-octyl-1H-indole-3-acetamide (316 mg, 1.0 mmol) was reacted with 240 mg (1.0 mmol) of 60% NaH/mineral and then 0.143 mL (1 mmol) of ethyl 4-bromobutyrate as described in Example 50, Part D. The product was chromatographed on silica gel (eluted with 3% MeOH/methylene chloride) to give 230 mg (53% yield) of [4-[[3-(2-amino-2-oxoethyl)-2-methyl-octyl-1-H-indol-5-yl]oxy]butanoic acid ethyl ester, mp, 80°–85° C.

Analysis for $C_{25}H_{38}N_2O_4$ Calculated C, 69.74; H, 8.90; N, 6.51. Found C, 67.56; H, 9.01; N, 5.95.

C. [4-[[3-(2-Amino-2-oxoethyl)-2-methyl-octyl-1-H-indol-5-yl]oxy]butanoic acid. Using the method of Example 1, Part E, 230 mg (0,53 mmol) of [4-[[3-(2-amino-2-oxoethyl)-2-methyl-octyl-1-H-indol-5-yl]oxy]butanoic acid ethyl ester was hydrolyzed with 2 mL of 5N NaOH to give after crystallization from MeOH, 97 mg (45% yield) of [4-[[3-(2-amino-2-oxoethyl)-2-methyl-octyl-1-H-indol-5-yl]oxy]butanoic acid, mp, 164°–165° C.

Analysis for $C_{23}H_{34}N_2O_4$: Calculated C, 68.63; H, 8.51; N, 6.96. Found C, 66.40; H, 8.30; N, 6.82.

Example 53

Preparation of [4-[[3-(2-Amino-2-oxoethyl)-1-decyl-2-methyl-1-H-indol-5-yl]oxy]butanoic acid A. 1-Decyl-5-hydroxy-2-methyl-1H-indole-3-acetamide. A mixture of 5 mL of 1M $BBr_3$/methylene chloride and 0.98 g (2.73 mmol) of 1-decyl-5-methoxy-2-methyl-1H-indole-3-acetamide in 40 mL of methylene chloride was reacted as described in Example 50, Part C to give 0.81 g (60% yield) of crude 1-decyl-5-hydroxy-2-methyl-1H-indole-3-acetamide.

B. [4-[[3-(2-Amino-2-oxoethyl)-1-decyl-2-methyl-1-H-indol-5-yl]oxy]butanoic acid ethyl ester. 1-Decyl-5-hydroxy-2-methyl-1H-indole-3-acetamide (810 mg, 3.35 mmol) was reacted with 96 mg (2.4 mmol) of 60% NaH/mineral oil and then 0.32 mL (2.4 mmol) of ethyl 4-bromobutyrate as described in Example 50, Part D to give a product that was chromatographed on silica gel (eluted with 3% MeOH/methylene chloride) to give 590 mg (55% yield) of [4-[[3-(2-amino-2-oxoethyl)-1-decyl-2-methyl-1-H-indol-5-yl]oxy]butanoic acid ethyl ester, mp, 93°–95° C.

Analysis for $C_{27}H_{42}N_2O_4$: Calculated C, 70.71; H, 9.23; N, 6.11. Found C, 70.57; H, 9.03; N, 6.17.

C. [4-[[3-(2-Amino-2-oxoethyl)-1-decyl-2-methyl-1-H-indol-5-yl]oxy]butanoic acid. A mixture of 590 mg (1.3 mmol) of [4-[[3-(2-amino-2-oxoethyl)-1-decyl-2-methyl-1-H-indol-5-yl]oxy]butanoic acid ethyl ester and 1.5 mL of 5N NaOH in 20 mL of MeOH was heated to maintain reflux for 2.5 hours, cooled, poured into water and made strongly acidic with 5N HCl. The precipitate was filtered and recrystallized from MeOH. There was obtained 430 mg (77% yield) of [4-[[3-(2-amino-2-oxoethyl)-1-decyl-2-methyl-1-H-indol-5-yl]oxy]butanoic acid, mp, 163°–165° C.

Analysis for $C_{25}H_{38}N_2O_4$: Calculated C, 69.74; H, 8.90; N, 6.51. Found C, 70.63; H, 8.83; N, 6.98.

Example 54

Preparation of [4-[[3-(2-Amino-2-oxoethyl)-1-cyclohexyl-2-methyl-1-H-indol-5-yl]oxy]butanoic acid A. 1-Cyclohexyl-5-hydroxy-2-methyl-1H-indole-3-acetamide. A mixture of 2 mL of 1M $BBr_3$/methylene chloride and 330 mg (1.05 mmol) of 1-cyclohexyl-5-methoxy-2-methyl-1H-indole-3-acetamide in 25 mL of methylene chloride was reacted as described in Example 50, Part C to give 300 mg of crude 1-cyclohexyl-5-hydroxy-2-methyl-1H-indole-3-acetamide.

Analysis for $C_{18}H_{24}N_2O_2$: Calculated C, 71.97; H, 8.05 N, 9.33. Found C, 69.14; H, 7.60; N, 8.69.

B. [4-[[3-(2-Amino-2-oxoethyl)-cyclohexyl-2-methyl-1-H-indol-5-yl]oxy]butanoic acid ethyl ester. 1-Cyclohexyl-5-hydroxy-2-methyl-1H-indole-3-acetamide (300 mg, 1.0 mmol) was reacted with 40 mg (1.0 mmol) of 60% NaH/mineral oil and then 0.143 mL (1.0 mmol) of ethyl 4-bromobutyrate as described in Example 50, Part D to give a product that was chromatographed on silica gel (eluted with 2% MeOH/methylene chloride) to give 190 mg (46% yield) of [4-[[3-(2-amino-2-oxoethyl)-1-cyclohexyl-2-methyl-1-H-indol-5-yl]oxy]butanoic acid ethyl ester, mp, 92°–94° C.

Analysis for $C_{24}H_{34}N_2O_4$: Calculated C, 69.54; H, 8.27; N, 6.76. Found C, 69.72; H, 8.33; N, 6.70.

C. [4-[[3-(2-Amino-2-oxoethyl)-1-cyclohexyl-2-methyl-1-H-indol-5-yl]oxy]butanoic acid. A mixture of 190 mg (0.46 mmol) of [4-[[3-(2-amino-2-oxoethyl)-1-decyl-2-methyl-1-H-indol-5-yl]oxy]butanoic acid ethyl ester and 2 mL of 5N NaOH in 20 mL of MeOH was heated to maintain reflux for 2.5 hours, cooled, poured into water and made strongly acidic with 5N HCl. The precipitate was filtered and recrystallized from MeOH. There was obtained 50 mg (28% yield) of [4-[[3-(2-amino-2-oxoethyl)-1-cyclohexyl-2-methyl-1-H-indol-5-yl]oxy]butanoic acid. mp, 212°–214° C.

Analysis for $C_{22}H_{30}N_2O_4$: Calculated C, 68.37; H, 7.82; N, 7.25. Found C, 68.19; H, 7.54; N, 7.02.

Example 55

Preparation of [3-[[3-(2-Amino-2-oxoethyl)-1-([1,1'-biphenyl]-2-ylmethyl)-2-methyl-1H-indol-5-yl]oxy] propyl]phosphonic acid A. 1-([1,1'-Biphenyl]-2-ylmethyl)-5-methoxy-2-methyl-1H-indole-3-acetic acid ethyl ester. 5-Methoxy-2-methyl-1H-indole-3-acetic acid ethyl ester (988 mg, 4 mmol) was added to 160 mg (4 mmol) of NaH/mineral oil (previously washed with hexane), the mixture stirred for 0.5 hours and 0.74 mL (4 mmol) of 2-(bromomethyl)biphenyl added. After 2 hours, water was added and the mixture extracted with ethyl acetate. The ethyl acetate was washed with brine, dried ($MgSO_4$) and concentrated at reduced pressure. The residue was chromatographed on silica gel eluting with 20% EtOAc/hexane to give 1.18 g (72% yield) of 1-([1,1'-biphenyl]-2-ylmethyl)-5-methoxy-2-methyl-1H-indole-3-acetic acid ethyl ester as an oil.

B. 1-([1,1'-Biphenyl]-2-ylmethyl)-5-methoxy-2-methyl-1H-indole-3-acetamide. A mixture of 1.18 g (2.86 mmol) of 1-([1,1'-biphenyl]-2-ylmethyl)-5-methoxy-2-methyl-1H-indole-3-acetic acid ethyl ester and 3 mL of hydrazine in 20 mL of ethanol was heated to maintain reflux for 16 hours. After cooling, water was added and the mixture was extracted with ethyl acetate. The ethyl acetate solution was washed with brine, dried ($MgSO_4$), and concentrated to give 1.02 g of 1-([1,1'-biphenyl]-2-ylmethyl)-5-methoxy-2-methyl-1H-indole-3-acetic acid hydrazide. A mixture of 576 mg (1.44 mmol) of this material and 300 mg of Raney Ni in 20 mL of ethanol was heated to maintain reflux for 3 hours. After cooling the solvent was decanted and the Raney Ni washed twice with methylene chloride. The combined organic solvents were concentrated at reduced pressure and the residue chromatographed on silica gel and eluted with ethyl acetate to give 369 mg (67% yield) of 1-([1,1'-biphenyl]-2-ylmethyl)-5-methoxy-2-methyl-1H-indole-3-acetamide.

C. 1-([1,1'-Biphenyl]-2-ylmethyl)-5-hydroxy-2-methyl-1H-indole-3-acetamide. A solution of 369 mg (0.96 mmol) of 1-([1,1'-biphenyl]-2-ylmethyl)-5-methoxy-2-methyl-1H-indole-3-acetamide and 4 mL of 1M $BBr_3$/methylene chloride in 20 mL of methylene chloride was stirred for 6 hours. The mixture was concentrated at reduced pressure, the residue dissolved in ethyl acetate, washed with water, brine and dried ($MgSO_4$). After concentrating at reduced pressure, the residue was chromatographed on silica gel and eluted with EtOAc to give 295 mg (85% yield) of 1-([1,1'-biphenyl]-2-ylmethyl)-5-hydroxy-2-methyl-1H-indole-3-acetamide.

D. [3-[[3-(2-Amino-2-oxoethyl)-1-([1,1'-biphenyl]-2-ylmethyl)-2-methyl-1H-indol-5-yl]oxy]propyl]phosphonic acid dimethyl ester. 1-([1,1'-Biphenyl]-2-ylmethyl)-5-hydroxy-2-methyl-1H-indole-3-acetamide (295 mg, 0.8 mmol) was added to 32 mg (0.8 mmol) of NaH/mineral oil in 10 mL of DMF, stirred 1 hour, 121 mg (0.8 mmol) of (3-bromopropyl)phosphonic acid dimethyl ester added and stirring maintained for 5.5 hours. The mixture was diluted with water, extracted with ethyl acetate, the ethyl acetate washed with brine, dried ($MgSO_4$) and concentrated. The residue was chromatographed on silica gel eluting with a gradient, EtOAc→10% MeOH/EtOAc to give 140 mg (34% yield) of [3-[[3-(2-amino-2-oxoethyl)-1-([1,1'-biphenyl]-2-ylmethyl)-2-methyl-1H-indol-5-yl]oxy]propyl]phosphonic acid dimethyl ester.

E. [3-[[3-(2-Amino-2-oxoethyl)-1-([1,1'-biphenyl]-2-ylmethyl)-2-methyl-1H-indol-5-yl]oxy]propyl]phosphonic acid. [3-[[3-(2-Amino-2-oxoethyl)-1-([1,1'-biphenyl]-2-ylmethyl)-2-methyl-1H-indol-5-yl]oxy]propyl]phosphonic acid dimethyl ester (130 mg, 0.25 mmol) and 0.3 mL (3 mmol) of trimethylsilyl bromide in 2 mL of methylene chloride was stirred for 16 hours, 5 mL of MeOH added, stirred 0.75 hours and concentrated at reduced pressure. The residue was crystallized from EtOAc/MeCN/HOAc/water to give 41 mg (33% yield) of [3-[[3-(2-amino-2-oxoethyl)-1-([1,1'-biphenyl]-2-ylmethyl-2-methyl-1H-indol-5-yl]oxy]propyl]phosphonic acid, mp, 200°–202° C.

Analysis for $C_{27}H_{29}N_2O_5P$: Calculated C, 65.84; H, 5.94; N, 5.69. Found C, 65.56; H, 5.85; N, 5.74.

Example 56

Preparation of 2-Ethyl-5-hydroxy-1-(phenylmethyl)-1H-indole-3-acetamide

2-Ethyl-5-methoxy-1-(phenylmethyl)-1H-indole-3-acetamide (5.05 g, 15.7 mmol) and 47 mL of 1M $BBr_3$ in 100 mL of methylene chloride was reacted as described in Example 56, Part C to give a product that was chromatographed on silica gel eluting with EtOAc to give 3.64 g (75% yield) of 2-ethyl-5-hydroxy-1-(phenylmethyl)-1H-indole-3-acetamide as a yellow foam.

Analysis for $C_{19}H_{20}N_2O_2$: Calculated C, 74.00; H, 6.54; N, 9.08. Found C, 73.55; H, 6.40; N, 8.73.

Example 57

Preparation of [4-[[3-(2-Amino-2-oxoethyl)-2-ethyl-1-(phenylmethyl)-1-H-indol-5-yl]oxy]butanoic acid ethyl ester 2-Ethyl-5-hydroxy-1-(phenylmethyl)-1H-indole-3-acetamide (308 mg, 1 mmol) was reacted with 40 mg (1 mmol) of 60% NaH/mineral oil and then with 0.15 mL (1 mmol) of ethyl 4-bromobutyrate as described in Example 56. Part D to give a product that was chromatographed on silica gel eluting with 50% EtOAc/hexane to give 231 mg (55% yield) of [4-[[3-(2-amino-2-oxoethyl)-2-ethyl-1-(phenylmethyl)-1-H-indol-5-yl]oxy]butanoic acid ethyl ester.

Analysis for $C_{25}H_{30}N_2O_4$: Calculated C, 71.07; H, 7.16; N, 6.63. Found C, 71.21; H, 7.24; N, 6.53.

Example 58

Preparation of [4-[[3-(2-amino-2-oxoethyl)-2-ethyl-1-(phenylmethyl)-1-H-indol-5-yl]oxy]butanoic acid A mixture of 200 mg (0.5 mmol) of [4-[[3-(2-amino-2-oxoethyl)-2-ethyl-1-(phenylmethyl)-1-H-indol-5-yl]oxy]butanoic acid ethyl ester and 4 mL of 1N NaOH in 10 mL of EtOH was stirred for 1.5 hours, diluted with water and extracted with EtOAc. The aqueous layer was made acidic to pH 5 with 1N HCl, extracted with EtOAc, the EtOAc solution washed with brine and dried (MgSO₄). The solvent was evaporated at reduced pressure, the residue stirred with ether/MeOH and the insoluble material filtered to give 120 mg (61% yield) of [4-[[3-(2-amino-2-oxoethyl)-2-ethyl-1-(phenylmethyl)-1-H-indol-5-yl]oxy]butanoic acid, mp, 196°–199° C.

Analysis for $C_{23}H_{26}N_2O_4$: Calculated C, 70.03; H, 6.64; N, 7.10. Found C, 69.96; H, 6.78; N, 6.85.

Example 59

Preparation of 2-Ethyl-5-(4-hydrazino-4-oxobutoxy)-1-(phenylmethyl-1H-indole-3-acetamide A mixture of 211 mg (0.05 mmol of [4-[[3-(2-amino-2-oxoethyl)-2-ethyl-1-(phenylmethyl)-1-H-indol-5-yl]oxy]butanoic acid ethyl ester and 1 mL of hydrazine in 5 mL of ethanol was heated to maintain reflux for 5 hours. The mixture was diluted with water, extracted with ethyl acetate, the ethyl acetate washed with brine, dried (MgSO₄), and concentrated at reduced pressure. The residue was stirred with MeOH and the insoluble material filtered to give 177 mg (87% yield) of 2-ethyl-5-(4-hydrazino-4-oxobutoxy)-1-(phenylmethyl)-1H-indole-3-acetamide, mp, 176°–179° C.

Analysis for $C_{23}H_{28}N_4O_3$: Calculated C, 67.63; H, 6.91; N, 13.72. Found C, 67.58; H, 7.01; N, 13.95.

Example 60

Preparation of 5-(4-Amino-4-oxobutoxy)-2-ethyl-1-(phenylmethyl)-1H-indole-3-acetamide A mixture of 150 mg (0.37 mmol) of 2-ethyl-5-(4-hydrazino-4-oxobutoxy)-1-(phenylmethyl)-1H-indole-3-acetamide and 200 mg of Raney Ni in 15 mL of ethanol was heated to maintain reflux for 2 hours. After cooling, the EtOH was poured off and the Raney Ni washed twice with methylene chloride. The combined washes were filtered, concentrated at reduced pressure and the residue chromatographed on silica eluting with EtOAc, then 10% MeOH/EtOAc to give 69 mg (47% yield) of 5-(4-amino-4-oxobutoxy)-2-ethyl-1-(phenylmethyl)-1H-indole-3-acetamide, mp 176°–179° C.

Analysis for $C_{23}H_{27}N_3O_3$: Calculated C, 70.20; H, 6.92; N, 10.68. Found C, 69.92; H, 7.13; N, 10.64.

Example 61

Preparation of [3-[[3-(2-Amino-2-oxoethyl)-2-ethyl-1-(phenylmethyl)-1H-indol-5-yl]oxy]propyl] phosphonic acid dimethyl ester 5-Hydroxy-2-ethyl-1-(phenylmethyl)-1H-indole-3-acetamide (308 mg, 1.0 mmol) was added to 40 mg (1.0 mmol) of NaH/mineral oil washed with hexanes) in 4 mL of DMF, stirred 0.5 hours, 196 mg (0.85 mmol) of (3-bromopropyl)phosphonic acid dimethyl ester added and stirring maintained for 6.5 hours. The mixture was diluted with water, extracted with ethyl acetate, the ethyl acetate washed with brine, dried (MgSO₄) and concentrated. The residue was chromatographed on silica gel eluting with EtOAc, 5% MeOH/EtOAc, then 10% MeOH/EtOAc to give 269 mg (59% yield) of [3-[[3-(2-amino-2-oxoethyl)-2-ethyl-1-(phenylmethyl)-1H-indol-5-yl]oxy]propyl]phosphonic acid dimethyl ester.

Analysis for $C_{24}H_{31}N_2O_5P$: Calculated C, 62.89; H, 6.82; N, 6.11. Found C, 62.72; H, 6.97; N, 6.29.

Example 62

Preparation of [3-[[3-(2-amino-2-oxoethyl)-2-ethyl-1-(phenylmethyl)-1H-indol-5-yl]oxy]propyl] phosphonic acid

[3-[[3-(2-amino-2-oxoethyl)-2-ethyl-1-(phenylmethyl)-1H-indol-5-yl]oxy]propyl]phosphonic acid dimethyl ester (150 mg, 0.33 mmol) and 0.35 mL (2.6 mmol) of trimethylsilyl bromide in 2 mL of methylene chloride was stirred for 16 hours, 5 mL of MeOH added, stirred 1.0 hour and concentrated at reduced pressure. The residue was crystallized from EtOAc/MeCN/HOAc/water to give 138 mg (97% yield) of [3-[[3-(2-amino-2-oxoethyl)-2-ethyl-1-(phenylmethyl)-1H-indol-5-yl]oxy]propyl]phosphonic acid, mp, 194°–196° C.

Analysis for $C_{22}H_{27}N_2O_5P$: Calculated C, 61.39; H, 6.32; N, 6.51. Found C, 61.35; H, 6.38; N, 6.35.

Example 63

Preparation of [3-[[3-(2-Amino-2-oxoethyl)-2-ethyl-1-(phenylmethyl)-1H-indol-5-yl]oxy]propyl] phosphonic acid monomethyl ester A mixture of 162 mg (0.35 mmol) of [3-[[3-(2-amino-2-oxoethyl)-2-ethyl-1-(phenylmethyl)-1H-indol-5-yl]oxy]propyl]phosphonic acid dimethyl ester and 5 mL of 1N NaOH in 10 mL of MeOH was heated to maintain reflux for 5 hours, diluted with water and extracted with ethyl acetate. The aqueous layer was made acidic to pH 2–3 with 1N HCl and extracted with ethyl acetate. The ethyl acetate solution was washed with brine, dried (MgSO$_4$) and concentrated at reduced pressure to give 120 mg (77% yield) of [3-[[3-(2-amino-2-oxoethyl)-2-ethyl-1-(phenylmethyl)-1H-indol-5-yl]oxy]propyl]phosphonic acid monomethyl ester.

Analysis for $C_{23}H_{29}N_2O_5P$: Calculated C, 62.15; H, 6.58; N, 6.30. Found C, 63.15; H, 6.45; N, 4.81.

Example 64

Preparation of [3-[[3-(2-Amino-2-oxoethyl)-1-[(3-chlorophenyl)methyl]-2-ethyl-1H-indol-5-yl]oxy] propyl]phosphonic acid A. 1-[(3-Chlorophenyl)methyl]-2-ethyl-5-methoxy-1H-indole-3-acetic acid ethyl ester. 2-Ethyl-5-methoxy-1H-indole-3-acetic acid ethyl ester (1.82 g, 7.4 mmol) was added to 296 mg (7.4 mmol) of NaH/mineral oil (previously washed with hexane), the mixture stirred for 0.5 hours and 0.93 mL (7.4 mmol) of 3-chlorobenzyl chloride added. After 21 hours, water was added and the mixture extracted with ethyl acetate. The ethyl acetate was washed with brine, dried (MgSO$_4$) and concentrated at reduced pressure. The residue was chromatographed on silica gel eluting with 20% EtOAc/hexane to give 2.13 g (75% yield) of 1-[(3-chlorophenyl) methyl]-2-ethyl-5-methoxy-1H-indole-3-acetic acid ethyl ester as an oil.

Analysis for $C_{22}H_{24}ClNO_3$: Calculated C, 68.48; H, 6.27; N, 6.63. Found C, 68.25; H, 6.52; N, 3.45.

B. 1-[(3-Chlorophenyl)methyl]-2-ethyl-5-methoxy-1H-indole-3-acetic acid hydrazide. A mixture of 1.93 g (5 mmol) of 1-[(3-chlorophenyl)methyl]-2-ethyl-5-methoxy-1H-indole-3-acetic acid ethyl ester and 5 mL of hydrazine in 20 mL of ethanol was heated to maintain reflux for 19 hours. After cooling, water was added and the mixture was extracted with ethyl acetate. The ethyl acetate solution was washed with brine, dried (MgSO$_4$), and concentrated to give 1.144 g (62% yield) of 1-[(3-chlorophenyl)methyl]-2-ethyl-5-methoxy-1H-indole-3-acetic acid hydrazide.

Analysis for $C_{20}H_{22}ClN_3O_2$: Calculated C, 64.60; H, 5.96; N, 11.30. Found C, 64.37; H, 6.13; N, 11.18.

C. 1-[(3-Chlorophenyl)methyl]-2-ethyl-5-methoxy-1H-indole-3-acetamide. A mixture of 340 mg (0.92 mmol) of 1-[(3-chlorophenyl)methyl]-2-ethyl-5-methoxy-1H-indole-3-acetic acid hydrazide and 200 mg of Raney Ni in 20 mL of ethanol was heated to maintain reflux for 2.5 hours. After cooling the solvent was decanted and the Raney Ni washed twice with methylene chloride. The combined organic solvents were filtered, concentrated at reduced pressure and the residue chromatographed on silica gel eluting with ethyl acetate to give 244 mg (74% yield) of 1-[(3-chlorophenyl)methyl]-2-ethyl-5-methoxy-1H-indole-3-acetamide.

D. 1-[(3-Chlorophenyl)methyl]-2-ethyl-5-hydroxy-1H-indole-3-acetamide. A solution of 226 mg (0.63 mmol) of 1-[(3-chlorophenyl)methyl]-2-ethyl-5-methoxy-1H-indole-3-acetamide and 2.5 mL of 1M BBr$_3$/methylene chloride in 15 mL of methylene chloride was stirred for 6 hours. The mixture was concentrated at reduced pressure, the residue dissolved in ethyl acetate, washed with water, brine and dried (MgSO$_4$). After concentrating at reduced pressure, the residue was chromatographed on silica gel and eluted with EtOAc to give 174 mg (81% yield) of 1-[(3-chlorophenyl) methyl]-2-ethyl-5-hydroxy-1H-indole-3-acetamide.

E. [3-[[3-(2-Amino-2-oxoethyl)-1-[(3-chlorophenyl)methyl]-2-ethyl-1H-indol-5-yl]oxy]propyl]phosphonic acid dimethyl ester. 1-[(3-Chlorophenyl)methyl]-2-ethyl-5-hydroxy-1H-indole-3-acetamide (170 mg, 0.5 mmol) was added to 20 mg (0.5 mmol) of NaH/mineral oil in 10 mL of DHF, stirred 1 hour, 121 mg (0.8 mmol) of (3-bromopropyl) phosphonic acid dimethyl ester added and stirring maintained for 4 hours. The mixture was diluted with water, extracted with ethyl acetate, the ethyl acetate washed with brine, dried (MgSO$_4$) and concentrated. The residue was chromatographed on silica gel eluting with EtOAc then 10% MeOH/EtOAc to give 99 mg (40% yield) of [3-[[3-(2-amino-2-oxoethyl)-1-[(3-chlorophenyl)methyl]-2-ethyl-1H-indol-5-yl]oxy]propyl]phosphonic acid dimethyl ester.

F. [3-[[3-(2-Amino-2-oxoethyl)-1-[(3-chlorophenyl) methyl]-2-ethyl-1H-indol-4-yl]oxy]propyl]phosphonic acid. [[3-[[3-(2-Amino-2-oxoethyl)-1-[(3-chlorophenyl)methyl]-2-ethyl-1H-indol-5-yl]oxy]propyl]phosphonic acid dimethyl ester (99 mg, 0.2 mmol) and 0.21 mL (1.6 mmol) of trimethylsilyl bromide in 2 mL of methylene chloride was stirred for 16 hours, 5 mL of MeOH added, stirred 0.75 hours and concentrated at reduced pressure. The residue was crystallized from EtOAc/MeCN/HOAc/water to give 60 mg (65% yield) of [3-[[3-(2-amino-2-oxoethyl)-1-[(3-chlorophenyl)methyl]-2-ethyl-1H-indol-5-yl]oxy]propyl] phosphonic acid, mp, 203°–205° C.

Analysis for $C_{22}H_{26}ClN_2O_5P$: Calculated C, 56.84; H, 5.64; N, 6.03. Found C, 56.80; H, 5.68; N, 5.96.

Example 65

Preparation of 4-(2-Hydrazino-2-oxoethoxy)-2-methyl-1-(phenylmethyl)-1H-indole-3-acetamide A mixture of 484 mg (1.3 mmol) of 2-[[3-(2-amino-2-oxoethyl)-2-methyl-1-(phenylmethyl)-1H-indol-4-yl]oxy] acetic acid methyl ester (Example 39) and 2 mL of hydrazine in 10 mL of ethanol was heated to maintain reflux for 16 hours, 10 mL of ethanol added, heated an additional 4 hours and cooled. Ethyl acetate and water were added and the insoluble material filtered. The ethyl acetate solution was separated, washed with brine, dried (MgSO$_4$) and concentrated. The residue was combined with the precipitate above to give 435 mg (91% yield) of 4-(2-hydrazino-2-oxoethoxy)-2-methyl-1-(phenylmethyl)-1H-indole-3-acetamide, mp, 207°–210° C.

Analysis for $C_{20}H_{22}N_4O_3$: Calculated C, 65.56; H, 6.05; N, 15.29. Found C, 65.57; H, 6.14; N, 15.40.

Example 66

Preparation of 4-(2-Amino-2-oxoethoxy)-2-methyl-1-(phenylmethyl)-1H-indole-3-acetamide A mixture of 230 mg (0.63 mmol) of 4-(2-hydrazino-2-oxoethoxy)-1-methyl-1-(phenylmethyl)-1H-indole-3-acetamide and 300 mg of Raney Ni in 40 mL of ethanol was heated to maintain reflux for 4 hours. The mixture was cooled, the EtOH poured off the catalyst, and the catalyst washed twice with methylene chloride. The combined solvents were filtered, concentrated and the residue chromatographed on silica gel and on eluting with 10% MeOH/EtOAc, 25 mg (11% yield) of 4-(2-amino-2-oxoethoxy)-2-methyl-1-(phenylmethyl)-1H-indole-3-acetamide were obtained. This material melted at 190°–207° C.

Analysis for $C_{20}H_{21}N_3O_3$: Calculated C, 68.36; H, 6.02; N, 11.96. Found C, 68.08; H, 6.55; N, 13.28.

Example 67

Preparation of [[3-(2-Amino-2-oxoethyl)-2-methyl-1-(phenylmethyl)-1H-indol-4-yl]oxy]methyl] phosphonic acid diethyl ester 4-Hydroxy-2-methyl-1-(phenylmethyl)-1H-indole-3-acetamide (294 mg, 1 mmol) was added to 40 mg (1 mmol) of 60% NaH/mineral oil (previously washed with hexane) in 2 mL of DMF, stirred 0.33 hours, 1.1 g (4 mmol) of iodomethylphosphonic acid diethyl ester added, stirred 72 hours, 1.1 g (4 mmol) of iodomethylphosphonic acid diethyl ester added and stirring continued 24 hours. The mixture was diluted with water, extracted with ethyl acetate, the ethyl acetate washed with brine, dried ($MgSO_4$) and concentrated at reduced pressure. The residue was chromatographed on silica gel eluting with ethyl acetate, then 10% MeOH/EtOAc to give 206 mg (46% yield) of [[3-(2-amino-2-oxoethyl)-2-methyl-1-(phenylmethyl)-1H-indol-4-yl]oxy]methyl]phosphonic acid diethyl ester.

Example 68

Preparation of [[3-(2-Amino-2-oxoethyl)-2-methyl-1-(phenylmethyl)-1H-indol-4-yl]oxy]methyl] phosphonic acid

[[3-(2-Amino-2-oxoethyl)-2-methyl-1-(phenylmethyl)-1H-indol-4-yl]oxy]methyl]phosphonic acid diethyl ester (206 mg, 0.46 mmol) and 0.49 mL (3.7 mmol) of trimethylsilyl bromide in 2 mL of methylene chloride was stirred for 16 hours, 5 mL of MeOH added, stirred 1.0 hour and concentrated at reduced pressure. The residue was crystallized from EtOAc/MeCN/HOAc/water to give 52 mg (29% yield) of [[3-(2-amino-2-oxoethyl)-2-methyl-1-(phenylmethyl)-1H-indol-4-yl]oxy]methyl]phosphonic acid, mp, 195°–198° C.

Analysis for $C_{19}H_{21}ClN_2O_5P$: Calculated C, 58.76; H, 5.45; N, 7.21. Found C, 58.52; H, 5.32; N, 7.26.

Example 69

Preparation of 1-[(3-Chlorophenyl)methyl]-5-methoxy-2-methyl-1H-indole-3-acetamide A. 1-[(3-Chlorophenyl)methyl]-5-methoxy-2-methyl-1H-indole-3-acetic acid ethyl ester. Using the procedure described in Example 65, Part A, 741 mg (3 mmol) of 5-methoxy-2-methyl-1H-indole-3-acetic acid ethyl ester (Example 35, Part C) was reacted with 120 mg (3 mmol) of 60% NaH/mineral oil and then 0.38 mL (3 mmol) of 3-chlorobenzyl chloride to give a product that chromatographed on silica gel (eluted with 20% EtOAc/hexane) to give 790 mg (70% yield) of 1-[(3-chlorophenyl)methyl]-5-methoxy-2-methyl-1H-indole-3-acetic acid ethyl ester, mp, 113°–115° C.

Analysis for $C_{21}H_{22}ClNO_3$: Calculated C, 67.83; H, 5.96; N, 3.77. Found C, 70.39; H, 6.31; N, 3.82.

B. 1-[(3-Chlorophenyl)methyl]-5-methoxy-2-methyl-1H-indole-3-acetic acid hydrazide. A mixture of 780 mg (2 mmol) of 1-[(3-chlorophenyl)methyl]-5-methoxy-2-methyl-1H-indole-3-acetic acid ethyl ester and 2 mL of hydrazine in 10 mL of ethanol was heated to maintain reflux for 16 hours, poured into ethyl acetate/water and the ethyl acetate separated, washed with brine and dried ($MgSO_4$). After concentrating, the residue was stirred with MeOH and the insoluble material filtered to give 698 mg (98% yield) of 1-[(3-chlorophenyl)methyl]-5-methoxy-2-methyl-1H-indole-3-acetic acid hydrazide, mp, 160°–162° C.

Analysis for $C_{19}H_{20}ClN_3O_2$: Calculated C, 63.77; H, 5.63; N, 11.74. Found C, 63.97; H, 5.70; N, 11.56.

C. 1-[(3-Chlorophenyl)methyl]-5-methoxy-2-methyl-1H-indole-3-acetamide. A mixture of 675 mg (1.9 mmol) of 1-[(3-chlorophenyl)methyl]-5-methoxy-2-methyl-1H-indole-3-acetic acid hydrazide and 500 mg of Raney Ni in 25 mL of ethanol was heated to maintain reflux for 3.5 hours and cooled to room temperature. The ethanol was decanted and the Raney Ni washed twice with methylene chloride. The combined solvents were filtered, concentrated at reduced pressure and the residue chromatographed on silica gel (eluted with EtOAc) to give 503 mg (77% yield) of 1-[(3-chlorophenyl)methyl]-5-methoxy-2-methyl-1H-indole-3-acetamide, mp, 171°–173° C.

Analysis for $C_{19}H_{19}ClN_2O_2$: Calculated C, 66.57; H, 5.59; N, 8.17. Found C, 66.79; H, 5.73; N, 8.17.

Example 70

Preparation of 1-[(3-Chlorophenyl)methyl]-5-hydroxy-2-methyl-1H-indole-3-acetamide A solution of 483 mg (1.4 mmol) of 1-[(3-chlorophenyl)methyl]-5-methoxy-2-methyl-1H-indole-3-acetamide and 5.6 mL of 1M $BBr_3$/methylene chloride in 20 mL of methylene chloride was stirred for 5 hours, 2 mL of 1M $BBr_3$/methylene chloride added and stirred 16 hours. The mixture was poured into water, extracted with ethyl acetate, the ethyl acetate solution washed with brine, dried ($MgSO_4$) and concentrated at reduced pressure. The residue was chromatographed on silica gel and eluted using a gradient, 50% EtOAc/hexane→EtOAc, to give 155 mg of starting material, 1-[(3-chlorophenyl)methyl]-5-methoxy-2-methyl-1H-indole-3-acetamide, and 220 mg (48% yield) off 1-[(3-chlorophenyl)methyl]-5-hydroxy-2-methyl-1H-indole-3-acetamide, mp, 173°–177° C.

Analysis for $C_{18}H_{17}ClN_2O_2$: Calculated C, 65.75; H, 5.21; N, 8.52. Found C, 65.93; H, 5.32; N, 8.46.

Example 71

Preparation of [[3-(2-Amino-2-oxoethyl)-1-[(3-chlorophenyl)methyl]-2-methyl-1H-indol-4-yl]oxy] acetic acid ethyl ester 1-[(3-Chlorophenyl)methyl]-4-hydroxy-2-methyl-1H-indole-3-acetamide (206 mg, 0.63 mmol) was added to 25 mg (0.63 mmol) of 60% NaH/mineral oil (previously washed with hexane) in 6 mL of DMF, stirred 0.5 hours, 0.06 mL (0.63 mmol) of methyl 2-bromoacetate added and stirred 2.5 hours. The mixture was diluted with water, extracted with ethyl acetate, the ethyl acetate washed with brine, dried (MgS₄) and concentrated at reduced pressure. The residue was stirred with MeOH and the insoluble material filtered to give 184 mg (73% yield) of [[3-(2-amino-2-oxoethyl)-1-[(3-chlorophenyl)methyl]-2-methyl-1H-indol-4-yl]oxy] acetic acid ethyl ester, mp, 180°–183° C.

Analysis for $C_{21}H_{21}ClN_2O_4$: Calculated C, 62.92; H, 5.28; N, 6.99. Found C, 63.06; H, 5.29; N, 6.93.

Example 72

Preparation of [[3-(2-Amino-2-oxoethyl)-1-[(3-chlorophenyl)methyl]-2-methyl-1H-indol-4-yl]oxy]methyl]acetic acid sodium salt A mixture of 155 mg (0.39 mmol) of [[3-(2-amino-2-oxoethyl)-1-[(3-chlorophenyl)methyl]-2-methyl-1H-indol-4-yl]oxy]acetic acid ethyl ester and 4 mL of 1N NaOH in 10 mL of ethanol was heated 0.5 hours, allowed to cool and the precipitate filtered to give 140 mg (88% yield) of [[3-(2-amino-2-oxoethyl)-1-[(3-chlorophenyl)methyl]-2-methyl-1H-indol-4-yl]oxy]acetic acid sodium salt, mp, >250° C.

Analysis for $C_{20}H_{18}ClN_2O_4Na$: Calculated C, 58.76; H, 4.44; N, 6.85. Found C, 59.01; H, 4.55; N, 6.75.

Example 73

Preparation of [[3-(2-Amino-2-oxoethyl)-1-([1,1'-biphenyl]-2-ylmethyl)-2-methyl-1H-indol-4-yl]oxy] acetic acid sodium salt A. 1-([1,1'-Biphenyl]-2-ylmethyl)-4-methoxy-2-methyl-1H-indole-3-acetic acid ethyl ester. 5-Methoxy-2-methyl-1H-indole-3-acetic acid ethyl ester (1 g, 4 mmol) was added to 160 mg (4 mmol) of NaH/mineral oil (previously washed with hexane), the mixture stirred for 1.0 hours and 0.13 mL (4 mmol) of 2-(bromomethyl)biphenyl added. After 3 hours, water was added and the mixture extracted with ethyl acetate. The ethyl acetate was washed with brine, dried (MgSO₄) and concentrated at reduced pressure. The residue was chromatographed on silica gel eluting with 20% EtOAc/hexane to give 1.18 g (71% yield) of 1-([1,1'-biphenyl]-2-ylmethyl)-4-methoxy-2-methyl-1H-indole-3-acetic acid ethyl ester as an oil.

B. 1-([1,1'-Biphenyl]-2-ylmethyl)-4-methoxy-2-methyl-1H-indole-3-acetic acid hydrazide. A mixture of 1.18 g (2.9 mmol) of 1-([1,1'-biphenyl]-2-ylmethyl)-4-methoxy-2-methyl-1H-indole-3-acetic acid ethyl ester and 3 mL of hydrazine in 20 mL of ethanol was heated to maintain reflux for 15 hours. After cooling, water was added and the mixture was extracted with ethyl acetate. The ethyl acetate solution was washed with brine, dried (MgSO₄), and concentrated. The residue was chromatographed on silica gel (eluted with EtOAc and then 10% MeOH/EtOAc) to give 646 mg (56% yield) of 1-([1,1'-biphenyl]-2-ylmethyl)-4-methoxy-2-methyl-1H-indole-3-acetic acid hydrazide mp, 148°–150° C.

Analysis for $C_{25}H_{25}N_3O_2$: Calculated C, 75.16; H, 6.31; N, 10.52. Found C, 75.14; H, 6.40; N, 10.63.

C. 1-([1,1'-Biphenyl]-2-ylmethyl)-4-methoxy-2-methyl-1H-indole-3-acetamide. A mixture of 576 mg (1.44 mmol) of this material and 300 mg of Raney Ni in 20 mL of ethanol was heated to maintain reflux for 3 hours. After cooling the solvent was decanted and the Raney Ni washed twice with methylene chloride. The combined organic solvents were filtered and concentrated at reduced pressure and the residue was redissolved in EtOAc and washed with water. After drying (MgSO₄), the ethyl acetate was removed at reduced pressure and the residue was 437 mg (71% yield) of 1-([1,1'-biphenyl]-2-ylmethyl)-4-methoxy-2-methyl-1H-indole-3-acetamide, mp, 173°–175° C.

Analysis for $C_{25}H_{24}N_2O_2$: Calculated C, 78.10; H, 6.29; N, 7.29. Found C, 78.94; H, 6.27; N, 7.35.

D. 1-([1,1'-Biphenyl]-2-ylmethyl)-4-hydroxy-2-methyl-1H-indole-3-acetamide. A solution of 430 mg (1.1 mmol) of 1-([1,1'-biphenyl]-2-ylmethyl)-4-methoxy-2-methyl-1H-indole-3-acetamide and 4.4 mL of 1M BBr₃/methylene chloride in 10 mL of methylene chloride was stirred for 5.5 hours. The mixture was concentrated at reduced pressure, the residue dissolved in ethyl acetate, washed with water, brine and dried (MgSO₄). After concentrating at reduced pressure, the residue was chromatographed on silica gel and eluted with EtOAc to give 400 mg (98% yield) of 1-([1,1'-biphenyl]-2-ylmethyl)-4-hydroxy-2-methyl-1H-indole-3-acetamide.

E. [[3-(2-Amino-2-oxoethyl)-1-([1,1'-biphenyl]-2-ylmethyl)-2-methyl-1H-indol-4-yl]oxy]acetic acid methyl ester. 1-([1,1'-Biphenyl]-2-ylmethyl)-4-hydroxy-2-methyl-1H-indole-3-acetamide (400 mg, 1.08 mmol) was added to 43 mg (1.08 mmol) of NaH/mineral oil in 5 mL of DMF, stirred 1 hour, 0.1 mL (1.08 mmol) of methyl 2-bromoacetate added and stirring maintained for 19 hours. The mixture was diluted with water, extracted with ethyl acetate, the ethyl acetate washed with brine, dried (MgSO₄) and concentrated. The residue was chromatographed on silica gel eluting with 50% EtOAc/hexane to give 319 mg (67% yield) of [[3-(2-amino-2-oxoethyl)-1-([1,1'-biphenyl]-2-ylmethyl)-2-methyl-1H-indol-4-yl]oxy]acetic acid methyl ester.

F. [[3-(2-Amino-2-oxoethyl)-1-([1,1'-biphenyl]-2-ylmethyl)-2-methyl-1H-indol-4-yl]oxy]acetic acid sodium salt. [[3-(2-Amino-2-oxoethyl)-1-([1,1'-biphenyl]-2-ylmethyl)-2-methyl-1H-indol-4-yl]oxy]acetic acid methyl ester (319 mg, 0.72 mmol) and 5 mL of 1N NaOH in 15 mL of MeOH was heated to maintain reflux for 0.5 hours, added to ethyl acetate/water and the insoluble material filtered to give 244 mg (75% yield) of [[3-(2-amino-2-oxoethyl)-1-([1,1'-biphenyl]-2-ylmethyl)-2-methyl-1H-indol-4-yl]oxy] acetic acid sodium salt, mp, >250° C.

Analysis for $C_{26}H_{23}N_2O_4Na$: Calculated C, 69.35; H, 5.15; N, 6.22. Found C, 69.10; H, 5.36; N, 5.94.

Example 74

Preparation of [[3-(2-Amino-2-oxoethyl)-2-ethyl-1-(phenylmethyl)-1H-indol-4-yl]oxy]acetic acid A. N-tert-butoxycarbonyl-3-methoxy-2-methylaniline. A solution of 44.4 g (344 mmol) of 3-methoxy-2-methylaniline and 75 g (344 mmol) of di-tert-butyl dicarbonate in 400 mL of THF was heated to maintain reflux for 4 hours. After concentrating at reduced pressure, the residue was taken up in ethyl acetate, washed with 1N citric acid, water and dried (MgSO₄). After removing the solvent at reduced pressure, the residue was crystallized from hexane to give 64.5 g (84% yield) of N-tert-butoxycarbonyl-3-methoxy-2-methylaniline, mp, 56°–57° C.

Analysis for $C_{13}H_{19}NO_3$: Calculated C, 65.80; H, 8.07; N, 5.90. Found C, 63.32; H, 7.83; N, 5.56.

B. 2-Ethyl-4-methoxy-1H-indole. A solution of 140 mL (0.18 mol) of 1.3M sec-butyl lithium in cyclohexane was added slowly to N-tert-butoxycarbonyl-3-methoxy-2- methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over MgSO$_4$, and concentrated at reduced pressure to give 25.5 g of a crude of 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried (MgSO$_4$) and concentrated. The residue was chromatographed three times on silica eluting with 20% EtOAc/hexane to give 13.9 g of 2-ethyl-4-methoxy-1H-indole.

Analyses for C$_{11}$H$_{13}$NO: Calculated C, 75.40; H, 7.48; N, 7.99. Found C, 74.41; H, 7.64; N, 7.97.

C. 2-Ethyl-4-methoxy-1-(phenylmethyl)-1H-indole. 2-Ethyl-4-methoxy-1H-indole (4.2 g, 24 mmol) was dissolved in 30 mL of DMF and 960 mg (24 mmol) of 60% NaH/mineral oil was added. After 1.5 hours, 2.9 mL (24 mmol) of benzyl bromide was added. After 4 hours, the mixture was diluted with water and extracted twice with ethyl acetate. The combined ethyl acetate was washed with brine, dried (MgSO$_4$) and concentrated at reduced pressure. The residue was chromatographed on silica gel and eluted with 20% EtOAc/hexane to give 3.1 g (49% yield) of 2-ethyl-4-methoxy-1-(phenylmethyl)-1H-indole.

D. 2-Ethyl-4-methoxy-alpha-oxo-1-(phenylmethyl)-1H-indole-3-acetamide. Oxalyl chloride (0.87 mL, 10 mmol) was added to 2.6 g (9.8 mmol) of 2-ethyl-4-methoxy-1-(phenylmethyl)-1H-indole in 25 mL of methylene chloride, the mixture stirred for 3 hours and concentrated at reduced pressure. The residue was redissolved in 25 mL of methylene chloride, anhydrous ammonia bubbled in for 0.25 hours and the mixture concentrated. The residue was stirred with ethyl acetate/water and the insoluble material filtered. The ethyl acetate from the filtrate was washed with brine, dried (MgSO$_4$) and concentrated. The residue was washed with ether and combined with the filtered material above to give 1.19 g (36% yield) of 2-ethyl-4-methoxy-alpha-oxo-1-phenylmethyl)-1H-indole-3-acetamide, mp, 193°–199° C.

Analysis for C$_{20}$H$_{20}$N$_2$O$_3$: Calculated C, 71.41; H, 5.99; N, 8.33. Found C, 66.22; H, 6.16; N, 10.42.

E. 2-Ethyl-4-methoxy-alpha-hydroxy-1-(phenylmethyl)-1H-indole-3-acetamide. A mixture of 1 g (3 mmol) of 2-ethyl-4-methoxy-alpha-oxo-1-(phenylmethyl)-1H-indole-3-acetamide and 142 mg (3.75 mmol) of sodium borohydride and 100 mL of ethanol was stirred for 20 hours, and evaporated at reduced pressure. The residue was taken up in ethyl acetate and water, the ethyl acetate separated and washed with brine and dried (MgSO$_4$). The solution was concentrated at reduced pressure and the residue stirred with ether. The insoluble material was filtered to give 893 mg (88%) of 2-ethyl -4-methoxy-alpha-hydroxy-1-(phenylmethyl)-1H-indole-3-acetamide, mp, 160°–162° C.

Analysis for C$_{20}$H$_{22}$N$_2$O$_3$: Calculated C, 70.99; H, 6.55; N, 8.28. Found C, 70.76; H, 6.55; N, 8.11.

F. 2-Ethyl-4-methoxy-1-(phenylmethyl)-1H-indole-3-acetamide. A solution of 875 mg (2.6 mmol) of 2-ethyl-4-methoxy-alpha-hydroxy-1-(phenylmethyl)-1H-indole-3-acetamide and 0.51 mL (3.23 mmol) of triethylsilane in 10 mL of trifluoroacetic acid was stirred for 16 hours and concentrated at reduced pressure. The residue was taken up in ethyl acetate and water, the ethyl acetate separated, washed with brine and dried (MgSO$_4$). The residue was chromatographed on silica gel and eluted first with 50% ethyl acetate/hexane and then ethyl acetate to give 521 mg (62% yield) of 2-ethyl-4-methoxy-1-(phenylmethyl)-1H-indole-3-acetamide, mp, 152°–154° C.

Analysis for C$_{20}$H$_{22}$N$_2$O$_2$: Calculated C 74.51; H, 6.88; N, 8.69. Found C, 74.24; H, 6.90; N, 8.72.

G. 2-Ethyl-4-hydroxy-1-(phenylmethyl)-1H-indole-3-acetamide. 2-Ethyl-4-methoxy-1-(phenylmethyl)-1H-indole-3-acetamide (483 mg, 1.5 mmol) and 6 mL of BBr$_3$ were reacted as described in Example 56, Part C, to give after chromatography on silica gel (eluted with ethyl acetate) 156 mg (34% yield) of 2-ethyl-4-hydroxy-1-(phenylmethyl)-1H-indole-3-acetamide.

Analysis for C$_{19}$H$_{20}$N$_2$O$_2$: Calculated C, 74.00; H, 6.54; N, 9.08. Found C, 69.23; H, 6.09; N, 8.24.

H. 2-[[3-(2-Amino-2-oxoethyl)-2-ethyl-1-(phenylmethyl)-1H-indol-4-yl]oxy]acetic acid methyl ester. 2-Ethyl-4-hydroxy-1-(phenylmethyl)-1H-indole-3-acetamide (135 mg, 0.44 mmol) was added to 17.6 mg (0.44 mmol) of NaH/mineral oil (washed with hexanes) in 5 mL of DHF, stirred 0.5 hour, 0.04 mL (0.44 mmol) of methyl 2-bromoacetate added and stirring maintained for 5 hours. The mixture was diluted with water, extracted with ethyl acetate. Some material was insoluble and was filtered. The ethyl acetate was washed with brine, dried (MgSO$_4$) and concentrated. The residue was combined with the filtered material to give 119 mg (71% yield) of 2-[[3-(2-amino-2-oxoethyl)-2-ethyl-1-(phenylmethyl)-1H-indol-4-yl]oxy] acetic acid methyl ester.

Analysis for C$_{22}$H$_{24}$N$_2$O$_4$: Calculated C, 69.46; H, 6.36; N, 7.36. Found C, 69.65; H, 6.41; N, 7.35.

I. 2-[[3-(2-Amino-2-oxoethyl)-2-ethyl-1-(phenylmethyl)-1H-indol-4-yl]oxy]acetic acid. A mixture of 100 mg (0.26 mmol) of 2-[[3-(2-amino-2-oxoethyl)-2-ethyl-1-(phenylmethyl)-1H-indol-4-yl]oxy]acetic acid methyl ester and 2 mL of 1N NaOH in 6 mL of MeOH was heated to dissolve all materials and then stirred at room temperature for 1 hour. Water and ethyl acetate were added and the aqueous layer separated, made acidic to pH 3 with 1N HCl and ethyl acetate added. The insoluble material was filtered. The ethyl acetate solution was washed with brine, dried (MgSO$_4$), and concentrated at reduced pressure. The residue was combined with the filtered material above to give 90 mg (95% yield) of 2-[[3-! 2-amino-2-oxoethyl)-2-ethyl-1-(phenylmethyl)-1H-indol-4-yl]oxy]acetic acid, mp, 220°–222° C.

Analysis: Calc'd for C$_{21}$H$_{22}$N$_2$O$_4$: C, 68.84; H, 6.05; N, 7.65. Found: C, 67.52; H, 5.67; N, 8.46.

Example 75

Preparation of 2-[[3-(2-Amino-2-oxoethyl)-1-[(3-chlorophenyl)methyl]-2-ethyl-1H-indol-4-yl]oxy] acetic acid A. 1-[(3-Chlorophenyl)methyl]-2-ethyl-4-methoxy-1H-indole. 2-Ethyl-4-methoxy-1H-indole (7.65 g, 44 mmol) was dissolved in 50 mL of DMF and 1.76 g (44 mmol) of 60% NaH/mineral oil was added. After 0.75 hours, 5.6 mL (24 mmol) of 3-chlorobenzyl chloride was added. After 18 hours, the mixture was diluted with water and extracted twice with ethyl acetate. The combined ethyl acetate was washed with brine, dried (MgSO₄) and concentrated at reduced pressure. The residue was chromatographed on silica gel and eluted with 20% EtOAc/hexane to give 1.61 g (12% yield) of 1-[(3-chlorophenyl)methyl]-2-ethyl-4-methoxy-1H-indole.

B. 1-[(3-Chlorophenyl)methyl]-2-ethyl-4-methoxy-alpha-oxo-1H-indole-3-acetamide. Oxalyl chloride (0.5 mL, 5.3 mmol) was reacted with 1.6 g (5.3 mmol) of 1-[(3-chlorophenyl)methyl]-2-ethyl-4-methoxy-1H-indole in 20 mL of methylene chloride and ammonia as described in Example 75, Part C and was worked up with the addition of chromatography on silica gel (eluting with ethyl acetate) to give 1.47 g (75% yield) of 1-[(3-chlorophenyl)methyl]-2-ethyl-4-methoxy-alpha-oxo-1H-indole-3-acetamide, mp, 124°–129° C.

Analysis for $C_{20}H_{19}ClN_2O_3$: Calculated C, 64.78; H, 5.16; N, 7.55. Found C, 64.72; H, 5.16; N, 7.66.

C. 1-[(3-Chlorophenyl)methyl]-2-ethyl-4-methoxy-alpha-hydroxy-1H-indole-3-acetamide. Using the procedure described in Example 75, Part E, 750 mg (2 mmol) of 1-[(3-chlorophenyl)methyl]-2-ethyl-4-methoxy-alpha-oxo-1H-indole-3-acetamide and 95 mg (3.5 mmol) of sodium borohydride in 50 mL of ethanol were reacted to give after washing with methylene chloride 290 mg (39%) of 1-[(3-chlorophenyl)methyl]-2-ethyl-4-methoxy-alpha-hydroxy-1H-indole-3-acetamide, mp, 134°–136° C.

Analysis for $C_{20}H_{21}ClN_2O_3$: Calculated C, 64.43; H, 5.68; N, 7.51. Found C, 65.61; H, 5.81; N, 11.24.

D. 1-[(3-Chlorophenyl)methyl]-2-ethyl-4-methoxy-1H-indole-3-acetamide. By the method in Example 75, Part F, 280 mg (0.75 mmol) of 1-[(3-chlorophenyl)methyl]-2-ethyl-4-methoxy-alpha-hydroxy-1H-indole-3-acetamide was reduced with 0.12 mL (0.75 mmol) of triethylsilane in 2 mL of trifluoroacetic acid to give by chromatography on silica gel (eluted ethyl acetate) 125 mg (48% yield) of 1-[(3-chlorophenyl)methyl]-2-ethyl-4-methoxy-1H-indole-3-acetamide.

E. 1-[(3-Chlorophenyl)methyl]-2-ethyl-4-hydroxy-1H-indole-3-acetamide. 1-[(3-Chlorophenyl)methyl]-2-ethyl-4-methoxy-1H-indole-3-acetamide. (123 mg, 0.35 mmol) and 1.4 mL of BBr₃ were reacted as described in Example 56, Part C, to give after chromatography on silica gel (eluted with ethyl acetate) 156 mg (34% yield) of 1-[(3-chlorophenyl)methyl]-2-ethyl-4-hydroxy-1H-indole-3-acetamide.

F. [[3-(2-Amino-2-oxoethyl)-1-[(3-chlorophenyl)methyl]-2-ethyl-1H-indol-4-yl]oxy]acetic acid methyl ester. (1-[(3-Chlorophenyl)methyl]-2-ethyl-4-hydroxy-1H-indole-3-acetamide (91 mg, 0.3 mmol) was reacted with 12 mg (0.3 mmol) of NaH/mineral oil (washed with hexanes) in 10 mL of DMF and then 0.03 mL (0.3 mmol) of methyl 2-bromoacetate as described in Example 75, Part H, to give after chromatography on silica gel (eluted with ethyl acetate) 80 mg (71% yield) of 2-[[3-(2-amino-2-oxoethyl)-2-ethyl-1-(phenylmethyl)-1H-indol-4-yl]oxy]acetic acid methyl ester.

G. [[3-(2-Amino-2-oxoethyl)-1-[(3-chlorophenyl)methyl]-2-ethyl-1H-indol-4-yl]oxy]acetic acid. A mixture of 80 mg (0.19 mmol) of [[3-(2-amino-2-oxoethyl)-2-ethyl-1-(phenylmethyl)-1H-indol-4-yl]oxy]acetic acid methyl ester and 1 mL of 1N NaOH in 3 mL of MeOH was stirred at room temperature for 1.5 hours. water and ethyl acetate were added and the aqueous layer separated, made acidic no pH 3 with 1N HCl. The insoluble material was filtered and the ethyl acetate solution was washed with brine, dried (MgSO₄), and concentrated at reduced pressure. The residue was stirred with ethyl acetate and filtered and this material combined with the filtered material above to give 61 mg (80% yield) of [[3-(2-amino-2-oxoethyl)-1-[(3-chlorophenyl)methyl]-2-ethyl-1H-indol-4-yl]oxy]acetic acid, mp, 216°–217° C.

Analysis for $C_{21}H_{21}ClN_2O_4$: Calculated C 62.92; H, 5.28; N, 6.99. Found C 63.09; H, 5.41; N, 6.99.

Example 76

Preparation of 2-[[3-(2-Amino-2-oxoethyl)-1-(phenylmethyl)-1H-indol-4-yl]oxy]acetic acid A. 4-Methoxy-1-(phenylmethyl)-1H-indole. 4-Methoxy-1H-indole (1.5 g, 10 mmol) was dissolved in 20 mL of DMF and 400 mg (10 mmol) of 60% NaH/mineral oil was added. After 1 hour, 1.2 mL (10 mmol) of benzyl bromide was added. After 3.5 hours, the mixture was diluted with water and extracted twice with ethyl acetate. The combined ethyl acetate was washed with brine, dried (MgSO₄) and concentrated at reduced pressure. The residue was chromatographed on silica gel and eluted with 20% EtOAc/hexane to give 1.77 g (75% yield) of 4-methoxy-1-(phenylmethyl)-1H-indole.

Analysis for $C_{16}H_{15}NO$: Calculated C, 81.98; H, 6.37; N, 5.90. Found C, 80.71; H, 6.24; N, 6.09.

B. 4-Methoxy-alpha-oxo-1-(phenylmethyl)-1H-indole-3-acetamide. Oxalyl chloride (0.63 mL, 7.2 mmol) was added to 1.7 g (7.2 mmol) of 4-methoxy-1-(phenylmethyl)-1H-indole in 20 mL of methylene chloride, the mixture stirred for 1 hour and concentrated at reduced pressure. The residue was redissolved in 25 mL of methylene chloride, anhydrous ammonia bubbled in for 0.25 hours and the mixture concentrated. The residue was stirred with ethyl acetate and the insoluble material filtered to give a mixture of 1.42 g of 2-ethyl-4-methox-alpha-oxo-1-phenylmethyl)-1H-indole-3-acetamide and ammonium chloride.

C. 4-Methoxy-alpha-hydroxy-1-(phenylmethyl)-1H-indole-3-acetamide. A mixture of 1.4 g (4.5 mmol) of 4-methoxy-alpha-oxo-1-(phenylmethyl)-1H-indole-3-acetamide and 213 mg (5.6 mmol) of sodium borohydride and 50 mL of ethanol was stirred for 20 hours, 213 mg (5.6 mmol) of sodium borohydride added and stirred an additional 20 hours and the mixture filtered and evaporated at reduced pressure. The residue was stirred with ethyl acetate and water and the insoluble material was filtered to give 600 mg (43%) of 4-methoxy-alpha-hydroxy-1-(phenylmethyl)-1H-indole-3-acetamide, mp, 179°–182° C.

Analysis for $C_{18}H_{18}N_2O_3$: Calculated C, 69.66; H, 5.85; N, 9.03. Found C, 69.52; H, 5.76; N, 8.86.

D. 4-Methoxy-1-(phenylmethyl)-1H-indole-3-acetamide. A solution of 600 mg (1.9 mmol) of 4-methoxy-alpha-hydroxy-1-(phenylmethyl)-1H-indole-3-acetamide and 0.32 mL (2 mmol) of triethylsilane in 5 mL of trifluoroacetic acid was stirred for 16 hours and concentrated at reduced pressure. The residue was taken up in ethyl acetate and water, the ethyl acetate separated, washed with brine and dried (MgSO₄). The residue was chromatographed on silica gel and eluted first with 50% ethyl acetate/hexane and then ethyl acetate to give after crystallizing from MeOH 262 mg (47% yield) of 4-methoxy-1-(phenylmethyl)-1H-indole-3-acetamide, mp, 184°–187° C.

Analysis for $C_{18}H_{18}N_2O_2$: Calculated C, 73.45; H, 6.16; N, 9.52. Found C, 77.20; H, 6.80; N, 9.13.

E. 4-Hydroxy-1-(phenylmethyl)-1H-indole-3-acetamide. 4-Methoxy-1-(phenylmethyl)-1H-indole-3-acetamide (236 mg, 0.8 mmol) and 3.2 mL of BBr$_3$ were reacted as described in Example 56, Part C, to give after chromatography on silica gel (eluted with 50% ethyl acetate/hexane) 78 mg (35% yield) of 4-hydroxy-1-(phenylmethyl)-1H-indole-3-acetamide.

F. 2-[[3-(2-Amino-2-oxoethyl)-2-ethyl-1-(phenylmethyl)-1H-indol-4-yl]oxy]acetic acid methyl ester. 2-Ethyl-4-hydroxy-1-(phenylmethyl)-1H-indole-3-acetamide (135 mg, 0.44 mmol) was added to 17.6 mg (0.44 mmol) of NaH/mineral oil (washed with hexanes) in 5 mL of DMF, stirred 1.5 hours, 0.04 mL (0.44 mmol) of methyl 2-bromoacetate added and stirring maintained for 3 hours. The mixture was diluted with water, extracted with ethyl acetate. The ethyl acetate was washed with brine, dried (MgSO$_4$) and concentrated. The residue was chromatographed on silica gel eluting with 2% MeOH/ethyl acetate to give 34 mg (34% yield) of 2-[[3-(2-amino-2-oxoethyl)-1-(phenylmethyl)-1H-indol-4-yl]oxy]acetic acid methyl ester.

G. 2-[[3-(2-Amino-2-oxoethyl)-1-(phenylmethyl)-1H-indol-4-yl]oxy]acetic acid. A mixture of 100 mg (0.26 mmol) of 2-[[3-(2-amino-2-oxoethyl)-1-(phenylmethyl)-1H-indol-4-yl]oxy]acetic acid methyl ester and 2 mL of 1N NaOH in 6 mL of MeOH was stirred at room temperature for 2 hours. Water and ethyl acetate were added and the aqueous layer separated, made acidic to pH 3 with 1N HCl and ethyl acetate added. The ethyl acetate solution was washed with brine, dried (MgSO$_4$), and concentrated at reduced pressure. The residue was stirred with methylene chloride and filtered to give 17 mg (56% yield) of 2-[[3-(2-amino-2-oxoethyl)-1-(phenylmethyl)-1H-indol-4-yl]oxy]acetic acid, mp, 207°–208° C.

Analysis for C$_{19}$H$_{18}$N$_2$O$_4$: Calculated C, 67.45; H, 5.36; N, 8.28. Found C, 67.64; H, 5.42; N, 8.05.

Example 77

2-Cyclopropyl-5-methoxy-1-(phenylmethyl)-1H-indole-3-acetamide

A. 1-[2-(tert-Butoxycarbonylamino)-5-methoxyphenyl]-2-butanone. A solution of 1.3M sec-butyl lithium/cyclohexane (100 mL, 0.13 mol) was added slowly to 15.17 g (0.065 mol) of N-tert-butoxycarbonyl-4-methoxy-2-methylaniline in 230 mL of THF while keeping the temperature below −40° C. with a dry ice-ethanol bath. The bath was removed and the temperature allowed to rise to −20° C. and then the bath was replaced. After the temperature had cooled to −55° C., 8.4 g (0.065 mol) of N-methoxy-N-methylcyclopropylcarboxamide in 20 mL of THF was added dropwise. The reaction mixture was stirred 1 hour, the cooling bath removed and stirred an additional 2 hours. It was then poured into 500 mL of water. The organic layer was separated, washed with water, dried over Na$_2$SO$_4$ and concentrated at reduced pressure. The residue was crystallized from hexane to give 15.22 g (77% yield) of [2-(tert-butoxycarbonylamino)-5-methoxyphenyl]cyclopropyl ketone, melting at 96°–97° C., Analyses for C$_{17}$H$_{23}$NO$_4$: Calculated C, 66.86; H, 7.59; N, 4.59. Found C, 66.67; H, 7.39; N, 4.45.

B. 2-Cyclopropyl-5-methoxy-1H-indole. [2-(tert-Butoxycarbonylamino)-5-methoxyphenyl]cyclopropyl ketone (13 g, 43 mmol) in 250 mL of CH$_2$Cl$_2$ and 25 mL of trifluoroacetic acid was stirred for 4 hours, washed with water, NaHCO$_3$ solution, dried (Na$_2$SO$_4$) and concentrated at reduced pressure. The residue was chromatographed on silica (eluted with a gradient, toluene→20% EtOAc/hexane) to give 4.15 g (49% yield) of 2-cyclopropyl-5-methoxy-1H-indole as an oil.

Analyses for C$_{12}$H$_{13}$NO: Calculated C, 76.98; H, 6.99; N, 7.48. Found C, 74.46; H, 6.73; N, 7.55.

C. 2-Cyclopropyl-5-methoxy-1H-indole-3-acetic acid methyl ester. As in Example 1, Part C, 4.46 g (0.024 mole) of 2-cyclopropyl-5-methoxy-1H-indole was treated with 15 mL (0.024 mol) of a 1.6M solution of n-butyl lithium in hexane, 24 ml (0.024 mol) of a 1M solution of ZnCl$_2$ in ether, and 12.27 mL (0.024 mol) of methyl 2-bromoacetate to give after chromatography on silica gel (5% EtOAc/toluene→15% EtOAc/toluene) 3.81 g (61%) of 2-cyclopropyl-5-methoxy-1H-indole-3-acetic acid methyl ester as an oil.

Analyses for C$_{15}$H$_{17}$NO$_3$: Calculated C, 69.48; H, 6.61; N, 5.40. Found C, 65.59; H, 6.71; N, 4.85.

D. 2-Cyclopropyl-5-methoxy-1-(phenylmethyl)-1H-indole-3-acetic acid methyl ester. A solution of 3.8 g (146 mmol) of 2-cyclopropyl-5-methoxy-1H-indole-3-acetic acid methyl ester in 50 mL of DMF was treated with 0.59 g (0146 mol) of 60% NaH/mineral oil, stirred 0.5 hour, and 1.69 mL (146 mmol) of benzyl chloride added. After 20 hours, the reaction mixture was diluted with water, extracted with EtOAc, the EtOAc solution was washed four times with water and dried over Na$_2$SO$_4$. After concentrating at reduced pressure, the product was purified by chromatography on silica, eluting with a gradient, 5% EtOAc/toluene→15% EtOAc/toluene, to give 2.05 g (40% yield) of 2-cyclopropyl-5-methoxy-1-(phenylmethyl)-1H-indole-3-acetic acid methyl ester as an oil.

Analyses for C$_{22}$H$_{23}$NO$_3$: Calculated C, 75.62; H, 6.63; N, 4.01. Found C, 75.42; H, 6.66; N, 4.11.

E. 2-Cyclopropyl-5-methoxy-1-(phenylmethyl)-1H-indole-3-acetic acid hydrazide. Using the method described in Example 3, Part C, 2.0 g (5.73 mmol) of 2-cyclopropyl-5-methoxy-1-(phenylmethyl)-1H-indole-3-acetic acid methyl ester was reacted with 3 mL of hydrazine to give after crystallization from ethanol 1.48 g (74% yield) of 2-cyclopropyl-5-methoxy-1-(phenylmethyl)-1H-indole-3-acetic acid hydrazide, 173°–174° C.

Analyses for C$_{21}$H$_{23}$N$_3$O$_2$: Calculated C, 72.18; H, 6.63; N, 12.02. Found C, 71.89; H, 6.66; N, 11.95.

F. 2-Cyclopropyl-5-methoxy-1-(phenylmethyl)-1H-indole-3-acetamide. An ethanol solution of 1.0 g (2.86 mmol) of 2-cyclopropyl-5-methoxy-1-(phenylmethyl)-1H-indole-3-acetic acid hydrazide was reacted with approximately 3 g of Raney nickel as described in Example 6, Part C, and the crude product crystallized from ethanol/water to give 0.47 g (49% yield) of 2-cyclopropyl-5-methoxy-1-(phenylmethyl)-1H-indole-3-acetamide, mp, 156°–158° C.

Analyses: Calc'd for C$_{21}$H$_{22}$N$_2$O$_2$: C, 75.42; H, 6.63; N, 8.38. Found: C, 75.68; H, 6.79; N, 8.46.

Example 78

Preparation of 2-Cyclopropyl-5-hydroxy-1-(phenylmethyl)-1H-indole-3-acetamide

A solution of 400 mg (1.2 mmol) of 2-cyclopropyl-5-methoxy-1-(phenylmethyl)-1H-indole-3-acetamide and 2 mL of 1M BBr$_3$/methylene chloride in 130 mL of methylene chloride was stirred for 1 hour with an ice-water bath and 3 hours at room temperature. The mixture was poured into water, 200 mL of ethyl acetate added, the organic layer separated, washed with brine and dried (Na$_2$SO$_4$). After concentrating at reduced pressure, the residue was crystallized from ethyl acetate to give 300 mg (79% yield) of 2-cyclopropyl-5-hydroxy-1-(phenylmethyl)-1H-indole-3-acetamide, mp, 174°–175° C.

Analyses for C₂₀H₂₀N₂O₂: Calculated C, 74.58; H, 4.29; N, 8.74. Found C, 75.16; H, 4.45; N, 8.72.

Example 79

Preparation of [3-[[3-(2-Amino-2-oxoethyl)-2-cyclopropyl-1-(phenylmethyl)-1H-indol-5-yl]oxy]propyl]phosphonic acid A. [3-[[3-(2-Amino-2-oxoethyl)-2-cyclopropyl-1-(phenylmethyl)-1H-indol-5-yl]oxy]propyl]phosphonic acid dimethyl ester. 2-Cyclopropyl-5-hydroxy-1-(phenylmethyl)-1H-indole-3-acetamide (295 mg.0.9 mmol) was dissolved in 10 mL of THF and 40 mL of DMF and 45 mg (1.1 mmol) of 60% NaH/mineral oil added. After 0.17 hours, 250 mg (1.1 mmol) of (3-bromopropyl)phosphonic acid dimethyl ester was added and stirring maintained for 6.5 hours. The mixture was diluted with water and ethyl acetate, the organic layer separated, washed with water, brine and dried (Na₂SO₄). The solution was evaporated at reduced pressure and the residue chromatographed on silica gel eluting with a gradient, 1% MeOH/methylene chloride→5% MeOH/methylene chloride, to give 280 mg (71% yield) of [3-[[3-(2-amino-2-oxoethyl)-2-cyclopropyl-1-(phenylmethyl)-1H-indol-5-yl]oxy]propyl]phosphonic acid dimethyl ester.

B. [3-[[3-(2-Amino-2-oxoethyl)-2-cyclopropyl-1-(phenylmethyl)-1H-indol-5-yl]oxy]propyl]phosphonic acid. A solution of 280 mg (0.6 mmol) of [3-[[3-(2-amino-2-oxoethyl)-2-cyclopropyl-1-(phenylmethyl)-1H-indol-5-yl]oxy]propyl]phosphonic acid dimethyl ester and 1 mL (7.6 mmol) of trimethylsilyl bromide in 20 mL of methylene chloride was stirred for 19 hours and concentrated at reduced pressure. The residue was dissolved in 10 mL of MeOH, stirred 2 hours and concentrated. This concentrate was crystallized from acetonitrile/ethyl acetate/ether to give 250 mg (94% yield) of [3-[[3-(2-amino-2-oxoethyl)-2-cyclopropyl-1-(phenylmethyl)-1H-indol-5-yl]oxy]propyl]phosphonic acid.

Analyses for C₂₃H₂₇N₂O₅P: Calculated C, 62.44; H, 6.15; N, 6.33. Found C, 51.19; H, 5.37; N, 5.09.

Example 80

Preparation of [3-[[3-(2-Amino-2-oxoethyl)-1-(phenylmethyl)-1H-indol-5-yl]oxy]propyl]phosphonic acid A. 5-Benzyloxy-1H-indole-3-acetic acid ethyl ester. As in Example 1, Part C, 80 g (0.358 mol) of 5-methoxy-1H-indole was treated with 222 mL (0.36 mol) of a 1.6M solution of n-butyl lithium in hexane, 360 ml (0.36 mol) of a 1M solution of ZnCl₂ in ether, and 39.92 mL (0.36 mol) of ethyl 2-bromoacetate to give after chromatography on silica gel (toluene→5% EtOAc/toluene) 30 g (27%) of 5-benzyloxy-1H-indole-3-acetic acid ethyl ester, mp, 57°–59° C.

Analyses for C₁₉H₁₉NO₃: Calculated C, 73.77; H, 6.19; N, 5.43. Found C, 73.75; H, 6.34; N, 4.50.

B. 5-Hydroxy-1H-indole-3-acetic acid ethyl ester. 5-Benzyloxy-1H-indole-3-acetic acid ethyl ester (8.1 g, 20.3 mmol) was hydrogenated in ethanol using 3 g of Raney Ni in 150 mL of ethanol at approximately 40 psi (2.76×10⁵ Pa) of hydrogen. The catalyst was filtered and the filtrate concentrated at reduced pressure. The residue was chromatographed on silica gel eluting with a gradient, 30% ethyl acetate/hexane→50% ethyl acetate/hexane, to give 5.7 g (90% yield) of 5-hydroxy-1H-indole-3-acetic acid ethyl ester.

C. [3-[[3-(2-Ethoxy-2-oxoethyl)-1-(phenylmethyl)-1H-indol-5-yl]oxy]propyl]phosphonic acid dimethyl ester. 5-Hydroxy-1H-indole-3-acetic acid ethyl ester (560 mg.1,8 mmol) was dissolved in 25 mL of THF and 75 mL of DMF and 80 mg (2.0 mmol) of 60% NaH/mineral oil added. After 0.17 hours, 465 mg (2.0 mmol) of (3-bromopropyl)phosphonic acid dimethyl ester was added and stirring maintained for 3.0 hours. The mixture was diluted with water and ethyl acetate, the organic layer separated, washed with water, brine and dried (Na₂SO₄). The solution was evaporated at reduced pressure and the residue chromatographed on florisil eluting with a gradient, 1% MeOH/methylene chloride→3% MeOH/methylene chloride, to give 590 mg (71% yield) of [3-[[3-(2-ethoxy-2-oxoethyl)-1-(phenylmethyl)-1H-indol-5-yl]oxy]propyl]phosphonic acid dimethyl ester.

D. [3-[[3-(2-Amino-2-oxoethyl)-1-(phenylmethyl)-1H-indol-5-yl]oxy]propyl]phosphonic acid dimethyl ester. [3-[[3-(2-Ethoxy-2-oxoethyl)-1-(phenylmethyl)-1H-indol-5-yl]oxy]propyl]phosphonic acid dimethyl ester (590 mg, 1.3 mmol) was dissolved in 40 mL of toluene and 10 mL of 0.67M (CH₃)₂AlNH₂ in benzene/toluene were added. The mixture was heated at 50° C. for 3.25 hours and water and 1N HCl added. The mixture was extracted with a large volume of ethyl acetate and the organic layer was washed with brine, dried (Na₂SO₄) and concentrated at reduced pressure. The residue was chromatographed on silica gel eluting with a gradient, 1% MeOH/methylene chloride→4% MeOH/methylene chloride, to give 450 mg (80% yield) of [3-[[3-(2-amino-2-oxoethyl)-1-(phenylmethyl)-1H-indol-5-yl]oxy]propyl]phosphonic acid dimethyl ester.

E. [3-[[3-(2-Amino-2-oxoethyl)-1-(phenylmethyl)-1H-indol-5-yl]oxy]propyl]phosphonic acid. A solution of 450 mg (1.0 mmol) of [3-[[3-(2-amino-2-oxoethyl)-1-(phenylmethyl)-1H-indol-5-yl]oxy]propyl]phosphonic acid dimethyl ester and 1.5 mL (11 mmol) of trimethylsilyl bromide in 25 mL of methylene chloride was stirred for 16 hours and concentrated at reduced pressure. The residue was dissolved in 10 mL of MeOH, stirred 2 hours and concentrated. This concentrate was crystallized from ethyl acetate/methanol no give 325 mg (81% yield) of [3-[[3-(2-amino-2-oxoethyl)-1-(phenylmethyl)-1H-indol-5-yl]oxy]propyl]phosphonic acid.

Analyses for C₂₀H₂₃N₂O₅P: Calculated C, 59.70; H, 5.76; N, 6.96. Found C, 58.06; H, 5.67; N, 6.41.

Example 81

Preparation of [[3-(2-Amino-2-oxoethyl)-1-(phenylmethyl)-1H-indol-5-yl]oxy]methyl] phosphonic acid disodium salt A. [[3-(2-Ethoxy-2-oxoethyl)-1-(phenylmethyl)-1H-indol-5-yl]oxy]methyl]phosphonic acid dimethyl ester. 5-Hydroxy-1H-indole-3-acetic acid ethyl ester (730 mg.2.4 mmol) was dissolved in 20 mL of THF and 75 mL of DMF and 115 mg (2.8 mmol) of 60% NaH/mineral oil added. After 0.17 hours, 1.1 g (4.0 mmol) of (iodomethyl)phosphonic acid dimethyl ester was added and stirring maintained for 5.5 hours. The mixture was diluted with water and ethyl acetate, the organic layer separated, washed with water, brine and dried (Na₂SO₄). The solution was evaporated at reduced pressure and the residue chromatographed on silica gel eluting with ether to give 150 mg (14% yield) of [[3-(2-ethoxy-2-oxoethyl)-1-(phenylmethyl)-1H-indol-5-yl]oxy]methyl]phosphonic acid dimethyl ester.

B. [[3-(2-Amino-2-oxoethyl)-1-(phenylmethyl)-1H-indol-5-yl]oxy]methyl]phosphonic acid dimethyl ester. [[3-

(2-Ethoxy-2-oxoethyl)-1-(phenylmethyl)-1H-indol-5-yl] oxy]methyl]phosphonic acid dimethyl ester (150 mg, 0.3 mmol) was dissolved in 25 mL of toluene and 10 mL of 0.67M $(CH_3)_2AlNH_2$ in benzene/toluene were added. The mixture was heated at 50° C. for 1.25 hours and water and 1N HCl added. The mixture was extracted with a large volume of ethyl acetate and the organic layer was washed with brine, dried ($Na_2SO_4$) and concentrated at reduced pressure. The residue was chromatographed on silica gel eluting with a gradient, 1% MeOH/methylene chloride→3% MeOH/methylene chloride, to give 120 mg (93% yield) of [[3-(2-amino-2-oxoethyl)-1-(phenylmethyl)-1H-indol-5-yl] oxy]methyl]phosphonic acid dimethyl ester.

C. [[3-(2-Amino-2-oxoethyl)-1-(phenylmethyl)-1H-indol-5-yl]oxy]methyl]phosphonic acid. A solution of 120 mg (0.28 mmol) of [[3-(2-amino-2-oxoethyl)-1-(phenylmethyl)-1H-indol-5-yl]oxy]methyl]phosphonic acid dimethyl ester and 0.5 mL of trimethylsilyl bromide in 20 mL of methylene chloride was stirred for 17 hours and concentrated at reduced pressure. The residue was dissolved in 10 mL of MeOH, stirred 2 hours and concentrated. This concentrate was chromatographed on $C_{18}$ reverse phase column eluting with 80% MeOH/(5% HOAc) and the on a HP-20 column eluting with 10% acetonitrile/water and then 50% acetonitrile/water to give 15 mg (14% yield) of [3-[[3-(2-amino-2-oxoethyl)-1-(phenylmethyl)-1H-indol-5-yl] oxy]methyl]phosphonic acid di sodium salt.

Example 82

Preparation of 5-Hydroxy-1-(phenylmethyl)-1H-indole-3-acetamide

A solution of 375 mg (1.23 mmol) of 5-methoxy-1-(phenylmethyl)-1H-indole-3-acetamide (Example 3) and 5 mL of 1M $BBr_3$/methylene chloride in 75 mL of methylene chloride was stirred for 1.25 hours, and poured into 1N HCl. The methylene chloride layer was separated, washed with brine and dried ($Na_2SO_4$). The solvent was removed at reduced pressure to give as residue 310 mg (90% yield) of 5-hydroxy-1-(phenylmethyl)-1H-indole-3-acetamide, mp, 158°–160° C.

Analyses for $C_{17}H_{16}N_2O_2$: Calculated C, 70.55; H, 5.70; N, 9.51. Found C, 72.84; H, 5.75; N, 9.99.

Example 83

Preparation of 4-[[3-(2-Amino-2-oxoethyl)-1-(phenylmethyl)-1H-indol-5-yl]oxy]butanoic acid A. 4-[[3-(2-Amino-2-oxoethyl)-1-(phenylmethyl)-1H-indol-5-yl]oxy]butanoic acid ethyl ester. A solution of 280 mg (1.0 mmol) of 5-hydroxy-1-(phenylmethyl)-1H-indole-3-acetamide in 30 mL of DMSO and 10 mL of THF was treated with 45 mg (1.1 mmol) of 60% NaH/mineral oil, and then with 0.16 mL (1.1 mmol) of ethyl 4-bromobutyrate. The mixture was heated in an oil bath at 60° C. for 2.25 hours. It was diluted with water, extracted with EtOAc, the EtOAc solution washed with water, saturated NaCl solution, dried ($Na_2SO_4$), and concentrated at reduced pressure. The residue was chromatographed on silica ($CH_2Cl_2$→3% MeOH/ $CH_2Cl_2$) to give 260 mg (66% yield) of 4-[[3-(2-amino-2-oxoethyl)-1-(phenylmethyl)-1H-indol-5-yl]oxy]butanoic acid ethyl ester.

B. 4-[[3-(2-Amino-2-oxoethyl)-1-(phenylmethyl)-1H-indol-5-yl]oxy]butanoic acid. 4-[[3-(2-Amino-2-oxoethyl)-1-(phenylmethyl)-1H-indol-5-yl]oxy]butanoic acid ethyl ester (260 mg, 0.66 mmol) was stirred with 2 mL of 2N NaOH in 25 mL of EtOH and 5 mL of THF for 18 hours. The mixture was acidified with 5N HCl, extracted with EtOAc, the EtOAc solution washed with saturated NaCl solution and dried ($Na_2SO_4$). After concentrating, the residue was crystallized from methylene chloride/ethanol to give 110 mg (46% yield) of 4-[[3-(2-amino-2-oxoethyl)-1-(phenylmethyl)-1H-indol-5-yl]oxy]butanoic acid, mp, 160°–163° C.

Analyses for $C_{21}H_{22}N_2O_4$: Calculated C, 68.84; H, 6.05; N, 7.65. Found C, 68.98; H, 5.89; N, 7.82.

Example 84

Preparation of 3-[4-[[3-(2-Amino-2-oxoethyl)-2-methyl-1-(phenylmethyl)-1H-indol-5-yl]oxy] propane]sulfonic acid 5-Hydroxy-2-methyl-1-(phenylmethyl)-1H-indole-3-acetamide (Example 2, 300 mg, 1.0 mmol) was dissolved in 50 mL of THF, 40 mg (1.0 mmol) of 60% NaH/mineral oil added, stirred 0.25 hours, 125 mg (1.0 mmol) of sultone added and the mixture stirred for 24 hours. The mixture was made acidic with 5N HCl and the concentrated at reduced pressure. The residue was crystallized from ethanol/water to give 145 mg (35% yield) of 3-[4-[[3-(2-amino-2-oxoethyl) -2-methyl-1-(phenylmethyl)-1H-indol-5-yl]oxy]propane] sulfonic acid, mp, 218°–222° C.

Analyses for $C_{21}H_{24}N_2O_4S$: Calculated C, 60.56; H, 5.81; N, 6.73; S, 7.70. Found C, 53.36; H, 5.66; N, 5.44; S, 3.30; residue, 15.32.

Example 85

Preparation of 3-[4-[[3-(2-Amino-2-oxoethyl)-2-ethyl-1-(phenylmethyl)-1H-indol-5-yl]oxy]propane] sulfonic acid 5-Hydroxy-2-ethyl-1-(phenylmethyl)-1H-indole-3-acetamide (310 mg, 1.0 mmol) was dissolved in 50 mL of THF, 50 mg (1.2 mmol) of 60% NaH/mineral oil added, stirred 0.25 hours, 150 mg (1.2 mmol) of sultone added and the mixture stirred for 24 hours. The mixture was acidified with 1.5 mL of 1N HCl and concentrated at reduced pressure. The residue was chromatographed on an C-18 reverse phase column (eluted with 10% (5% HOAc)/MeOH) to give 260 mg (60% yield) of 3-[4-[[3-(2-amino-2-oxoethyl)-2-ethyl-1-(phenylmethyl)-1H-indol-5-yl]oxy]propane] sulfonic acid.

Analyses for $C_{22}H_{26}N_2O_5S$: Calculated C, 61.38; H, 6.09; N, 6.51; S, 7.45. Found C, 56.00; H, 5.79; N, 5.52; S, 3.85; residue, 11.60.

Example 86

Preparation of [3-[[3-(2-Amino-2-oxoethyl)-2-bromo-1-(phenylmethyl)-1H-indol-5-yl]oxy] propane]phosphonic acid dimethyl ester A. 5-Methoxy-1-(phenylmethyl)-1H-indole-3-acetic acid ethyl ester. 5-Methoxy-1H-indole-3-acetic acid ethyl ester (10.1 g, 41 mmol) was dissolved in 50 mL of THF and 200 mL of DMF and 1.8 g (45 mmol) of 60% NaH/mineral oil were added in portions with cooling. After 0.17 hours, 5 mL (42 mmol) of benzyl bromide was added and stirring maintained for 1.5 hours. The mixture was diluted with water and ethyl acetate, the organic layer separated, washed with water, brine and dried ($Na_2SO_4$). The solution was evaporated at reduced pressure and the residue chromatographed on silica gel eluting with a gradient, 25% ethyl acetate/ hexane→40% ethyl acetate/hexane, to give 10.8 g (82% yield) of 5-methoxy-1-(phenylmethyl)-1H-indole-3-acetic acid ethyl ester.

B. 2-Bromo-5-methoxy-1-(phenylmethyl)-1H-indole-3-acetic acid ethyl ester. A mixture of 5-methoxy-1-(phenylmethyl)-1H-indole-3-acetic acid ethyl ester (10.8 g, 32 mmol) and 6.3 g (35 mmol) of N-bromosuccinimide in 250 mL of carbon tetrachloride was stirred for 1.5 hours, washed with $Na_2S_2O_3$ solution, water, brine, and dried ($Na_2SO_4$). After concentrating at reduced pressure, the residue was chromatographed on silica gel and eluted with a gradient, 25% ether/hexane→40% ether/hexane, to give 5.5 g (43% yield) of 2-bromo-5-methoxy-1-(phenylmethyl)-1H-indole-3-acetic acid ethyl ester.

There was obtained a second fraction from the chromatography, 6.4 g. This material was reacted with 6.3 g of NBS as above and rechromatographed on silica gel eluting with 30% ether/hexane→50% ether/hexane to give 5.4 g of 2,4-dibromo-5-methoxy-1-(phenylmethyl)-1H-indole-3-acetic acid ethyl ester After crystallizing from methylene chloride this material melted at 138°–140° C.

Analyses for $C_{20}H_{19}Br_2NO_3$: Calculated C, 49.92; H, 3.98; N, 2.91; Br, 33.21. Found C, 49.95; H, 4.15; N, 2.89; Br, 33.52.

C. 2-Bromo-5-methoxy-1-(phenylmethyl)-1H-indole-3-acetamide. A mixture of 4 g (10 mmol) of 2-bromo-5-methoxy-1-(phenylmethyl)-1H-indole-3-acetic acid ethyl ester and 50 mL of 0.67M $(CH_3)_2AlNH_2$/benzene/toluene in 100 mL of toluene was heated at 50° C. for 7.5 hours, cooled, decomposed with ice and dilute HCl added. The mixture was extracted with ethyl acetate and the ethyl acetate solution washed with brine, dried ($Na_2SO_4$), and concentrated at reduced pressure. The residue of 2-bromo-5-methoxy-1-(phenylmethyl)-1H-indole-3-acetamide weighed 4.0 g.

D. 2-Bromo-5-hydroxy-1-(phenylmethyl)-1H-indole-3-acetamide. A solution of 4 g (11 mmol) of 2-bromo-5-methoxy-1-(phenylmethyl)-1H-indole-3-acetamide and 35 mL of $BBr_3$/methylene chloride in 200 mL of methylene chloride was stirred for 1 hour, poured into ice-water, made basic with sodium bicarbonate and extracted with methylene chloride. This solution was washed with brine, dried ($Na_2SO_4$) and concentrated. The residue was chromatographed on silica gel and eluted with ethyl acetate to give 1.35 g (33% yield) of 2-bromo-5-hydroxy-1-(phenylmethyl)-1H-indole-3-acetamide.

E. [3-[[3-(2-Amino-2-oxoethyl)-2-bromo-1-(phenylmethyl)-1H-indol-5-yl]oxy]propyl]phosphonic acid dimethyl ester. Using the procedure described in Example 81, Part A, 1.35 g (3.8 mmol) of 2-bromo-5-hydroxy-1-(phenylmethyl)-1H-indole-3-acetamide was reacted with 170 mg (4.2 mmol) of NaH/mineral oil and then 970 mg (4.2 mmol) of (3-bromopropyl)phosphonic acid dimethyl ester to give a product that was chromatographed on silica gel (eluted with a gradient, 1% MeOH/methylene chloride→3% MeOH/methylene chloride). There was obtained 520 g (27% yield) of 3-[[3-(2-amino-2-oxoethyl)-2-bromo-1-(phenylmethyl)-1H-indol-5-yl]oxy]propyl]phosphonic acid dimethyl ester, melting approximately at 100° C. after crystallizing from methylene chloride/ether.

Analyses for $C_{22}H_{26}BrN_2O_5P$: Calculated C, 51.88; H, 5.15; N, 5.50; Br, 15.69. Found C, 47.83; H, 4.83; N, 4.85; Br, 20.07.

Example 87

Preparation of 3-[[3-(2-Amino-2-oxoethyl)-2-bromo-1-(phenylmethyl)-1H-indol-5-yl]oxy]propyl] phosphonic acid monomethyl ester A mixture of 255 mg (0.5 mmol) of 3-[[3-(2-amino-2-oxoethyl)-2-bromo-1-(phenylmethyl)-1H-indol-5-yl]oxy] propyl]phosphonic acid dimethyl ester and 2 mL of 2N NaOH in 20 mL of MeOH was heated to maintain reflux for 23 hours, diluted with water and extracted with ethyl acetate. The aqueous layer was made acidic with 5N HCl and extracted with ethyl acetate. The ethyl acetate was washed with brine, dried ($Na_2SO_4$) and evaporated at reduced pressure to give 210 mg (84% yield) of 3-[[3-(2-amino-2-oxoethyl)-2-bromo-1-(phenylmethyl)-1H-indol-5-yl]oxy] propyl]phosphonic acid monomethyl ester.

Analyses for $C_{21}H_{24}BrN_2O_5P$: Calculated C, 50.92; H, 4.58; N, 5.66; Br, 16.09. Found C, 50.08; H, 4.68; N, 4.18; Br, 17.33.

Example 88

Preparation of 3-[[3-(2-Amino-2-oxoethyl)-2-bromo-1-(phenylmethyl)-1H-indol-5-yl]oxy]propyl] phosphonic acid A solution of 750 mg (1.5 mmol) of 3-[[3-(2-amino-2-oxoethyl)-2-bromo-1-(phenylmethyl)-1H-indol-5-yl]oxy] propyl]phosphonic acid dimethyl ester and 2 mL (15 mmol) of trimethylsilyl bromide in 75 mL of methylene chloride was stirred for 18.5 hours and concentrated at reduced pressure. The residue was dissolved in 75 mL of methanol stirred for 1.5 hours and concentrated. The residue was crystallized from ethyl acetate/ethanol/methylene chloride to give 285 mg (39% yield) of 3-[[3-(2-amino-2-oxoethyl)-2-bromo-1-(phenylmethyl)-1H-indol-5-yl]oxy]propyl] phosphonic acid, mp, 188°–190° C.

Analyses for $C_{20}H_{22}BrN_2O_5P$: Calculated C, 49.91; H, 4.61; N, 5.82; Br, 15.53. Found C, 47.99; H, 4.73; N, 5.37; Br, 17.80.

The filtrate from the above crystallization was concentrated at reduced pressure and the residue chromatographed on a C-18 reverse phase column eluting with 5% (5% HOAc)/MeOH. This fraction was dissolved in 0.05N NaOH and put on a medium pressure HP-20 column and eluted with 10% acetonitrile/water>50% acetonitrile/water to give 195 mg of 3-[[3-(2-amino-2-oxoethyl)-2-bromo-1-(phenylmethyl)-1H-indol-5-yl]oxy]propyl]phosphonic acid disodium salt.

Analyses for $C_{20}H_{20}BrN_2O_5PNa_2$: Calculated C, 46.51; H, 3.90; N, 4.83; Br, 14.00. Found C, 45.73; H, 3.84; N, 5.33; Br, 15.16.

Example 89

Preparation of 2-Bromo-6-chloro-5-methoxy-1-(phenylmethyl)-H-indole-3-acetamide

A. 6-Chloro-5-methoxy-1H-indole-3-acetic acid methyl ester. Using the procedure in Example 1, Part C, 5.2 g (28.6 mmol) of 6-chloro-5-methoxy-1H-indole was reacted with 18,13 mL (29 mmol) of n-butyl lithium and 29 mL of 1N $ZnCl_2$/ether and then 2.75 mL of methyl 2-bromoacetate to give a product that was chromatographed on silica gel (eluted with 5% EtOAc/toluene→10% EtOAc/toluene). There was obtained 4.66 g (64% yield) of 6-chloro-5-methoxy-1H-indole-3-acetic acid methyl ester as an oil Analyses for $C_{12}H_{12}ClNO_3$: Calculated C, 56.82; H, 4.77; N, 5.52. Found C, 56.61; H, 4.81; N, 5.52.

B. 6-Chloro-5-methoxy-1-(phenylmethyl)-H-indole-3-acetic acid methyl ester. 6-Chloro-5-methoxy-1H-indole-3-acetic acid methyl ester (2.0 g, 8 mmol) was dissolved in 75 mL of DMF and 20 mL of THF, 340 mg (8.5 mmol) of 60% NaH/mineral oil added, stirred 0.17 hours and 1.1 mL (9.2 mmol) of benzyl bromide added. After 0.75 hours, the mixture was added to water, extracted with ethyl acetate, the ethyl acetate solution washed with water, brine, dried ($Na_2SO_4$) and concentrated at reduced pressure. The residue was chromatographed on silica gel eluting with 20% ether/hexane→50% ether/hexane to give 1.8 g (67% yield) of 6-chloro-5-methyoxy-1-(phenylmethyl)-H-indole-3-acetic acid methyl ester after crystallization from ether/hexane, mp, 64°–66° C.

Analyses for $C_{19}H_{18}ClNO_3$: Calculated C, 66.38; H, 5.08; N, 4.07; CL, 10.31. Found C, 66.37; H, 5.25; N, 4.13; Cl, 10.07.

C. 2-Bromo-6-chloro-5-methoxy-1-(phenylmethyl)-H-indole-3-acetic acid methyl ester. A mixture of 1.0 g (3.0 mmol) of 6-chloro-5-methyoxy-1-(phenylmethyl)-H-indole-3-acetic acid methyl ester and 600 mg (3.3 mmol) of NBS in 100 mL of carbon tetrachloride was stirred for 30 hours. The mixture was washed with $Na_2S_2O_3$ solution, brine, dried ($Na_2SO_4$) and concentrated at reduced pressure. The residue was chromatographed on silica gel and eluted with a gradient, 20% ether/hexane→100% ether, to give 1.0 g (79% yield) of 2-bromo-6-chloro-5-methoxy-1-(phenylmethyl)-H-indole-3-acetic acid methyl ester that melted at 133°–134° C. after crystallization from methylene chloride/ether.

Analyses for $C_{19}H_{17}BrClNO_3$: Calculated C, 53.99; H, 4.05; N, 3.31; Br, 18.90; Cl, 8.40. Found C, 54.70; H, 4.11; N, 3.38; Br, 16.04; Cl, 9.97.

D. 2-Bromo-6-chloro-5-methoxy-1-(phenylmethyl)-H-indole-3-acetamide. A mixture of 950 mg (2.18 mmol) of 2-bromo-6-chloro-5-methoxy-1-(phenylmethyl)-H-indole-3-acetic acid methyl ester and 20 mL of 0.67M $(CH_3)_2AlNH_2$/benzene/toluene in 75 mL of benzene was heated at 50° C. for 1.5 hour, cooled, decomposed with ice and dilute HCl added. The mixture was extracted with ethyl acetate and the ethyl acetate solution washed with brine, dried ($Na_2SO_4$), and concentrated at reduced pressure. The residue of was crystallized from ethanol/methylene chloride to give 580 mg (65% yield) of 2-bromo-6-chloro-5-methoxy-1-(phenylmethyl)-H-indole-3-acetamide, mp, 205° C. (decomposition).

Analyses for $C_{18}H_{16}BrClN_2O_2$: Calculated C, 53.03; H, 3.96; N, 6.87; Br, 19.60; Cl, 8.70. Found C, 53.72; H, 4.42; N, 6.97; Br, 19.26; Cl, 9.36.

Example 90

Preparation of 2-Bromo-6-chloro-5-hydroxy-1-(phenylmethyl)-H-indole-3-acetamide

A solution of 730 mg (1.8 mmol) of 2-bromo-6-chloro-5-methoxy-1-(phenylmethyl)-H-indole-3-acetamide and 10 mL of 1N $BBr_3$/methylene chloride in 75 mL of methylene chloride was stirred for 2.5 hours, 1N HCl added and stirred. The organic solution was separated, washed with brine, dried ($Na_2SO_4$) and concentrated at reduced pressure. The residue was chromatographed on silica gel eluting with 2% MeOH/methylene chloride→4% MeOH/methylene chloride to give 280 mg (45% yield) of 2-bromo-6-chloro-5-hydroxy-1-(phenylmethyl)-H-indole-3-acetamide, mp, 195° C. (decomposition).

Analyses for $C_{17}H_{14}BrClN_2O_2$: Calculated C, 51.87; H, 3.59; N, 7.17; Br, 20.30; Cl, 9.01. Found C, 50.96; H, 3.66; N, 6.69; Br, 19.48; Cl, 9.49.

Example 91

Preparation of 4-[[3-(2-Amino-2-oxoethyl)-2-bromo-6-chloro-1-(phenylmethyl)-1H-indol-5-yl] oxy]butanoic acid A. 4-[[3-(2-Amino-2-oxoethyl)-2-bromo-6-chloro-1-(phenylmethyl)-1H-indol-5-yl]oxy]butanoic acid ethyl ester. Using the procedure in Example 83, Part A, 235 mg (0.6 mmol) of 2-bromo-6-chloro-5-hydroxy-1-(phenylmethyl)-H-indole-3-acetamide was treated with 25 mg (0.6 mmol) of 60% NaH/mineral oil and then 0.1 mL (0.7 mmol) of ethyl 4-bromobutyrate to give a product that was chromatographed on silica gel. A gradient of methylene chloride→2% MeOH/methylene was used to elute 210 mg (69% yield) of 4-[[3-(2-amino-2-oxoethyl)-2-bromo-6-chloro-1-(phenylmethyl)-1H-indol-5-yl]oxy]butanoic acid ethyl ester.

B. 4-[[3-(2-Amino-2-oxoethyl)-2-bromo-6-chloro-1-(phenylmethyl)-1H-indol-5-yl]oxy]butanoic acid. A mixture of 210 mg (0.41 mmol) of 4-[[3-(2-amino-2-oxoethyl)-2-bromo-6-chloro-1-(phenylmethyl)-1H-indol-5-yl]oxy] butanoic acid ethyl ester and 2 mL of 2N NaOH in 5 mL of THF and 25 mL of ethanol was stirred for 10.5 hours, the mixture made acidic with 5N HCl and extracted with ethyl acetate. The ethyl acetate solution was washed with brine, dried ($Na_2SO_4$) and concentrated at reduced pressure. The residue was crystallized from methylene chloride/ethanol to give 60 mg (31% yield) of 4-[[3-(2-amino-2-oxoethyl)-2-bromo-6-chloro-1-(phenylmethyl)-1H-indol-5-yl]oxy] butanoic acid, 220° C. (decomposition).

Analyses for $C_{21}H_{20}BrClN_2O_4$: Calculated C, 52.57; H, 4.20; N, 5.84; Br, 16.65; Cl, 7.39. Found C, 54.03; H, 4.45; N, 5.80; Br, 11.57; Cl, 8.96; residue, 1.35.

Example 92

Preparation of 3-[4-[[3-(2-Amino-2-oxoethyl)-6-chloro-1-(phenylmethyl)-1H-indol-5-yl]oxy]propyl] phosphonic acid A. 6-Chloro-5-methoxy-1-(phenylmethyl)-H-indole-3-acetamide. By the method in Example 89, Part D, 1.1 g (3.2 mmol) of 6-chloro-5-methoxy-1-(phenylmethyl)-H-indole-3-acetic acid methyl ester (Example 89, Part B) and 20 mL of $(CH_3)_2AlNH_2$/benzene/toluene in 40 mL of benzene were reacted to give 970 mg (88% yield) of 6-chloro-5-methyoxy-1-(phenylmethyl)-H-indole-3-acetamide.

B. 6-Chloro-5-hydroxy-1-(phenylmethyl)-H-indole-3-acetamide. A solution of 970 mg (2.8 mmol) of 6-chloro-5-methoxy-1-(phenylmethyl)-H-indole-3-acetamide and 10 mL of 1N $BBr_3$/methylene chloride in 100 mL of methylene chloride was stirred for 5 hours, 1N HCl added and stirred. The organic solution was separated, washed with brine, dried ($Na_2SO_4$) and concentrated at reduced pressure. The residue was chromatographed on silica gel eluting with 1% MeOH/methylene chloride→3% MeOH/methylene chloride to give 470 mg (53% yield) of 6-chloro-5-hydroxy-1-(phenylmethyl)-H-indole-3-acetamide.

C. 3-[4-[[3-(2-Amino-2-oxoethyl)-6-chloro-1-(phenylmethyl)-1H-indol-5-yl]oxy]propyl]phosphonic acid dimethyl ester. Using the method in Example 80, Part C, 470 mg (1.5 mmol) of 6-chloro-5-hydroxy-1-(phenylmethyl)-H-indole-3-acetamide was reacted with 75 mg (1.8 mmol) of 60% NaH/mineral oil and 415 mg (1.8 mmol) of (3-bromopropyl)phosphonic acid dimethyl ester to give a product that was chromatographed on silica gel. On eluting with 1% MeOH/methylene chloride→4% MeOH/methylene chloride, there was obtained 400 mg (57% yield) of 3-[4-[ [3-(2-amino-2-oxoethyl)-6-chloro-1-(phenylmethyl)-1H-indol-5-yl]oxy]propyl]phosphonic acid dimethyl ester.

D. 3-[4-[[3-(2-Amino-2-oxoethyl)-6-chloro-1-(phenylmethyl)-1H-indol-5-yl]oxy]propyl]phosphonic acid. 3-[4-[[3-(2-Amino-2-oxoethyl)-6-chloro-1-(phenylmethyl)-1H-indol-5-yl]oxy]propyl]phosphonic acid dimethyl ester 400 mg (0.86 mmol) was treated with 1 mL of trimethylsilyl bromide in 30 mL of methylene chloride as in Example 80, Part E, to give after crystallizing from acetonitrile/ethyl acetate/ether, 235 mg (63% yield) of 3-[4-[[3-(2-amino-2-oxoethyl)-6-chloro-1-(phenylmethyl)-1H-indol-5-yl]oxy]propyl]phosphonic acid.

Analyses for $C_{20}H_{22}ClN_2O_5P$: Calculated C, 54.99; H, 5.08; N, 6.41; Cl, 8.12. Found C, 49.82; H, 5.03; N, 7.71; Cl, 9.86.

Example 93

Preparation of 4-Allyl-2-ethyl-5-hydroxy-1-(phenylmethyl)-1H-indole-acetamide

A. 5-Allyloxy-2-ethyl-1-(phenylmethyl)-1H-indole-acetamide. 2-Ethyl-5-hydroxy-1-(phenylmethyl)-1H-indole-acetamide (620 mg, 2.0 mmol, Example 9) was dissolved in 10 mL of THF and 40 mL of DMF, 90 mg (2.2 mmol) of 60% NaH/mineral oil added and after stirring 0.17 hours, 0.2 mL (2.3 mmol) of allyl bromide was added. After 2 hours, the mixture was diluted with water and extracted with ethyl acetate. The ethyl acetate solution was washed with brine, dried ($Na_2SO_4$) and concentrated at reduced pressure. The residue was chromatographed on silica gel (eluted with 1% MeOH methylene chloride→3% MeOH/ methylene chloride) to give 770 mg of 5-allyloxy-2-ethyl-1-(phenylmethyl)-1H-indole-acetamide.

B. 4-Allyl-2-ethyl-5-hydroxy-1-(phenylmethyl)-1H-indole-acetamide. 5-Allyloxy-2-ethyl-1-(phenylmethyl)-1H-indole-acetamide (770 mg, 2.21 mmol) in 20 mL of N,N-dimethylaniline were heated in an oil bath at 190° C. for 20 hours. The mixture was cooled, diluted with ethyl acetate, washed with 1N HCl, brine, dried ($Na_2SO_4$) and concentrated at reduced pressure. The residue was chromatographed on silica gel and eluted with 1% MeOH methylene chloride→3% MeOH/methylene chloride to give 295 mg (38% yield) of 4-allyl-2-ethyl-5-hydroxy-1-(phenylmethyl)-1H-indole-acetamide.

Analyses for $C_{22}H_{24}N_2O_2$: Calculated C, 75.83; H, 6.74; N, 8.04. Found C, 75.70; H, 7.05; N, 8.06.

Example 94

Preparation of [3-[[4-Allyl-3-(2-amino-2-oxoethyl)-2-ethyl-1-(phenylmethyl)-1H-indol-5-yl]oxy]propyl] phosphonic acid disodium salt A. [3-[[4-Allyl-3-(2-amino-2-oxoethyl)-2-ethyl-1-(phenylmethyl)-1H-indol-5-yl]oxy]propyl]phosphonic acid dimethyl ester. Using the method in Example 80, Part C, 265 mg (0.8 mmol) of 4-allyl-2-ethyl-5-hydroxy-1-(phenylmethyl)-1H-indole-acetamide was reacted with 40 mg (1.0 mmol) of 60% NaH/mineral oil and 230 mg (1.0 mmol) of (3-bromopropyl)phosphonic acid dimethyl ester to give a product that was chromatographed on silica gel. On eluting with 1% MeOH/methylene chloride→4% MeOH/ methylene chloride, there was obtained 310 mg (78% yield) of [3-[[4-allyl-3-(2-amino-2-oxoethyl)-2-ethyl-1-(phenylmethyl)-1H-indol-5-yl]oxy]propyl]phosphonic acid dimethyl ester.

B. [3-[[4-Allyl-3-(2-amino-2-oxoethyl)-2-ethyl-1-(phenylmethyl)-1H-indol-5-yl]oxy]propyl]phosphonic acid disodium salt. A solution of 310 mg (0.62 mmol) of [[3-allyl-3-(2-amino-2-oxoethyl)-2-ethyl-1-(phenylmethyl)-1H-indol-5-yl]oxy]propyl]phosphonic acid dimethyl ester and 1.0 mL (7.6 mmol) of trimethylsilyl bromide in 20 mL of methylene chloride was stirred for 18.5 hours and concentrated at reduced pressure. The residue was dissolved in 20 mL of MeOH, stirred 2.5 hours and concentrated. This residue was chromatographed on a $C_{18}$ reverse phase column and eluted with 10% (5% HOAc)/MeOH. Material from this column was dissolved in 1N NaOH and chromatographed on a HP20 column. The product was eluted with 10% acetonitrile/water, then 25% acetonitrile/water to give 165 mg (52% yield) of [3-[[4-allyl-3-(2-amino-2-oxoethyl)-2-ethyl-1-(phenylmethyl)-1H-indol-5-yl]oxy]propyl] phosphonic acid disodium salt.

Analyses for $C_{25}H_{29}N_2O_5PNa_2 \cdot 3H_2O$: Calculated C, 52.82; H, 6.21; N, 4.93. Found C, 52.15; H, 5.50; N, 4.65.

Example 95

Preparation of 2-Methyl-5-phenoxy-1-(phenylmethyl)-1H-indole-3-acetamide

5-Hydroxy-2-methyl-1-(phenylmethyl)-1H-indole-3-acetamide (1.2 g, 4.1 mmol) was dissolved in 40 mL of pyridine, 90 mg (2.2 mmol) of 60% NaH/mineral oil added, stirred 0.17 hours, 315 mg of CuO added, stirred 0.17 hours and 0.5 (4.1 mmol) mL of iodobenzene added. The mixture was heated to maintain reflux for 24 hours, cooled, and diluted with ethyl acetate and 1N HCl. The mixture was filtered thru a celite pad and the organic material separated, washed with brine, dried ($Na_2SO_4$) and concentrated at reduced pressure. The residue was chromatographed on silica gel and eluted with 1% MeOH/methylene chloride→3% MeOH/methylene chloride to give 40 mg (3% yield) of 2-methyl-5-phenoxy-1-(phenylmethyl)-1H-indole-3-acetamide.

Example 96

Preparation of 2-[[[3-(2-Amino-2-oxoethyl)-2-methyl-1-(phenylmethyl)-1H-indol-5-yl]oxy]methyl] benzoic acid methyl ester Using the procedure in Example 83, Part A, 300 mg (1.0 mmol) of 5-hydroxy-2-methyl-1-(phenylmethyl)-H-indole-3-acetamide was treated with 45 mg (1.1 mmol) of 60% NaH/mineral oil and then 250 m (1.1 mmol) of methyl 2-(bromomethyl)benzoate to give a product that was chromatographed on silica gel. A gradient of methylene chloride→2% MeOH/methylene was used to elute 270 mg (69% yield) of 2-[[[3-(2-amino-2-oxoethyl)-2-methyl-1-(phenylmethyl)-1H-indol-5-yl]oxy]methyl]benzoic acid methyl ester, mp, 178°–180° C.

Analyses for $C_{27}H_{26}N_2O_4$: Calculated C, 73.28; H, 5.92; N, 6.33. Found C, 72.29; H, 5.93; N, 6.03.

Example 97

Preparation of 2-[[[3-(2-Amino-2-oxoethyl)-2-methyl-1-(phenylmethyl)-1H-indol-5-yl]oxy]methyl] benzoic acid A mixture of 195 mg (0.44 mmol) of 2-[[[3-(2-amino-2-oxoethyl)-2-methyl-1-(phenylmethyl)-1H-indol-5-yl]oxy] methyl]benzoic acid methyl ester and 2 mL of 2N NaOH in 10 mL of THF and 35 mL of ethanol was stirred for 17.5 hours, the mixture made acidic with 5N HCl and extracted with ethyl acetate. The ethyl acetate solution was washed with brine, dried ($Na_2SO_4$) and concentrated at reduced pressure. The residue was crystallized from methylene chloride to give 110 mg (59% yield) of 2-[[[3-(2-amino-2-oxoethyl)-2-methyl-1-(phenylmethyl)-1H-indol-5-yl]oxy] methyl]benzoic acid, mp, 173°–176° C.

Example 98

Preparation of 2-[[[3-(2-Amino-2-oxoethyl)-2-ethyl-1-(phenylmethyl)-1H-indol-5-yl]oxy]methyl]benzoic acid methyl ester Using the procedure in Example 83, Part A, 620 mg (2.0 mmol) of 5-hydroxy-2-ethyl-1-(phenylmethyl)-H-indole-3-acetamide was treated with 90 mg (2.2 mmol) of 60% NaH/mineral oil and then 505 mg (2.2 mmol) of methyl 2-(bromomethyl)benzoate to give a product that was chromatographed on silica gel. A gradient of 1% MeOH/methylene chloride→2% MeOH/methylene was used to elute 160 mg (18% yield) of 2-[[[3-(2-amino-2-oxoethyl)-2-ethyl-1-(phenylmethyl)-1H-indol-5-yl]oxy]methyl]benzoic acid methyl ester, mp, 132°–134° C.

Analyses for $C_{28}H_{28}N_2O_4$: Calculated C, 73.66; H, 6.18; N, 6.14. Found C, 74.36; H, 6.20; N, 5.82.

Example 99

Preparation of 2-[[[3-(2-Amino-2-oxoethyl)-2-ethyl-1-(phenylmethyl)-1H-indol-5-yl]oxy]methyl]benzoic acid A mixture of 495 mg (1.08 mmol) of 2-[[[3-(2-amino-2-oxoethyl)-2-ethyl-1-(phenylmethyl)-1H-indol-5-yl]oxy]methyl]benzoic acid methyl ester and 2 mL of 5N NaOH in 25 mL of ethanol was stirred for 17 hours, the mixture made acidic with 5N HCl and extracted with ethyl acetate. The ethyl acetate solution was washed with brine, dried ($Na_2SO_4$) and concentrated at reduced pressure. The residue was crystallized from methylene chloride/ether to give 440 mg (92% yield) of 2-[[[3-(2-amino-2-oxoethyl)-2-ethyl-1-(phenylmethyl)-1H-indol-5-yl]oxy]methyl]benzoic acid, mp, approximately 100° C.

Example 100

Preparation of 3-[[[3-(2-Amino-2-oxoethyl)-2-methyl-1-(phenylmethyl)-1H-indol-5-yl]oxy]methyl]benzoic acid methyl ester Using the procedure in Example 83, Part A, 910 mg (3.0 mmol) of 5-hydroxy-2-methyl-1-(phenylmethyl)-H-indole-3-acetamide was treated with 135 mg (3.3 mmol) of 60% NaH/mineral oil and then 760 m (3.3 mmol) of methyl 3-(bromomethyl)benzoate to give a product that was chromatographed on silica gel. A gradient of 1% MeOH/methylene chloride→3% MeOH/methylene was used to elute a product that was recrystallized from methylene chloride/ethanol. A yield of 885 mg (69%) of 3-[[[3-(2-amino-2-oxoethyl)-2-methyl-1-(phenylmethyl)-1H-indol-5-yl]oxy]methyl]benzoic acid methyl ester was obtained, mp, 147°–149° C.

Analyses for $C_{27}H_{26}N_2O_4$: Calculated C, 73.28; H, 5.92; N, 6.33. Found C, 73.03; H, 5.86; N, 6.22.

Example 101

Preparation of 3-[[[3-(2-Amino-2-oxoethyl)-2-methyl-1-(phenylmethyl)-1H-indol-5-yl]oxy]methyl]benzoic acid A mixture of 470 mg (1.06 mmol) of 3-[[[3-(2-amino-2-oxoethyl)-2-methyl-1-(phenylmethyl)-1H-indol-5-yl]oxy] methyl]benzoic acid methyl ester and 2 mL of 2N NaOH in 10 mL of THF and 40 mL of ethanol was stirred for 7.5 hours, the mixture made acidic with 5N HCl and extracted with ethyl acetate. The ethyl acetate solution was washed with brine, dried ($Na_2SO_4$) and concentrated at reduced pressure. The residue was crystallized from methylene chloride/ethanol to give 330 mg (72% yield) of 3-[[[3-(2-amino-2-oxoethyl)-2-methyl-1-(phenylmethyl)-1H-indol-5-yl]oxy]methyl]benzoic acid, mp, 176°–179° C.

Analyses for $C_{26}H_{24}N_2O_4$: Calculated C, 72.88; H, 5.65; N, 6.54. Found C, 70.01; H, 5.55; N, 6.11.

Therapeutic use of 1H-indole-3-acetamides

Tests of the 1H-indole-3-acetamides described herein have shown they achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting $sPLA_2$ with an therapeutically effective amount of the 1H-indole-3-acetamides of the invention and pharmaceutically acceptable salts thereof.

A preferred method of the invention comprises contacting $sPLA_2$ with an therapeutically effective amount of 1H-indole-3-acetamide and pharmaceutically acceptable salts thereof where said acetamide is substituted at the 4 and/or 5 position with an -oxyalkyl acid, -oxyalkyl ester, -oxyalkylamine, -oxybenzyl (where the phenyl group of the benzyl radical is substituted with an acid group, ester group, amine group, or suitable salt thereof); and is substituted at the 1 position with a benzyl or biphenyl group and pharmaceutically acceptable salts thereof. Still another preferred method of the invention comprises contacting $sPLA_2$ with an therapeutically effective amount of 1H-indole-3-acetamide, where said acetamide is substituted at the 4 and/or 5 position with an acidic group, and is substituted at the 2 position with a group containing oxygen, nitrogen or sulfur group, and pharmaceutically acceptable salts thereof.

The preferred novel compounds of this invention are most preferably used for practicing the method of inhibiting $sPLA_2$ mediated release of fatty acids. This method comprises contacting $sPLA_2$ with an therapeutically effective amount of 1H-indole-3-acetamide and pharmaceutically acceptable salts thereof, represented by the formula (VI):

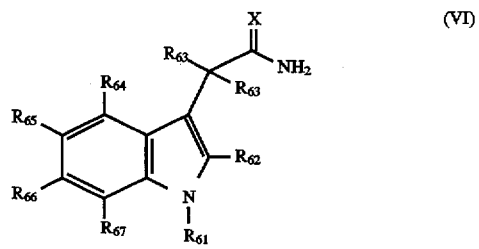

X is oxygen or sulfur;

$R_{61}$ is selected from groups (i), (ii) and (iii) where;
  (i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or
  (ii) is aryl or aryl substituted by halo, —CN, —CHO, —OH, —SH, $C_1$–$C_{10}$ alkylthio, $C_1$–$C_{10}$ alkoxylthio, carboxyl, amino, or hydroxyamino;

(iii) is

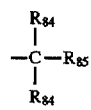

where $R_{84}$ is hydrogen or $C_1$–$C_{10}$ alkyl, and $R_{85}$ is selected from the group; phenyl, naphthyl, indenyl, and biphenyl, unsubstituted or substituted by halo, —CN, —CHO, —OH, nitro, phenyl, —SH, $C_1$–$C_{10}$ alkylthio, $C_1$–$C_{10}$ alkoxyl, amino, hydroxyamino or a substituted or unsubstituted 5 to 8 membered heterocyclic ring;

$R_{62}$ is hydrogen, halo, $C_1$–$C_3$ alkyl, ethenyl, cyclopropyl, $C_1$–$C_2$ alkylthio, $C_1$–$C_2$ alkoxy, —CHO, —CN;

each $R_{63}$ is independently hydrogen, or halo;

$R_{64}$, $R_{65}$, $R_{66}$, and $R_{67}$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or any two adjacent hydrocarbyl groups in the set $R_{64}$, $R_{65}$, $R_{66}$, and $R_{67}$, combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazide, hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

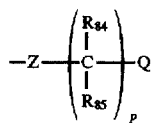

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON(R$_{82}$R$_{83}$), -5-tetrazolyl, —SO$_3$H,

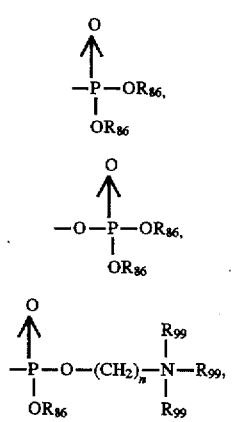

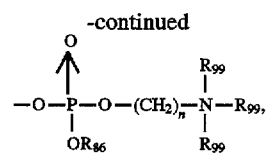

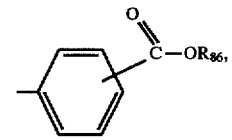

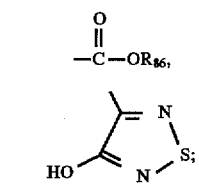

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

Another aspect of this invention is a method for treating septic shock in humans which comprises administering to a human a therapeutically effective dose of 1H-indole-3-acetamide and pharmaceutically acceptable salts thereof. A preferred method for treating septic shock is to administer to humans either (1) a 1H-indole-3-acetamide substituted at the 4 and/or 5 position and substituted at the 1 position with a benzyl or biphenyl group (or a pharmaceutically acceptable salts thereof); or (2) a 1H-indole-3-acetamide substituted at the 4 and/or 5 position and substituted at the 2 position with a halogen, oxygen, nitrogen or sulfur group; or (3) a 1H-indole-3-acetamide substituted at the 4 and/or 5 position and is substituted at the 2 position with an alkyl group of 1 to 3 carbon atoms. When the 1H-indole-3-acetamide nucleus is substituted at the 4 positions the preferred groups are selected from the group:

—O—CH$_2$—R$_{98}$,

—S—CH$_2$—R$_{98}$,

—NH—CH$_2$—R$_{98}$ and

—CH$_2$—CH$_2$—R$_{98}$;

where acidic group R98 is selected from;

—CO$_3$H

—SO$_3$H

—P(O)(OH)$_2$ or salts, and ester derivatives of such acidic groups.

When the 1H-indole-3-acetamide nucleus is substituted at the 5 positions the preferred groups are selected from the group:

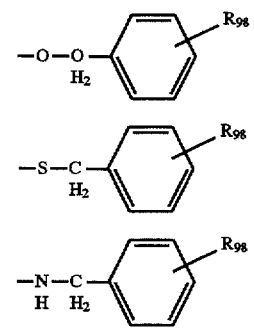

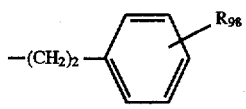

$$-O-(CH_2)_{2-4}-R_{98}$$

$$-S-(CH_2)_{2-4}-R_{98}$$

$$-NH-(CH_2)_{2-4}-R_{98}$$

$$-CH_2-(CH_2)_{2-4}-R_{98}$$

where acidic group $R_{98}$ is selected from;
—$CO_2H$
—$SO_3H$
—$P(O)(OH)_2$
or salts, and ester derivatives of such acidic groups.

Pharmaceutical Formulations

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

The compound can be administered by a variety of routes including oral, aerosol, rectal, transdermal, subcutaneous, intravenous, intramuscular, and intranasal. Pharmaceutical formulations of the invention are prepared by combining (e.g., mixing) a therapeutically effective amount of the 1H-indole-3-acetamides of the invention together with a pharmaceutically acceptable carrier or diluent therefor. The compounds of the present invention are preferably formulated prior to administration.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

The following formulation examples are illustrative only and are not intended to limit the scope of the invention in any way. The term, "Active Ingredient", means a 1H-indole-3-acetamide compound of the invention or a pharmaceutically acceptable salt thereof.

Formulation 1

A tablet is prepared using the ingredients below:

|  | Quantity - (mg/capsule) |
|---|---|
| Active ingredient | 250 |
| Cellulose, microcrystalling | 400 |
| Silicon dioxide, fumed | 10 |
| Stearic acid | 5 |

The components are blended and compressed to form tablets. each weighing 665 mg.

Formulation 2

An aerosol solution is prepared containing the following components:

|  | Weight |
|---|---|
| Active Ingredient | 0.25 |
| Ethanol | 25.75 |
| Chlorodifluoromethane propellant | 74.00 |

The Active Ingredient is mixed with ethanol and the mixture added to a portion of the propellant, cooled to −30° C. and transferred to a filling device. The required amount is then fed to a stainless steel container and diluted with the remainder of the propellant. The valve units are then fitted to the container.

Assay Experiments

Assay Example 1

The following chromogenic assay procedure was used to identify and evaluate inhibitors of recombinant human secreted phospholipase A$_2$. The assay described herein has been adapted for high volume screening using 96 well microtiter plates. A general description of this assay method is found in the article, "Analysis of Human Synovial Fluid Phospholipase A$_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992: Reagents:

REACTION BUFFER
  CaCl2.2H2O (1.47 g/L)
  KCl (7.455 g/L)
  Bovine Serum Albumin (fatty acid free) (1 g/L) (Sigma A-7030, product of Sigma Chemical Co. St. Louis Mo., U.S.A.)
  TRIS HCl (3.94 g/L)
  pH 7.5 (adjust with NaOH)
ENZYME BUFFER
  0.05 NaOAc.3H2O, pH 4.5
  0.2 NaCl
  Adjust pH to 4.5 with acetic acid
DTNB—5,5"-dithiobis-2-nitrobenzoic acid
RACEMIC DIHEPTANOYL THIO—PC racemic 1,2-bis(heptanoylthio)-1,2-dideoxy-sn-glycero-3-phosphorylcholine TRITON X-100™ prepare at 6.249 mg/ml in reaction buffer to equal 10 uM.

REACTION MIXTURE

A measured volume of racetic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;
2. Add 10 ul test compound (or solvent blank) to appropriate wells, mix 20 seconds:
3. Add 50 nanograms of sPLA$_2$ (10 microliters) to appropriate wells;
4. incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition. Each IC$_{50}$ value was determined three times.

Results of Human Secreted Phospholipase A2 Inhibition Tests--Amides

| Example | Inhibition of human secreted PLA$_2$ IC50 ± mean deviation (3–5 tests) |
| --- | --- |
| 1 | 1.33 ± 0.45 uM |
| 2 | 0.84 ± 0.38 uM |
| 3 | 3.70 ± 2.82 uM |
| 4 | 2.05 ± 0.85 uM |
| 5 | 0.84 ± 0.17 uM |
| 6 | 1.30 ± 0.29 uM |
| 7 | 5.45 ± 1.62 uM |
| 8 | 21.39 ± 8.55 uM |
| 9 | 0.26 ± 0.11 uM |
| 10 | 38.08 ± 2.82 uM |
| 11 | 0.25 ± 0.03 uM |
| 12 | 0.40 ± 0.09 uM |
| 13 | 0.92 ± 0.24 uM |
| 14 | 8.48 ± 5.25 uM |
| 15 | 1.51 ± 0.58 uM |
| 16 | 1.84 ± 0.44 uM |
| 17 | 1.61 ± 0.44 uM |
| 18 | 0.80 ± 0.05 uM |
| 19 | 1.16 ± 0.41 uM |
| 20 | 1.05 ± 0.11 uM |
| 21 | 0.43 ± 0.23 uM |
| 22 | 0.15 ± 0.04 uM |
| 23 | 0.92 ± 0.36 uM |
| 24 | 0.06 ± 0.02 uM |
| 25 | 3.34 ± 0.46 uM |
| 26 | 2.49 uM |
| 27 | 3.30 ± 0.10 uM |
| 28 | 1.55 ± 0.93 uM |
| 29 | 1.23 ± 0.33 um |
| 30 | 3.61 ± 0.75 uM |
| 31 | 0.45 ± 0.08 uM |
| 32 | 12.21 ± 0.55 uM |
| 33 | 0.30 ± 0.12 uM |
| 34 | 7.96 ± 1.22 uM |
| 35 | 2.36 ± 0.15 uM |
| 36 | 7.46 ± 1.66 uM |
| 37 | 9.44 ± 1.44 uM |
| 38 | 0.40 ± 0.07 uM |
| 39 | 1.38 ± 0.28 uM |
| 40 | 0.05 ± 0.01 uM |
| 41 | 0.06 ± 0.01 uM |
| 42 | 0.23 ± 0.06 uM |
| 43 | 0.07 ± 0.03 uM |
| 44 | 0.38 ± 0.14 aM |
| 45 | 1.55 ± 0.51 uM |
| 46 | 0.16 ± 0.19 uM |
| 47 | 0.09 ± 0.06 uM |
| 48 | >100 uM |
| 49 | 0.47 ± 0.05 uM |
| 50 | 2.47 ± 1.31 uM |
| 51 | 8.28 ± 4.33 uM |
| 52 | 0.77 ± 0.27 uM |
| 53 | 0.68 ± 0.00 uM |
| 54 | 0.65 ± 0.15 uM |
| 55 | 22.0 ± 6.0 uM |
| 56 | 0.34 ± 0.10 uM |
| 57 | 1.27 uM |
| 58 | 0.05 ± 0.00 uM |
| 59 | 0.074 ± 0.o16 uM |
| 60 | 0.104 ± 0.017 uM |
| 61 | 0.27 uM |
| 62 | 0.02 ± 0.01 uM |
| 63 | 0.039 ± 0.005 uM |
| 64 | 0.016 ± 0.001 uM |
| 65 | 0.36 ± 0.13 uM |
| 66 | 0.36 ± 0.07 uM |
| 67 | 1.68 uM |
| 68 | 1.45 uM; 1.12 uM |
| 69 | 1.38 ± 0.52 uM |
| 70 | 5.88 ± 1.17 uM |
| 71 | 2.37 ± 0.79 uM |
| 72 | 0.050 ± 0.15 uM |
| 73 | 0.010 ± 0.001 uM |
| 74 | 0.024 ± 0.002 uM |
| 75 | 0.039 ± 0.004 uM |
| 76 | 0.337 uM; 0.305 uM |
| 77 | 0.336 ± 0.023 uM |
| 78 | 0.118 ± 0.011 uM |
| 79 | 0.046 ± 0.006 uM |
| 80 | 0.20 ± 0.09 uM |
| 81 | 3.8 uM; 3.6 uM |
| 82 | 3.68 ± 0.19 uM |
| 83 | 0.15 ± 0.04 uM |
| 84 | 0.195 ± 0.065 uM |
| 85 | 0.050 ± 0.019 uM |
| 86 | 0.42 ± 0.21 uM |
| 87 | 0.072 ± 0.017 uM |
| 88 | 0.03 ± 0.006 uM |
| 89 | 0.12 ± 0.02 uM |
| 90 | 0.09 ± 0.01 uM |
| 91 | 0.02 ± 0.01 uM |
| 92 | 0.014 ± 0.004 uM |

-continued

Results of Human Secreted Phospholipase A2 Inhibition Tests—Amides

| Example | Inhibition of human secreted PLA$_2$ IC50 ± mean deviation (3–5 tests) |
|---|---|
| 93 | 0.14 ± 0.04 uM |
| 94 | 0.612 ± 0.065 uM |
| 95 | 1.01 ± 0.32 uM |
| 96 | 0.62 ± 0.18 uM |
| 97 | 0.15 ± 0.01 uM |
| 98 | 1.15 ± 0.32 uM |
| 99 | 0.54 ± 0.18 uM |
| 100 | 3.84 ± 1.32 uM |
| 101 | 1.89 ± 0.50 uM |

Assay Example 2

Method:

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer (Model FTO3C, product of Grass Medical Instruments Co., Quincy, Mass., U.S.A.). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative concentration-response curves:

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration (sPLA$_2$) in the tissue bath by half-log$_{10}$ increments while the previous concentration remained in contact with the tissues (Ref. 1, supra.) Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the efects of various drugs on the contractile efects of sPLA$_2$, the compounds and their respective vehicles were added to the tissues 30 min. prior to starting the sPLA$_2$ concentration-response curves.

Statistical analysis:

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref. 2). The model includes four parameters: the maximum tissue response which was assumed the same for each curve, the ED$_{50}$ for the control curve, the steepness of the curves, and the pA$_2$, the concentration of antagonist chat requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA2 may be interpreted as the apparent K$_B$, the dissociation constant of the inhibitor.

To estimate the drug-induced suppression of the maximal responses, sPLA$_2$ responses (10 ug/ml) were determined in the absence and presence of drug, and percent suppression was calculated for each pair of tissues. Representative examples of inhibitory activities are presented in Table 2, below.

Ref. 1—van, J. M.: Cumulative dose-response curves. II. Technique for the making of dose-response curves in isolated organs and the evaluation of drug parameters. Arch. Int. Pharmacodyn. Ther. 143: 299–330, 1963.

Ref. 2—Waud, D.: Analysis of dose-response relationships. in *Advance in General and Cellular Pharmacology* eds Narahashi, Bianchi 1:145–178, 1976.

TABLE 2

| Compound of Example No. | Tissue Test (sPLA$_2$) | |
|---|---|---|
|  | Apparent K$_B$ (uM) | % Supp (30 uM)$^3$ (10 uM*)$^4$ |
| 4 | 22.54 ± 3.91 | 10.5 ± 23.1 |
| 5 | 3.43 ± 0.88 | 74.9 ± 4.2 |
| 9 | 5.91 ± 0.97 | 49.2 ± 9.4 |
| 12 | 7.93 ± 3.52 | 30.3 ± 15.2 |
| 16 | 4.92 ± 0.60 | 51.7 ± 4.2 |
| 18 | 1.98 ± 0.35 | 74.1 ± 4.0 |
| 23 | 2.38 ± 0.59 | 83.3 ± 2.7 |

Notes:
$^3$% suppression of sPLA$_2$ contraction at compound concentration of 30 uM.
% suppression of sPLA$_2$ contraction at compound concentration of 10 uM.

While the present invention has been illustrated above by certain specific embodiments, it is not intended that these specific examples should limit the scope of the invention as described in the appended claims.

We claim:

1. A 1H-indole-3-acetamide compound represented by the formula (III), or a pharmaceutically acceptable salt or prodrug derivative thereof;

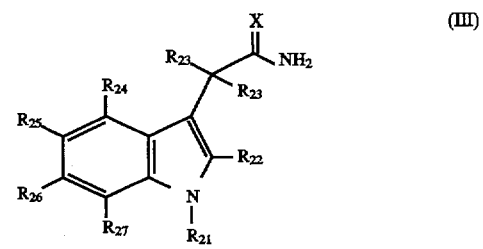

wherein;

X is oxygen;

R$_{21}$ is —(CH$_2$)$_n$—(R$_{80}$), or —(NH)—(R$_{80}$), where n is 1 to 8, and R$_{80}$ is aryl or aryl substituted by C$_1$–C$_{10}$ alkyl, $C_2$–$C_{10}$ alkenyl, $C_2$–$C_{10}$ alkynyl, $C_1$–$C_{10}$ haloalkyl, $C_4$–$C_{12}$ cycloalkyl, $C_1$–$C_{10}$ hydroxyalkyl, carboxyl, halo, —CN, —CHO, —OH, —SH, $C_1$–$C_{10}$ alkylthio, $C_1$–$C_{10}$ alkoxyl, carboxyl, amino, or hydroxyamino, or a substituted or unsubstituted 5 to 8 membered heterocyclic ring;

$R_{22}$ is hydrogen, halo, $C_1$–$C_3$ alkyl, ethenyl, cyclopropyl, $C_1$–$C_2$ alkylthio, $C_1$–$C_2$ alkoxy, —CHO, —CN;

each $R_{23}$ is independently hydrogen, halo, or methyl;

$R_{24}$ and $R_{25}$ are each independently selected from (a) and (b) where;
(a) is hydrogen, halo, alkyl, or alkoxy, and;
(b) is a group having the formula;

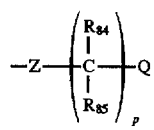

with the proviso that at least one of $R_{24}$ and $R_{25}$ must be selected from (b), and where;

$R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON($R_{82}R_{83}$), -5-tetrazolyl, —SO$_3$H,

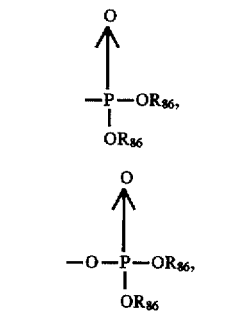

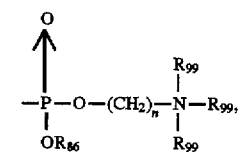

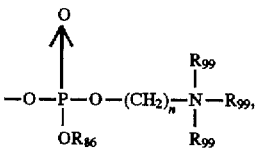

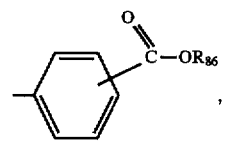

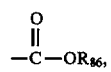

-continued

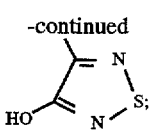

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl;

$R_{26}$, and $R_{27}$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or the adjacent hydrocarbyl groups in the groups $R_{26}$ and $R_{27}$ combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkylthio, arylthio, thioacetal, —C(O)O($C_1$–$C_{10}$ alkyl), hydrazide, hydrazino, hydrazido, —NH$_2$, —NO$_2$, —NR$_{82}R_{83}$, and —C(O)NR$_{82}R_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

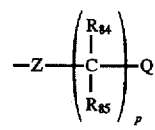

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON($R_{82}R_{83}$), -5-tetrazolyl, —SO$_3$H,

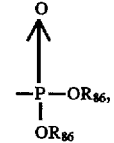

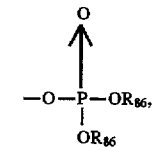

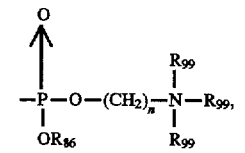

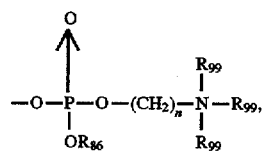

105

-continued

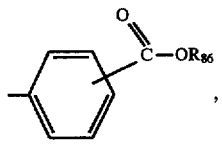

,

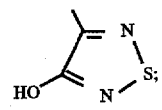

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

2. A pharmaceutical formulation comprising a compound as claimed in claim 1 together with a pharmaceutically acceptable carrier or diluent therefor.

3. A method of inhibiting sPLA$_2$ mediated release of fatty acid which comprises contacting sPLA$_2$ with a therapeutically effective amount of 1H-indole-3-acetamide compound as claimed in claim 1.

4. A 1H-indole-3-acetamide compound represented by the formula (IV), or a pharmaceutically acceptable salt or prodrug derivative thereof;

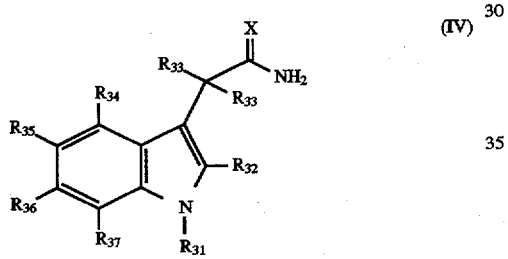 (IV)

wherein;

X is oxygen;

$R_{31}$ is selected from groups (i), (ii) and (iii) where;

(i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or (ii) is aryl or aryl substituted by halo, —CN, —CHO, —OH, —SH, $C_1$–$C_{10}$ alkylthio, $C_1$–$C_{10}$ alkoxyl, carboxyl, amino, or hydroxyamino;

(iii) is

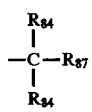

where $R_{84}$ is hydrogen or $C_1$–$C_{10}$ alkyl, and $R_{87}$ is selected from the group; phenyl, naphthyl, indenyl, and biphenyl, unsubstituted or substituted by halo, —CN, —CHO, —OH, —SH, $C_1$–$C_{10}$ alkylthio, $C_1$–$C_{10}$ alkoxy, carboxyl, amino, hydroxyamino; or a substituted or unsubstituted 5 to 8 membered heterocyclic ring;

$R_{32}$ is halo, $C_1$–$C_2$ alkylthio, $C_1$–$C_2$ alkoxy;

each $R_{33}$ is independently hydrogen, halo, or methyl;

$R_{34}$ and $R_{35}$ are each independently selected from (a) and (b) where;

(a) is hydrogen, halo, alkyl, or alkoxy, and

106

(b) is a group having the formula;

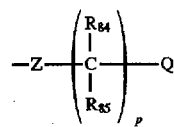

with the proviso that at least one of $R_{34}$ and $R_{35}$ must be selected from (b), and where;

$R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON($R_{82}R_{83}$), -5-tetrazolyl, —SO$_3$H,

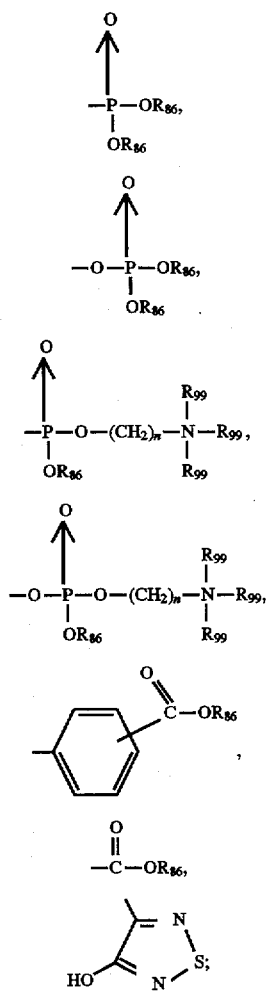

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl, $R_{36}$ and $R_{37}$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, or the adjacent hydrocarbyl groups in the groups $R_{36}$ and $R_{37}$ combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkylthio, arylthio, thioacetal, —C(O)O($C_1$–$C_{10}$ alkyl), hydrazide, hydrazino, hydrazido, —$NH_2$, —$NO_2$, —$NR_{82}R_{83}$, and —C(O)$NR_{82}R_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

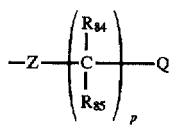

where,
$R_{84}$ and $R_{85}$ are each independently selected from hydrogen, $C_1$–$C_{10}$ alkyl, hydroxy, or $R_{84}$ and $R_{85}$ taken together are =O;
p is 1 to 5,
Z is a bond, —O—, —N($C_1$–$C_{10}$ alkyl)—, —NH—, or —S—; and
Q is —CON($R_{82}R_{83}$), -5-tetrazolyl, —$SO_3H$,

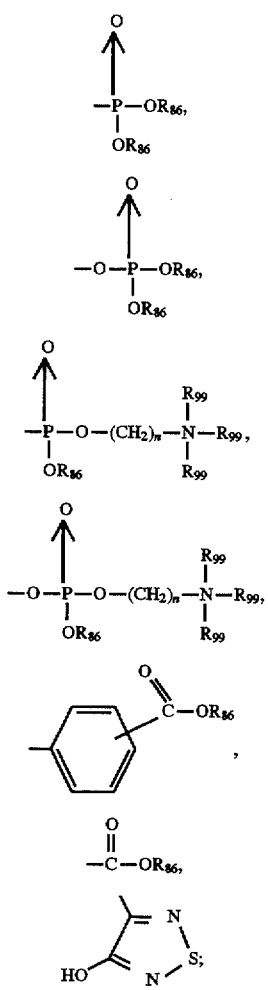

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

5. A pharmaceutical formulation comprising a compound as claimed in claim 4 together with a pharmaceutically acceptable carrier or diluent therefor.

6. A method of inhibiting $sPLA_2$ mediated release of fatty acid which comprises contacting $sPLA_2$ with a therapeutically effective amount of 1H-indole-3-acetamide compound as claimed in claim 4.

7. A 1H-indole-3-acetamide compound represented by the formula (V), or a pharmaceutically acceptable salt or prodrug derivative thereof;

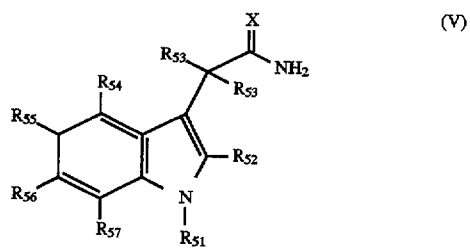

wherein;
X is oxygen;
$R_{51}$ is

where,
$R_{84}$ is hydrogen or $C_1$–$C_{10}$ alkyl, and $R_{87}$ is —$(CH_2)_m$-(phenyl) or —$(CH_2)_m$-(biphenyl), wherein m is 0 to 2 and the phenyl or biphenyl radicals are unsubstituted or substituted by halo, —CN, —CHO, —OH, nitro, phenyl, —SH, $C_1$–$C_{10}$ alkylthio, $C_1$–$C_{10}$ alkyl, $C_1$–$C_{10}$ alkoxyl, carboxyl, amino, hydroxyamino or a substituted or unsubstituted 5 to 8 membered heterocyclic ring;

$R_{52}$ is halo, methylthio, cyclopropyl, or $C_1$–$C_3$ alkyl;
each $R_{53}$ is hydrogen or halo;
$R_{54}$ and $R_{55}$ are each independently selected from (a) and (b) where;
(a) is hydrogen, and;
(b) is a group having the formula;

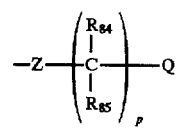

with the proviso that at least one of $R_{54}$ and $R_{55}$ must be selected from (b), and where;

$R_{84}$ and $R_{85}$ are each independently selected from hydrogen, $C_1$–$C_{10}$ alkyl, hydroxy, or $R_{84}$ and $R_{85}$ taken together are =O;
p is 1 to 5,
Z is a bond, —O—, —N($C_1$–$C_{10}$ alkyl)—, —NH— or —S—; and
Q is -5-tetrazolyl, —$SO_3H$,

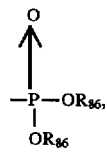

-continued

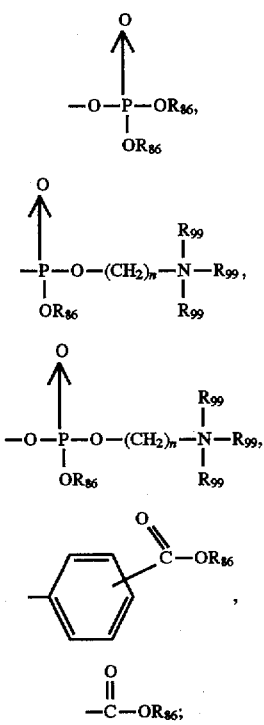

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl;

$R_{56}$, and $R_{57}$ are each independently hydrogen, $C_1$–$C_{10}$ alkyl, aryl, aralkyl, $C_1$–$C_{10}$ haloalkyl, $C_1$–$C_{10}$ alkoxy, $C_1$–$C_{10}$ haloalkoxy, phenoxy, halo, hydroxy, carboxyl, or a group having the formula;

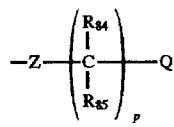

where,
$R_{84}$ and $R_{85}$ are each independently selected from hydrogen, $C_1$–$C_{10}$ alkyl, hydroxy, or $R_{84}$ and $R_{85}$ taken together are =O;
p is 1 to 5,
Z is a bond, —O—, —N($C_1$–$C_{10}$ alkyl)—, —NH—, or —S—; and
Q is -5-tetrazolyl, —SO$_3$H,

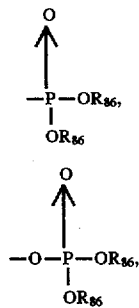

-continued

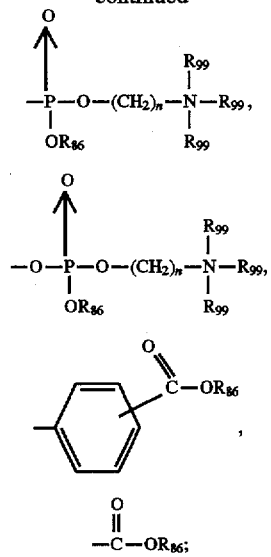

where n is 1 to 8, $R_{86}$ is hydrogen a metal, or $C_1$–$C_{10}$ alkyl, and $R_{99}$ is selected from hydrogen or $C_1$–$C_{10}$ alkyl.

8. A pharmaceutical formulation comprising a compound as claimed in claim 4 together with a pharmaceutically acceptable carrier or diluent therefor.

9. A method of inhibiting sPLA$_2$ mediated release of fatty acid which comprises contacting sPLA$_2$ with a therapeutically effective amount of 1H-indole-3-acetamide compound as claimed in claim 7.

10. A method of treating septic shock in humans which comprises administering to a human a therapeutically effective dose of a 1H-indole-3-acetamide compound of claim 7.

11. The method of claim 10 wherein the 1H-indole-3-acetamide compound is substituted with an acidic group at the 4 or 5 position; with the proviso that when the 1H-indole-3-acetamide compound nucleus is substituted at the 4 position the acidic group is selected from the group:

—O—CH$_2$—R$_{98}$,
—S—CH$_2$—R$_{98}$,
—NH—CH$_2$—R$_{98}$ and
—CH$_2$—CH$_2$—R$_{98}$;

and when the 1H-indole-3-acetamide compound nucleus is substituted at the 5 position the acidic group is selected from the group:

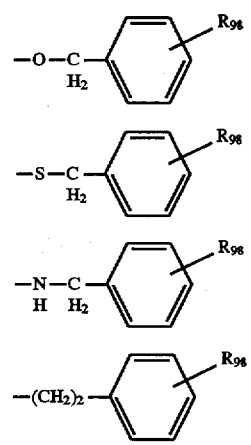

-continued $$-O-(CH_2)_{2-4}-R_{98}$$

$$-S-(CH_2)_{2-4}-R_{98}$$

$$-NH-(CH_2)_{2-4}-R_{98}$$

$$-CH_2-(CH_2)_{2-4}-R_{98}$$

where acidic group $R_{98}$ is selected from;
—$CO_2H$
—$SO_3H$
—$P(O)(OH)_2$ or salts, and ester derivatives of such acidic groups.

12. A compound selected from the following group and pharmaceutically acceptable salts and prodrug derivatives thereof:

(A) 4-((3-(2-Amino-2-oxoethyl)-2-chloro-1-(phenylmethyl)-1H-indole-5-yl)oxy)butanoic acid, (B) 2-((3-(2-Amino-2-oxoethyl)-2-methyl-1-(phenylmethyl)-1H-indol-4-yl)oxy)acetic acid, (C) (3-((3-(2-amino-2-oxoethyl)-2-methyl-1-(phenylmethyl)-1H-indol-5-yl)oxy)propyl)phosphonic acid, (D) 4-((3-(2-Amino-2-oxoethyl)-2-bromo-1-(phenylmethyl)-1H-indol-5-yl)oxy)butanoic acid, (E) 4-((3-(2-Amino-2-oxoethyl)-2-(methylthio)-1-(phenylmethyl)-1H-indol-5-yl)oxy)butanoic acid, (G) 4-((3-(2-amino-2-oxoethyl)-2-ethyl-1-(phenylmethyl)-1-H-indol-5-yl)oxy)butanoic acid, (I) (3-((3-(2-amino-2-oxoethyl)-2-ethyl-1-(phenylmethyl)-1H-indol-5-yl)oxy)propyl)phosphonic acid, (J) (3-((3-(2-Amino-2-oxoethyl)-2-ethyl-1-(phenylmethyl)-1H-indol-5-yl)oxy)propyl)phosphonic acid monomethyl ester, (K) (3-((3-(2-Amino-2-oxoethyl)-1-((3-chlorophenyl)methyl)-2-ethyl-1H-indol-5-yl)oxy)propyl)phosphonic acid, (L) ((3-(2-Amino-2-oxoethyl)-1-((3-chlorophenyl)methyl)-2-(methyl-1H-indol-4-yl)oxy)methyl)acetic acid sodium salt, (M) ((3-(2-Amino-2-oxoethyl)-1-((1,1'-biphenyl)-2-ylmethyl)-2-methyl-1H-indol-4-yl)oxy)acetic acid sodium salt, (N) ((3-(2-Amino-2-oxoethyl)-2-ethyl-1-(phenylmethyl)-1H-indol-4-yl)oxy)acetic acid, (O) 2-((3-(2-Amino-2-oxoethyl)-1-((3-chlorophenyl)methyl)-2-ethyl-1H-indol-4-yl)oxy)acetic acid, (Q) (3-((3-(2-Amino-2-oxoethyl)-2-cyclopropyl-1-(phenylmethyl)-1H-indol-5-yl)oxy)propyl)phosphonic acid, (R) (3-((3-(2-Amino-2-oxoethyl)-1-(phenylmethyl)-1H-indol-5-yl)oxy)propyl)phosphonic acid, (S) 4-((3-(2-Amino-2-oxoethyl)-1-(phenylmethyl)-1H-indol-5-yl)oxy)butanoic acid, (T) 3-(4-((3-(2-Amino-2-oxoethyl)-2-ethyl-1-(phenylmethyl)-1H-indol-5-yl)oxy)propane)sulfonic acid, (U) 3-((3-(2-Amino-2-oxoethyl)-2-bromo-1-(phenylmethyl)-(1H-indol-5-yl)oxy)propyl)phosphonic acid monomethyl ester, (X) 4-((3-(2-Amino-2-oxoethyl)-2-bromo-6-chloro-1-(phenylmethyl)-1H-indol-5-yl)oxy)butanoic acid, and (Y) 3-(4-((3-(2-Amino-2-oxoethyl)-6-chloro-1-(phenylmethyl)-1H-indol-5-yl)oxy)propyl)phosphonic acid.

13. A pharmaceutical formulation comprising a compound as claimed in claim 12 together with a pharmaceutically acceptable carrier or diluent therefor.

14. A method of inhibiting sPLA$_2$ mediated release of fatty acid which comprises contacting sPLA$_2$ with an therapeutically effective amount of a 1H-indole-3-acetamide wherein said acetamide is substituted at the 4 and/or 5 position with an acidic group, and is substituted at the 1 position with a benzyl or substituted benzyl group and pharmaceutically acceptable salts thereof.

15. A method of inhibiting sPLA$_2$ mediated release of fatty acid which comprises contacting sPLA$_2$ with a therapeutically effective amount of a 1H-indole-3-acetamide, and pharmaceutically acceptable salts thereof, wherein said acetamide is substituted at the 4 and/or 5 position with an acidic group, and is substituted at the 2 position with a group of up to about 3 carbon atom size or equivalent containing halogen, oxygen, nitrogen or sulfur.

16. A method of inhibiting sPLA$_2$ mediated release of fatty acid which comprises contacting sPLA$_2$ with an therapeutically effective amount of a 1H-indole-3-acetamide compound represented by the formula (VI) or a pharmaceutically acceptable salt or prodrug derivative thereof:

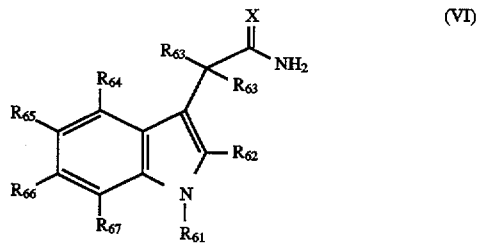

(VI)

wherein
X is oxygen;
$R_{61}$ is selected from groups (i), (ii) and (iii) where;
(i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or
(ii) is aryl or aryl substituted by halo, —CN, —CHO, —OH, —SH, $C_1$–$C_{10}$ alkylthio, $C_1$–$C_{10}$ alkoxylthio, carboxyl, amino, or hydroxyamino;
(iii) is

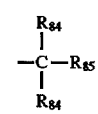

where $R_{84}$ is hydrogen or $C_1$–$C_{10}$ alkyl, and $R_{85}$ is selected from the group; phenyl, naphthyl, indenyl, and biphenyl, unsubstituted or substituted by halo, —CN, —CHO, —OH, nitro, phenyl, —SH, $C_1$–$C_{10}$ alkylthio, $C_1$–$C_{10}$ alkoxyl, amino, hydroxyamino; or a substituted or unsubstituted 5 to 8 membered heterocyclic ring, or $R_{84}$ and $R_{85}$ taken together are =O;

$R_{62}$ is hydrogen, halo, $C_1$–$C_3$ alkyl, ethenyl, cyclopropyl, $C_1$–$C_2$ alkylthio, $C_1$–$C_2$ alkoxy, —CHO, —CN;

each $R_{63}$ is independently hydrogen, or halo;

$R_{64}$, $R_{65}$, $R_{66}$, and $R_{67}$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, or any two adjacent hydrocarbyl groups in the set $R_{64}$, $R_{65}$, $R_{66}$, and $R_{67}$, combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazide, hydrazino, hydrazido, —NH$_2$, —NO$_2$, —NR$_{82}$R$_{83}$, and —C(O)NR$_{82}$R$_{83}$, where, R$_{82}$ and R$_{83}$ are independently hydrogen, C$_1$–C$_{10}$ alkyl, C$_1$–C$_{10}$ hydroxyalkyl, or taken together with N, R$_{82}$ and R$_{83}$ form a 5 to 8 membered heterocyclic ring; or a group having the formula;

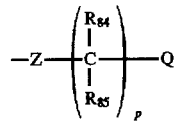

where,
R$_{84}$ and R$_{85}$ are each independently selected from hydrogen, C$_1$–C$_{10}$ alkyl, hydroxy, or R$_{84}$ and R$_{85}$ taken together are =O;
p is 1 to 5,
Z is a bond, —O—, —N(C$_1$–C$_{10}$ alkyl)—, —NH—, or —S—; and
Q is —CON(R$_{82}$R$_{83}$), -5-tetrazolyl, —SO$_3$H,

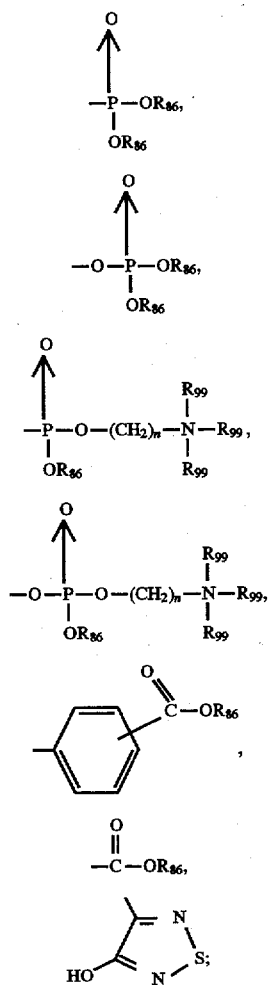

where n is 1 to 8, R$_{86}$ is independently selected from hydrogen, a metal, or C$_1$–C$_{10}$ alkyl, and R$_{99}$ is selected from hydrogen or C$_1$–C$_{10}$ alkyl.

17. A method of inhibiting sPLA$_2$ mediated release of fatty acid which comprises contacting sPLA$_2$ with a therapeutically effective amount of 1H-indole-3-acetamide compound represented by the formula (I), or a pharmaceutically acceptable salt or prodrug derivative thereof;

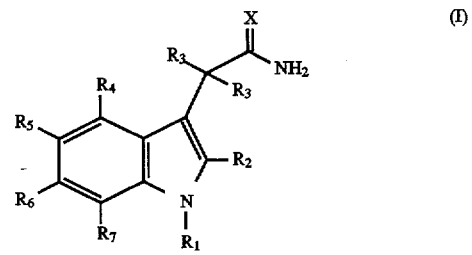

wherein;
X is oxygen;
R$_1$ is selected from groups (i), (ii) and (iii) where;
  (i) is C$_6$–C$_{20}$ alkyl, C$_6$–C$_{20}$ alkenyl, C$_6$–C$_{20}$ alkynyl, C$_6$–C$_{20}$ haloalkyl, C$_4$–C$_{12}$ cycloalkyl, or
  (ii) is selected from the group; phenyl, naphthyl, indenyl, and biphenyl, unsubstituted or substituted by halo, —CN, —CHO, —OH, nitro, —SH, C$_1$–C$_{10}$ alkylthio, C$_1$–C$_{10}$ alkoxyl, C$_1$–C$_{10}$ alkyl, carboxyl, amino, or hydroxyamino; or
  (iii) is —(CH$_2$)$_n$—(R$_{80}$), or —(NH)—(R$_{81}$), where n is 1 to 8, and R$_{80}$ is a group recited in (i), and R$_{81}$ is selected from a group recited in (i) or (ii);
R$_2$ is hydrogen, halo, C$_1$–C$_3$ alkyl, ethenyl, cyclopropyl, C$_1$–C$_2$ alkylthio, C$_1$–C$_2$ alkoxy, —CHO, or —CN;
each R$_3$ is independently hydrogen, halo, or methyl;
R$_4$, R$_5$, R$_6$, and R$_7$ are each independently hydrogen, C$_1$–C$_{10}$ alkyl, C$_1$–C$_{10}$ alkenyl, C$_1$–C$_{10}$ alkynyl, C$_3$–C$_8$ cycloalkyl, aryl, aralkyl, or any two adjacent hydrocarbyl groups in the set R$_4$, R$_5$, R$_6$, and R$_7$, combine with the ring carbon atoms to which they are attached to form a 5 or 6 membered substituted or unsubstituted carbocyclic ring; or C$_1$–C$_{10}$ haloalkyl, C$_1$–C$_{10}$ alkoxy, C$_1$–C$_{10}$ haloalkoxy, C$_4$–C$_8$ cycloalkoxy, phenoxy, halo, hydroxy, carboxyl, —SH, —CN, C$_1$–C$_{10}$ alkyl thio, arylthio, thioacetal, —C(O)O(C$_1$–C$_{10}$ alkyl), hydrazide, hydrazino, hydrazido, —NH$_2$, —NO$_2$, —NR$_{82}$R$_{83}$, and —C(O)NR$_{82}$R$_{83}$, where, R$_{82}$ and R$_{83}$ are independently hydrogen, C$_1$–C$_{10}$ alkyl, C$_1$–C$_{10}$ hydroxyalkyl, or taken together with N, R$_{82}$ and R$_{83}$ form a 5 to 8 membered heterocyclic ring; or a group having the formula;

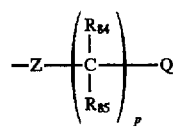

where,
R$_{84}$ and R$_{85}$ are each independently selected from hydrogen, C$_1$–C$_{10}$ alkyl, hydroxy, or R$_{84}$ and R$_{85}$ taken together are =O;
p is 1 to 5,
Z is a bond, —O—, —N(C$_1$–C$_{10}$ alkyl)—, —NH—, or —S—; and
Q is —CON(R$_{82}$R$_{83}$), -5-tetrazolyl, —SO$_3$H,

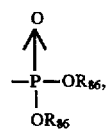

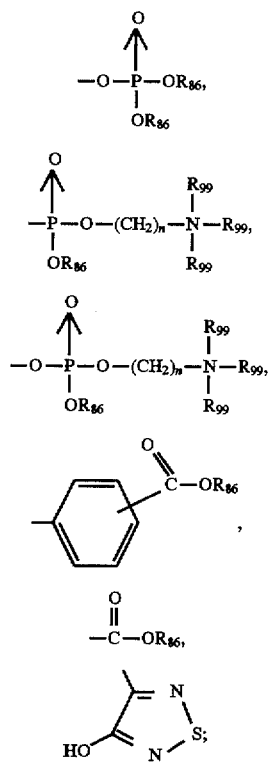

where n is 1 to 8, $R_{86}$ is independently selected from hydrogen, a metal, or $C_1$-$C_{10}$ alkyl, and $R_{99}$ is selected from hydrogen or $C_1$-$C_{10}$ alkyl.

18. A method of inhibiting sPLA$_2$ mediated release of fatty acid which comprises contacting sPLA$_2$ with a therapeutically effective amount of 1H-indole-3-acetamide compound represented by the formula (II), or a pharmaceutically acceptable salt or prodrug derivative thereof;

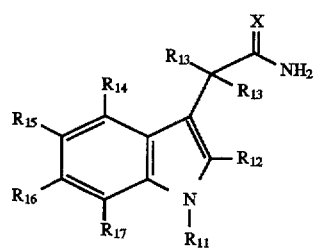

wherein;

X is oxygen;

$R_{11}$ is selected from groups (i), (ii) (iii) and (iv) where;
(i) is $C_6$-$C_{20}$ alkyl, $C_6$-$C_{20}$ alkenyl, $C_6$-$C_{20}$ alkynyl, $C_6$-$C_{20}$ haloalkyl, $C_4$-$C_{12}$ cycloalkyl, or
(ii) is aryl or aryl substituted by halo, nitro, —CN, —CHO, —OH, —SH, $C_1$-$C_{10}$ alkyl, $C_1$-$C_{10}$ alkylthio, $C_1$-$C_{10}$ alkoxyl, carboxyl, amino, or hydroxyamino; or
(iii) is —(CH$_2$)$_n$—(R$_{80}$), or —(NH)—(R$_{81}$), where n is 1 to 8, and $R_{80}$ is a group recited in (i), and $R_{81}$ is selected from a group recited in (i) or (ii);

(iv) is

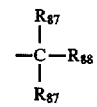

where $R_{87}$ is hydrogen or $C_1$-$C_{10}$ alkyl, and $R_{88}$ is selected from the group; phenyl, naphthyl, indenyl, and biphenyl, unsubstituted or substituted by halo, —CN, —CHO, —OH, —SH, $C_1$-$C_{10}$ alkylthio, $C_1$-$C_{10}$ alkoxyl, phenyl, nitro, $C_1$-$C_{10}$ alkyl, $C_1$-$C_{10}$ haloalkyl, carboxyl, amino, hydroxyamino; or a substituted or unsubstituted 5 to 8 membered heterocyclic ring;

$R_{12}$ is halo, $C_1$-$C_2$ alkylthio, or $C_1$-$C_2$ alkoxy;

each $R_{13}$ is independently hydrogen, halo, or methyl;

$R_{14}$, $R_{15}$, $R_{16}$, and $R_{17}$ are each independently hydrogen, $C_1$-$C_{10}$ alkyl, $C_1$-$C_{10}$ alkenyl, $C_1$-$C_{10}$ alkynyl, $C_3$-$C_8$ cycloalkyl, aryl, aralkyl, or any two adjacent hydrocarbyl groups in the set $R_{14}$, $R_{15}$, $R_{16}$, and $R_{17}$, combine with the ring carbon atoms to which they are attached to form a 5 or 6 membered substituted or unsubstituted carbocyclic ring; or $C_1$-$C_{10}$ haloalkyl, $C_1$-$C_{10}$ alkoxy, $C_1$-$C_{10}$ haloalkoxy, $C_4$-$C_8$ cycloalkoxy, phenoxy, halo, hydroxy, carboxyl, —SH, —CN, $C_1$-$C_{10}$ alkylthio, arylthio, thioacetal, —C(O)O(C$_1$-$C_{10}$ alkyl), hydrazide, hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$-$C_{10}$ alkyl, $C_1$-$C_{10}$ hydroxyalkyl, or taken together with N, $R_{82}$ and $R_{83}$ form a 5 to 8 membered heterocyclic ring; or a group having the formula;

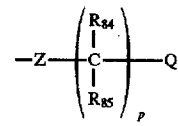

where, $R_{84}$ and $R_{85}$ are each independently selected from hydrogen, $C_1$-$C_{10}$ alkyl, hydroxy, or $R_{84}$ and $R_{85}$ taken together are =O;

p is 1 to 5,

Z is a bond, —O—, —N(C$_1$-$C_{10}$ alkyl)—, —NH—, or —S—; and

Q is —CON(R$_{82}$R$_{83}$), -5-tetrazolyl, —SO$_3$H,

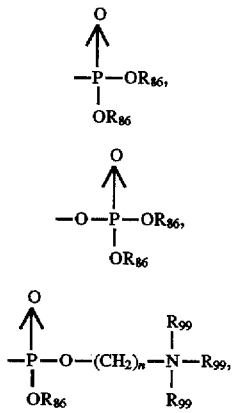

-continued
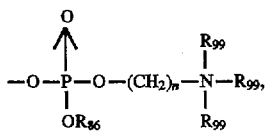
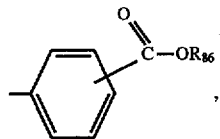
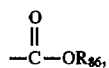
-continued
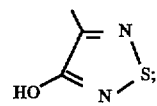
where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.
* * * * *